(12) United States Patent
Kwon

(10) Patent No.: US 8,889,181 B2
(45) Date of Patent: Nov. 18, 2014

(54) IMMUNOSTIMULATORY COMPOSITIONS COMPRISING LIPOSOME-ENCAPSULATED OLIGONUCLEOTIDES AND EPITOPES

(75) Inventor: Hyung-Joo Kwon, Cheongju-si (KR)

(73) Assignee: Industry Academic Cooperation Foundation, Hallym University, Chuncheon, Gangwon-Do (KR)

( * ) Notice: Subject to any disclaimer, the term of this patent is extended or adjusted under 35 U.S.C. 154(b) by 15 days.

(21) Appl. No.: 13/383,898

(22) PCT Filed: Jun. 16, 2010

(86) PCT No.: PCT/KR2010/003879
§ 371 (c)(1), (2), (4) Date: Jan. 13, 2012

(87) PCT Pub. No.: WO2011/007961
PCT Pub. Date: Jan. 20, 2011

(65) Prior Publication Data
US 2012/0114746 A1    May 10, 2012

(30) Foreign Application Priority Data
Jul. 17, 2009 (KR) .................. 10-2009-0065495

(51) Int. Cl.
| | |
|---|---|
| A61K 9/127 | (2006.01) |
| A61K 39/00 | (2006.01) |
| A61P 37/04 | (2006.01) |
| A61P 31/12 | (2006.01) |
| A61K 39/29 | (2006.01) |
| A61K 39/155 | (2006.01) |
| A61K 31/7088 | (2006.01) |
| A61K 45/06 | (2006.01) |
| C12N 7/00 | (2006.01) |
| A61K 47/48 | (2006.01) |
| A61K 39/145 | (2006.01) |

(52) U.S. Cl.
CPC ..... *A61K 39/145* (2013.01); *C12N 2760/16134* (2013.01); *A61K 39/29* (2013.01); *C12N 2760/16161* (2013.01); *A61K 39/155* (2013.01); *A61K 39/0011* (2013.01); *A61K 31/7088* (2013.01); *A61K 45/06* (2013.01); *C12N 7/00* (2013.01); *A61K 47/48815* (2013.01); *A61K 2039/55555* (2013.01); *A61K 2039/55561* (2013.01)
USPC ............. 424/450; 424/184.1; 424/186.1; 435/7.92; 435/375; 435/455; 435/458

(58) Field of Classification Search
CPC .......... A61K 2300/00; A61K 31/7088; A61K 39/0011; A61K 39/145; A61K 39/155; A61K 39/29; A61K 2039/55555; A61K 2039/55561; A61K 45/06; A61K 47/48815; C12N 2760/16134; C12N 2760/16161; C12N 7/00
USPC ................. 424/450, 184.1, 186.1; 435/7.92
See application file for complete search history.

(56) References Cited

PUBLICATIONS

Jospeh et al. Vaccine vol. 20, pp. 3342-3354, 2002.*
Müller-Pillasch et al. vol. 208, Issue 1, Feb. 16, 1998, pp. 25-30.*
Sette et al. vol. 15, Issue 4, Aug. 2003, pp. 461-470.*
Collins et al., "Processing of Exogenous Liposome-Encapsulated Antigens in vivo Generates Class I MHC-Restricted T Cell Responses," J. Immunol. 148:3336-3341, 1992.(Abstract).
Joseph et al., "Liposomal Immunostimulatory DNA Sequence (ISS-ODN): An Efficient Parenteral and Mucosal Adjuvant for Influenza and Hepatitis B Vaccines," Vaccine 20:3342-3354, 2002.
Ludewig et al., "In vivo Antigen Loading and Activation of Dendritic Cells via a Liosomal Peptide Vaccine Mediates Protective Antiviral and Anti-Tumour Immunity," Vaccine 19:23-32, 2001.

\* cited by examiner

*Primary Examiner* — Janet Epps-Smith
(74) *Attorney, Agent, or Firm* — Clark & Elbing LLP

(57) ABSTRACT

The present invention relates to a composition for enhancing an immune response, an epitope having immunogenicity, screening and preparing method thereof, a antibody to peptide antigen and screening and preparing method thereof. The composition of the present invention may be effectively used for preventing or treating diverse immune-deficiency diseases such as cancer, influenza virus, hepatitis C virus and RSV (respiratory syncytial virus) by enhancing immune responses.

10 Claims, 61 Drawing Sheets

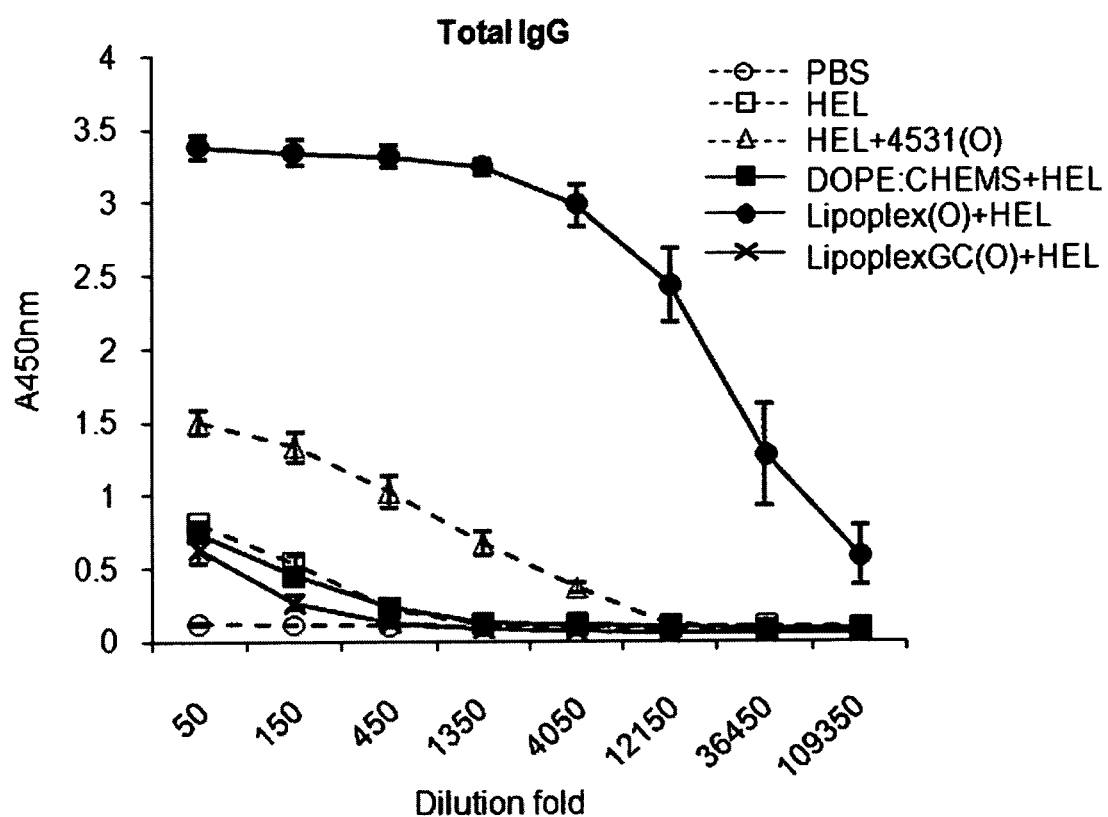

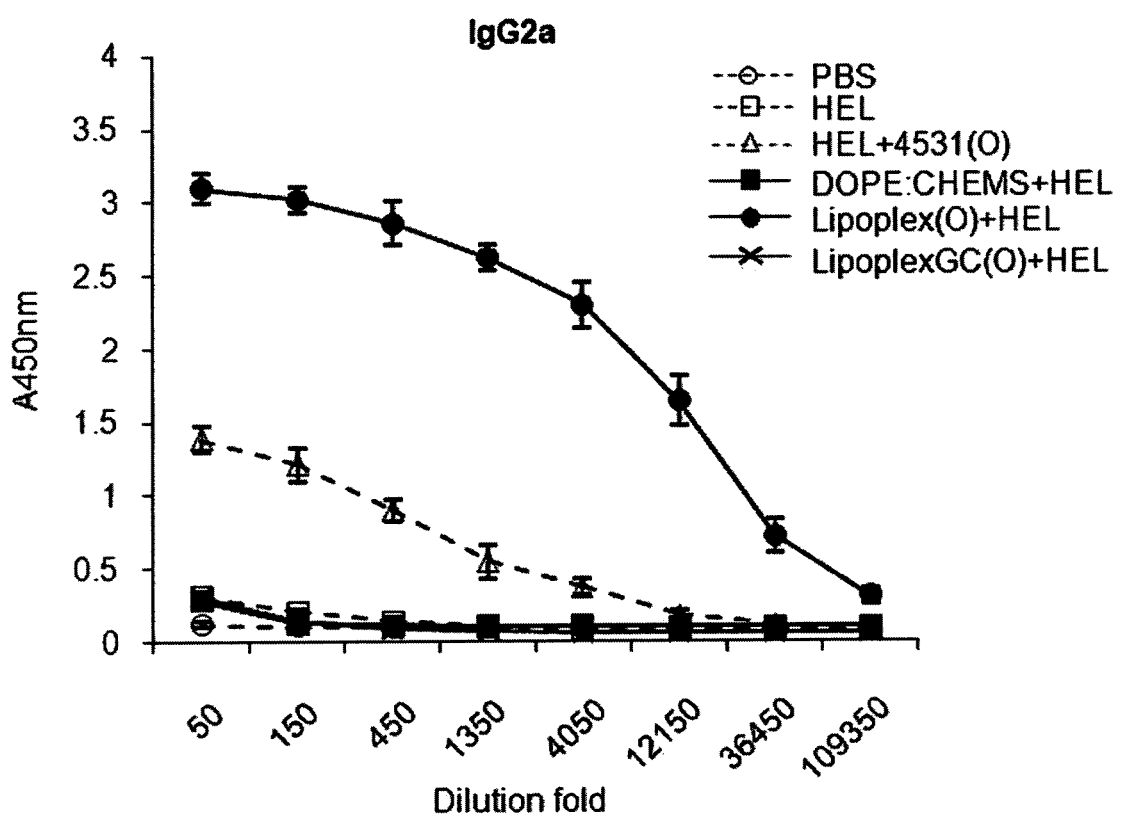

[Bar chart: Serum IgG (ng/ml) vs. conditions]

Y-axis: Serum IgG (ng/ml), 0 to 40000

X-axis labels:
hH5N1 HA233 + 4531(O): −, +, +, +, +, +, +, +, +, +

Conditions: DOPE:CHEMS (6:4), DOPE:CHEMS (1:1), DOPE:CHEMS (1:0), DOPE:CHEMS (0:1), Lipofectin, Lipofectamine, DOTAP, Poloxamer 407

Fig. 3b

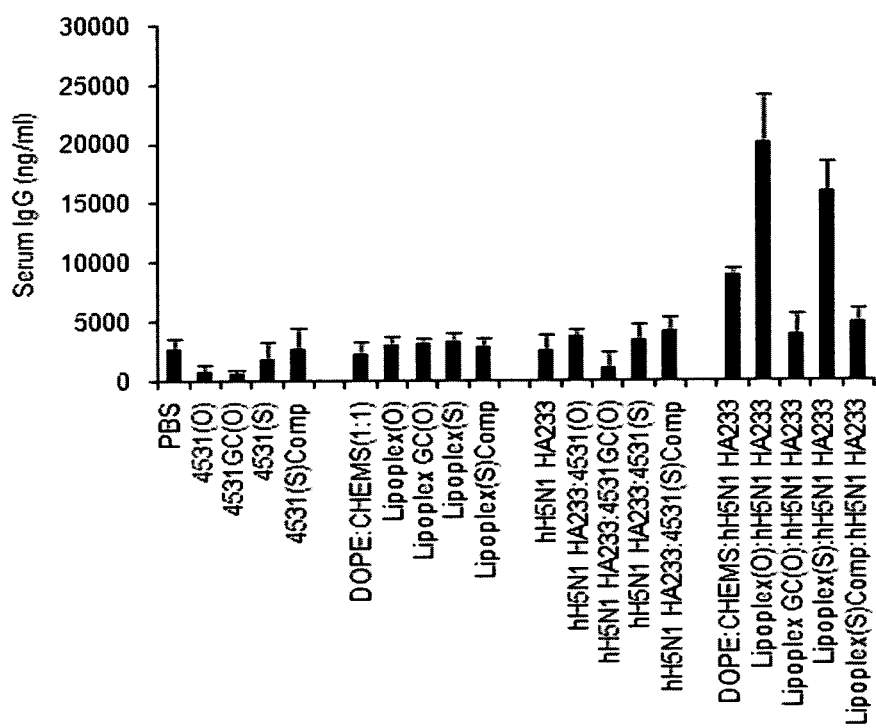

Fig. 8f
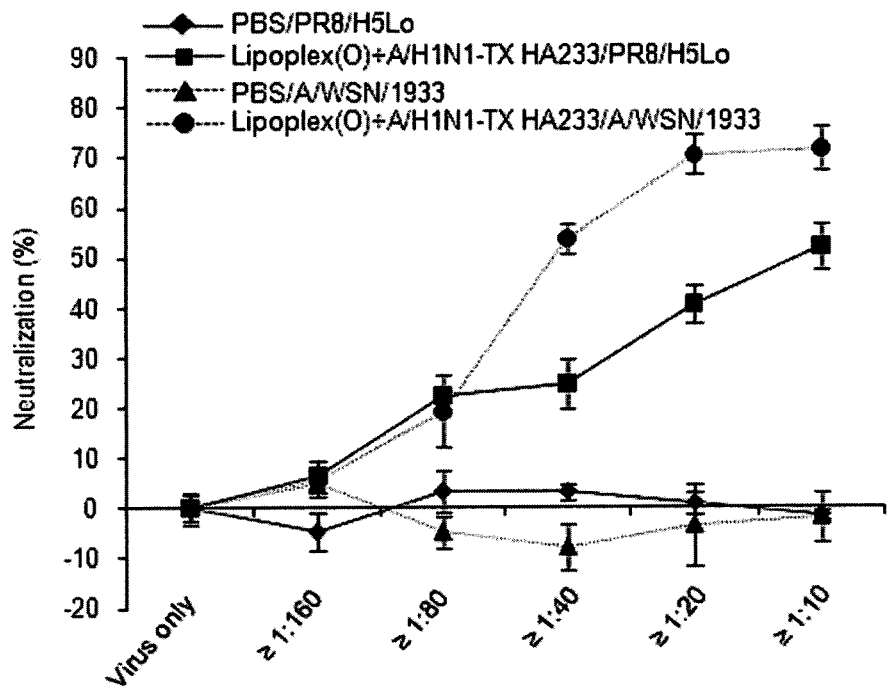
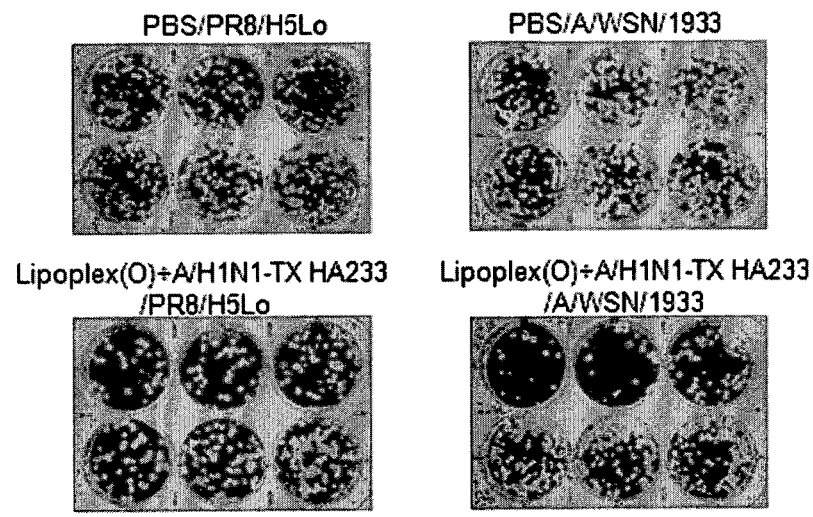

Survival rate (%) vs Days after infection

- PBS
- PBS/PR8/H5Lo
- Lipoplex(O)/PR8/H5Lo
- Lipoplex(O)+hH5N1 HA233/PR8/H5Lo
- LipoplexGC(O)+hH5N1 HA233/PR8/H5Lo

Fig. 11b

Bodyweight (g) vs Days after infection

- PBS
- PBS/PR8/H5Lo
- Lipoplex(O)/PR8/H5Lo
- Lipoplex(O)+hH5N1 HA233/PR8/H5Lo
- LipoplexGC(O)+hH5N1 HA233/PR8/H5Lo

|  | A/WSN/1933 | |
| Immunization: PBS | PBS | Lipoplex(O) + hH1N1-WSN HA230 |

3 Day

6 Day

PR8/H5Lo

Lipoplex(O) + hH1N1-WSN HA230

3 Day

6 Day

A/WSN/1933

PBS | Lipoplex(O)
+hH1N1-HK HA233

6 Day

18 Day

Fig. 16a
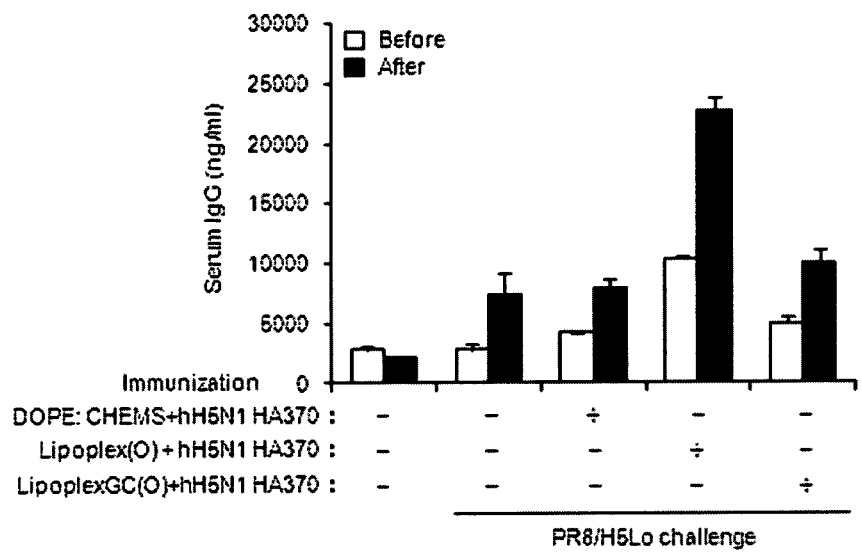
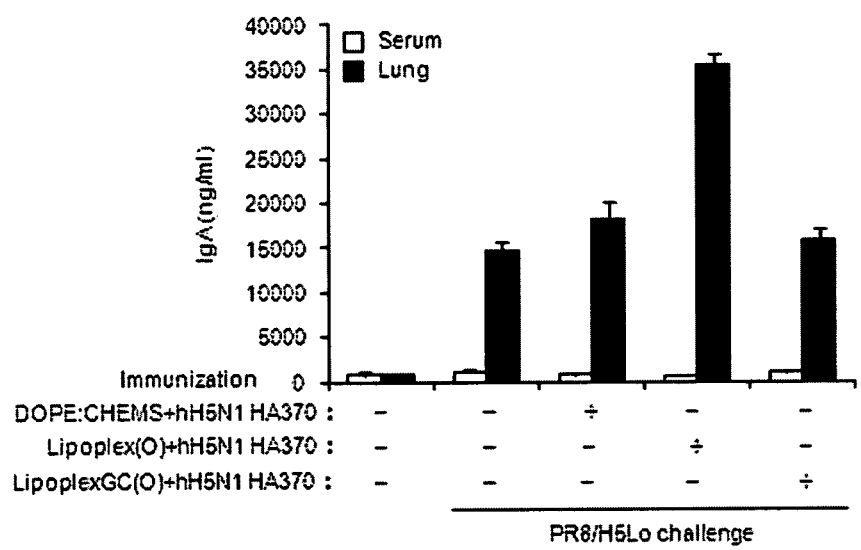

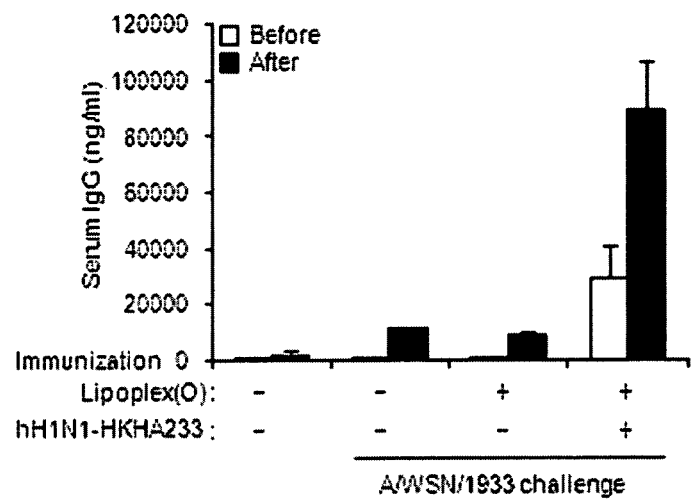
Fig. 16e
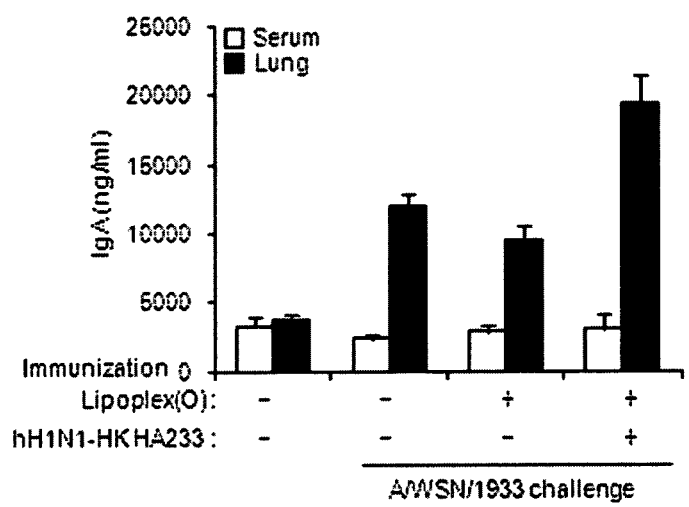

Coating : hH5N1 HA233
- PBS
- Inactivated PR8/H5Lo
- DOPE:CHEMS +inactivated PR8/H5Lo
- Lipoplex(O)+inactivated PR8/H5Lo
- Lipoplex(O)+hH5N1 HA233

Fig. 18d

Coating : hH5N1 HA370
- PBS
- Inactivated PR8/H5Lo
- DOPE:CHEMS +inactivated PR8/H5Lo
- Lipoplex(O)+inactivated PR8/H5Lo
- Lipoplex(O)+hH5N1 HA370

Fig. 27a
Control
BNL 1MEA.7R.1
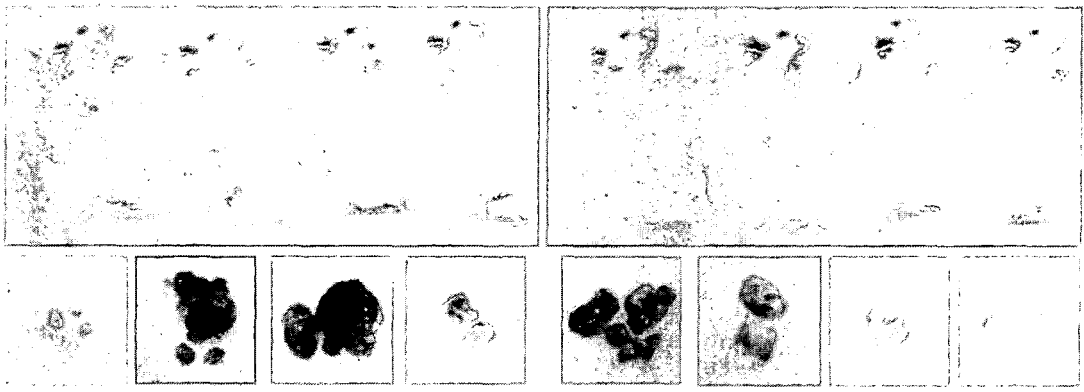
Lipoplex(O)+TM4SF5R2-3/BNL 1MEA.7R.1
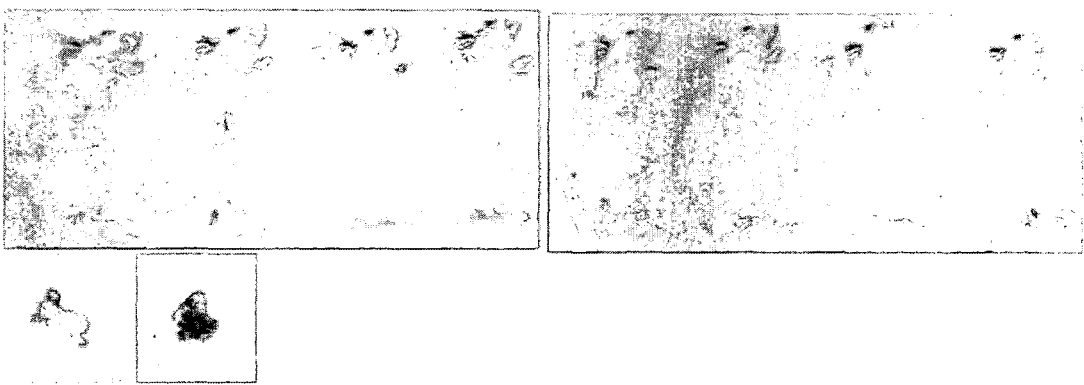

SEQUENCE LISTING

```
<160> NUMBER OF SEQ ID NOS: 46

<210> SEQ ID NO 1
<211> LENGTH: 11
<212> TYPE: PRT
<213> ORGANISM: Influenza A virus

<400> SEQUENCE: 1

Ile Leu Glu Lys Lys His Asn Gly Lys Leu Cys
1               5                   10

<210> SEQ ID NO 2
<211> LENGTH: 14
<212> TYPE: PRT
<213> ORGANISM: Influenza A virus

<400> SEQUENCE: 2

Ile Ala Thr Arg Ser Lys Val Asn Gly Gln Ser Gly Arg Met
1               5                   10

<210> SEQ ID NO 3
<211> LENGTH: 15
<212> TYPE: PRT
<213> ORGANISM: Influenza A virus

<400> SEQUENCE: 3

Leu Arg Asn Ser Pro Gln Arg Glu Arg Arg Lys Lys Arg Gly
1               5                   10                  15

<210> SEQ ID NO 4
<211> LENGTH: 17
<212> TYPE: PRT
<213> ORGANISM: Influenza A virus

<400> SEQUENCE: 4

His His Ser Asn Glu Gln Gly Ser Gly Tyr Ala Ala Asp Lys Glu Ser
1               5                   10                  15

Thr
```

-continued

```
<210> SEQ ID NO 5
<211> LENGTH: 14
<212> TYPE: PRT
<213> ORGANISM: Influenza A virus

<400> SEQUENCE: 5

Ile Ala Lys Arg Pro Lys Val Arg Asp Gln Glu Gly Arg Ile
1               5                   10

<210> SEQ ID NO 6
<211> LENGTH: 14
<212> TYPE: PRT
<213> ORGANISM: Influenza A virus

<400> SEQUENCE: 6

Ile Ala Ala Arg Pro Lys Val Lys Asp Gln His Gly Arg Met
1               5                   10

<210> SEQ ID NO 7
<211> LENGTH: 14
<212> TYPE: PRT
<213> ORGANISM: Influenza A virus

<400> SEQUENCE: 7

Ile Ala Ile Arg Pro Lys Val Arg Asp Gln Glu Gly Arg Met
1               5                   10

<210> SEQ ID NO 8
<211> LENGTH: 17
<212> TYPE: PRT
<213> ORGANISM: Influenza A virus

<400> SEQUENCE: 8

His His Gln Asn Glu Gln Gly Ser Gly Tyr Ala Ala Asp Leu Lys Ser
1               5                   10                  15

Thr

<210> SEQ ID NO 9
<211> LENGTH: 17
<212> TYPE: PRT
<213> ORGANISM: Influenza A virus

<400> SEQUENCE: 9

His His Gln Asn Glu Gln Gly Ser Gly Tyr Ala Ala Asp Gln Lys Ser
1               5                   10                  15

Thr

<210> SEQ ID NO 10
<211> LENGTH: 14
<212> TYPE: PRT
<213> ORGANISM: Homo sapiens

<400> SEQUENCE: 10

Asn Arg Thr Leu Trp Asp Arg Cys Glu Ala Pro Pro Arg Val
1               5                   10

<210> SEQ ID NO 11
<211> LENGTH: 15
<212> TYPE: PRT
<213> ORGANISM: Homo sapiens

<400> SEQUENCE: 11

Gly Ala Tyr Leu Leu Asn Arg Thr Leu Trp Asp Arg Cys Glu Ala
1               5                   10                  15
```

```
<210> SEQ ID NO 12
<211> LENGTH: 12
<212> TYPE: PRT
<213> ORGANISM: Hepatitis C virus

<400> SEQUENCE: 12

Cys Phe Arg Lys His Pro Glu Ala Thr Tyr Ser Arg
1               5                   10

<210> SEQ ID NO 13
<211> LENGTH: 18
<212> TYPE: PRT
<213> ORGANISM: respiratory syncytial virus

<400> SEQUENCE: 13

Met Ser Lys His Lys Asn Gln Arg Thr Ala Arg Thr Leu Glu Lys Thr
1               5                   10                  15

Trp Asp

<210> SEQ ID NO 14
<211> LENGTH: 20
<212> TYPE: DNA
<213> ORGANISM: Mycobacterium bovis

<400> SEQUENCE: 14
agcagcgttc gtgtcggcct                                              20

<210> SEQ ID NO 15
<211> LENGTH: 20
<212> TYPE: DNA
<213> ORGANISM: Artificial Sequence
<220> FEATURE:
<223> OTHER INFORMATION: MB-ODN 4531(O)GC

<400> SEQUENCE: 15
agcaggcttc gtgtcggcct                                              20

<210> SEQ ID NO 16
<211> LENGTH: 13
<212> TYPE: DNA
<213> ORGANISM: Mycobacterium bovis

<400> SEQUENCE: 16
agcagcgttc ttg                                                     13

<210> SEQ ID NO 17
<211> LENGTH: 20
<212> TYPE: DNA
<213> ORGANISM: Artificial Sequence
<220> FEATURE:
<223> OTHER INFORMATION: MB-ODN 4531(S)CT

<400> SEQUENCE: 17
agcagcgttc ttgtcggcct                                              20

<210> SEQ ID NO 18
<211> LENGTH: 20
<212> TYPE: DNA
<213> ORGANISM: Artificial Sequence
<220> FEATURE:
<223> OTHER INFORMATION: MB-4531(S)CS

<400> SEQUENCE: 18
```
aggccgacaa gaacgctgct 20

<210> SEQ ID NO 19
<211> LENGTH: 17
<212> TYPE: PRT
<213> ORGANISM: Artificial Sequence
<220> FEATURE:
<223> OTHER INFORMATION: hH5N1-HK HA370

<400> SEQUENCE: 19

His His Ser Asn Glu Gln Gly Ser Gly Tyr Ala Ala Asp Gln Glu Ser
1               5                   10                  15

Thr

<210> SEQ ID NO 20
<211> LENGTH: 14
<212> TYPE: PRT
<213> ORGANISM: Artificial Sequence
<220> FEATURE:
<223> OTHER INFORMATION: hH5N1 HA 233-1

<400> SEQUENCE: 20

Ile Ala Thr Arg Pro Lys Val Asn Gly Gln Ser Gly Arg Met
1               5                   10

<210> SEQ ID NO 21
<211> LENGTH: 14
<212> TYPE: PRT
<213> ORGANISM: Artificial Sequence
<220> FEATURE:
<223> OTHER INFORMATION: hH5N1 233-2

<400> SEQUENCE: 21

Ile Ala Thr Arg Ser Lys Val Asn Gly Gln Asn Gly Arg Met
1               5                   10

<210> SEQ ID NO 22
<211> LENGTH: 14
<212> TYPE: PRT
<213> ORGANISM: Artificial Sequence
<220> FEATURE:
<223> OTHER INFORMATION: hH5N1 HA233-3

<400> SEQUENCE: 22

Met Ala Thr Arg Ser Lys Val Asn Gly Gln Ser Gly Arg Met
1               5                   10

<210> SEQ ID NO 23
<211> LENGTH: 14
<212> TYPE: PRT
<213> ORGANISM: Artificial Sequence
<220> FEATURE:
<223> OTHER INFORMATION: hH5N1 HA233-4

<400> SEQUENCE: 23

Ile Ala Thr Arg Ser Lys Val Asn Gly Gln Ser Gly Arg Ile
1               5                   10

<210> SEQ ID NO 24
<211> LENGTH: 14
<212> TYPE: PRT
<213> ORGANISM: Artificial Sequence
<220> FEATURE:
<223> OTHER INFORMATION: hH5N1 HA233-6

<400> SEQUENCE: 24

```
Ile Ala Thr Arg Ser Lys Ile Asn Gly Gln Ser Gly Arg Ile
1               5                   10
```

<210> SEQ ID NO 25
<211> LENGTH: 14
<212> TYPE: PRT
<213> ORGANISM: Artificial Sequence
<220> FEATURE:
<223> OTHER INFORMATION: hH5N1 HA233-7

<400> SEQUENCE: 25

```
Ile Ala Thr Arg Ser Lys Ile Asn Gly Gln Ser Gly Arg Met
1               5                   10
```

<210> SEQ ID NO 26
<211> LENGTH: 14
<212> TYPE: PRT
<213> ORGANISM: Artificial Sequence
<220> FEATURE:
<223> OTHER INFORMATION: hH5N1 HA233-9

<400> SEQUENCE: 26

```
Ile Ala Ala Arg Ser Lys Val Asn Gly Gln Ser Gly Arg Met
1               5                   10
```

<210> SEQ ID NO 27
<211> LENGTH: 14
<212> TYPE: PRT
<213> ORGANISM: Artificial Sequence
<220> FEATURE:
<223> OTHER INFORMATION: hH5N1 HA233-11

<400> SEQUENCE: 27

```
Ile Ala Thr Arg Ser Lys Val Asn Gly Gln Ile Gly Arg Met
1               5                   10
```

<210> SEQ ID NO 28
<211> LENGTH: 17
<212> TYPE: PRT
<213> ORGANISM: Artificial Sequence
<220> FEATURE:
<223> OTHER INFORMATION: hH1N1-NY HA370

<400> SEQUENCE: 28

```
His His Gln Asn Glu Gln Gly Ser Gly Tyr Ala Ala Asp Lys Lys Ser
1               5                   10                  15

Thr
```

<210> SEQ ID NO 29
<211> LENGTH: 17
<212> TYPE: PRT
<213> ORGANISM: Artificial Sequence
<220> FEATURE:
<223> OTHER INFORMATION: hH1N1-OH HA370

<400> SEQUENCE: 29

```
His His Gln Asn Glu Gln Gly Ser Gly Tyr Ala Ala Asp Arg Lys Ser
1               5                   10                  15

Thr
```

<210> SEQ ID NO 30
<211> LENGTH: 14
<212> TYPE: PRT
<213> ORGANISM: Artificial Sequence
<220> FEATURE:
<223> OTHER INFORMATION: hH1N1-Thai HA233

<400> SEQUENCE: 30

Ile Ala Lys Arg Pro Lys Val Arg Gly Gln Ala Gly Arg Met
1 5 10

<210> SEQ ID NO 31
<211> LENGTH: 14
<212> TYPE: PRT
<213> ORGANISM: Artificial Sequence
<220> FEATURE:
<223> OTHER INFORMATION: mH2N5 HA233

<400> SEQUENCE: 31

Ile Ala Thr Arg Pro Lys Val Asn Gly Gln Gly Gly Arg Met
1 5 10

<210> SEQ ID NO 32
<211> LENGTH: 14
<212> TYPE: PRT
<213> ORGANISM: Artificial Sequence
<220> FEATURE:
<223> OTHER INFORMATION: hH7N7 HA233

<400> SEQUENCE: 32

Pro Gly Ala Arg Pro Gln Val Asn Gly Gln Ser Gly Arg Ile
1 5 10

<210> SEQ ID NO 33
<211> LENGTH: 17
<212> TYPE: PRT
<213> ORGANISM: Artificial Sequence
<220> FEATURE:
<223> OTHER INFORMATION: hH7N7 HA370

<400> SEQUENCE: 33

Arg His Gln Asn Ala Gln Gly Glu Gly Thr Ala Ala Asp Tyr Lys Ser
1 5 10 15

Thr

<210> SEQ ID NO 34
<211> LENGTH: 14
<212> TYPE: PRT
<213> ORGANISM: Artificial Sequence
<220> FEATURE:
<223> OTHER INFORMATION: hH9N2 HA233

<400> SEQUENCE: 34

Ile Gly Pro Arg Pro Leu Val Asn Gly Leu Gln Gly Arg Ile
1 5 10

<210> SEQ ID NO 35
<211> LENGTH: 17
<212> TYPE: PRT
<213> ORGANISM: Artificial Sequence
<220> FEATURE:
<223> OTHER INFORMATION: hH9N2-ST HA370

<400> SEQUENCE: 35

Gln His Ser Lys Tyr Gln Gly Val Gly Met Ala Ala Asp Arg Asp Ser
1 5 10 15

Thr

<210> SEQ ID NO 36
<211> LENGTH: 17
<212> TYPE: PRT

-continued

<213> ORGANISM: Artificial Sequence
<220> FEATURE:
<223> OTHER INFORMATION: hH9N2-HK HA370

<400> SEQUENCE: 36

Gln His Ser Asn Asp Gln Gly Val Gly Met Ala Ala Asp Arg Asp Ser
1 5 10 15

Thr

<210> SEQ ID NO 37
<211> LENGTH: 14
<212> TYPE: PRT
<213> ORGANISM: Artificial Sequence
<220> FEATURE:
<223> OTHER INFORMATION: sH15N2 HA233

<400> SEQUENCE: 37

Pro Gly Ala Arg Pro Lys Val Asn Gly Gln Ala Gly Arg Ile
1 5 10

<210> SEQ ID NO 38
<211> LENGTH: 15
<212> TYPE: PRT
<213> ORGANISM: Artificial Sequence
<220> FEATURE:
<223> OTHER INFORMATION: HRSV-Fa3

<400> SEQUENCE: 38

Lys Val Lys Leu Ile Lys Gln Glu Leu Asp Lys Tyr Lys Asn Ala
1 5 10 15

<210> SEQ ID NO 39
<211> LENGTH: 15
<212> TYPE: PRT
<213> ORGANISM: Artificial Sequence
<220> FEATURE:
<223> OTHER INFORMATION: HRSV-Fa3-2

<400> SEQUENCE: 39

Lys Val Lys Leu Ile Lys Gln Glu Leu Asp Lys Tyr Lys Ser Ala
1 5 10 15

<210> SEQ ID NO 40
<211> LENGTH: 15
<212> TYPE: PRT
<213> ORGANISM: Artificial Sequence
<220> FEATURE:
<223> OTHER INFORMATION: HRSV-F7

<400> SEQUENCE: 40

Ala Gly Ser Val Ser Phe Phe Pro Gln Ala Glu Thr Cys Lys Val
1 5 10 15

<210> SEQ ID NO 41
<211> LENGTH: 15
<212> TYPE: PRT
<213> ORGANISM: Artificial Sequence
<220> FEATURE:
<223> OTHER INFORMATION: HRSV-F9

<400> SEQUENCE: 41

Cys Lys Ile Met Thr Ser Lys Thr Asp Val Ser Ser Ser Val Ile
1 5 10 15

```
<210> SEQ ID NO 42
<211> LENGTH: 15
<212> TYPE: PRT
<213> ORGANISM: Artificial Sequence
<220> FEATURE:
<223> OTHER INFORMATION: hIB4-VWA-1-2

<400> SEQUENCE: 42

Lys Glu Pro Trp Pro Asn Ser Asp Pro Pro Phe Ser Phe Lys Asn
1               5                   10                  15

<210> SEQ ID NO 43
<211> LENGTH: 19
<212> TYPE: PRT
<213> ORGANISM: Artificial Sequence
<220> FEATURE:
<223> OTHER INFORMATION: hIB4-VWA-1-3

<400> SEQUENCE: 43

Pro Gln Thr Asp Met Arg Pro Glu Lys Leu Lys Glu Pro Trp Pro Asn
1               5                   10                  15

Ser Asp Pro

<210> SEQ ID NO 44
<211> LENGTH: 20
<212> TYPE: PRT
<213> ORGANISM: Artificial Sequence
<220> FEATURE:
<223> OTHER INFORMATION: hIB4-VWA-2

<400> SEQUENCE: 44

Leu Thr Glu Asp Val Asp Glu Phe Arg Asn Lys Leu Gln Gly Glu Arg
1               5                   10                  15

Ile Ser Gly Asn
            20

<210> SEQ ID NO 45
<211> LENGTH: 20
<212> TYPE: PRT
<213> ORGANISM: Artificial Sequence
<220> FEATURE:
<223> OTHER INFORMATION: hIB4-VWA-3

<400> SEQUENCE: 45

Leu Asp Thr Thr Gly Thr Tyr Thr Gln Tyr Arg Thr Gln Asp Tyr Pro
1               5                   10                  15

Ser Val Pro Thr
            20

<210> SEQ ID NO 46
<211> LENGTH: 15
<212> TYPE: PRT
<213> ORGANISM: Artificial Sequence
<220> FEATURE:
<223> OTHER INFORMATION: hIB4-EGF-1

<400> SEQUENCE: 46

Leu Gln Lys Glu Val Arg Ser Ala Arg Cys Ser Phe Asn Gly Asp
1               5                   10                  15
```

IMMUNOSTIMULATORY COMPOSITIONS COMPRISING LIPOSOME-ENCAPSULATED OLIGONUCLEOTIDES AND EPITOPES

Cross-Reference to Related Applications

This application is the U.S. national stage filing under 35 U.S.C. §371 of international application PCT/KR2010/003879, filed Jun. 16, 2010, which claims benefit of Korean Patent Application 10-2009-0065495, filed Jul. 17, 2009.

BACKGROUND OF THE INVENTION

1. Field of the Invention

The present invention relates to an immunostimulatory compositions comprising liposome-encapsulated oligonucleotide and epitopes.

2. Description of the Related Art

Epitope-based peptide vaccines are extensively studied that are pivotal for inducing and regulating immune responses through their binding ability to B cell receptor (BCR) and MHC as B-cell epitope and T-cell epitope for protecting infectious and malignant diseases (1-3). Chemically inactivated vaccines are widely used in the clinics, however, the vaccines have disadvantages, such as the risk of virus reactivation, the cost for the maintenance of the vaccine stability, leading to autoimmune diseases, not support to sufficient protection in some of vaccines (1, 3, 4). For overcoming the theses disadvantages, synthetic peptides were developed for last 30 years to manipulate of the immune responses through the use of epitopes designed for stimulating particular subsets of lymphocytes, leading to selective B- and T-cell responses. Therefore, peptide vaccines have gained attention as potentially useful prophylaxis and therapy for anticancer vaccines (5, 6) and infectious diseases such as influenza virus (3), malaria (7), hepatitis B (8), and HIV (9). Although peptide vaccines were actively studied in various animal models, their efficacy is limited to treat human. To improve the peptide vaccine efficacy, liposomes are evaluated for delivery of vaccines (10) and adjuvants such as flagella (11) and CpG-DNA (12) were formulated for enhancing the magnitude of immune responses.

Liposomes as vehicles for delivery have been extensively evaluated in developing vaccines to enhance cytotoxic T lymphocytes (CTL) responses (10, 13). Encapsulated liposomes can protect from environment and deliver to target cells. pH-sensitive liposomes such as phosphatidyl-β-oleoyl-γ-palmitoyl ethanolamine (DOPE, dioleryl phosphatidylethanolamine)/cholesteryl hemisuccinate (CHEMS) are characteristics release of contents into the cytosol and lipid intermixing at low pH (5.0) (14). Investigators have shown that the pH-sensitive liposomes improve antigen delivery to the cytosol and induction of CTL responses (15). Furthermore, effective antigen specific CTL responses are reported in mice immunized with CTL epitopes synthesized from Hantaan nucleocapsid protein (M6) or human papilloma virus E7 encapsulated in pH-sensitive liposomes (16). To improve uptake of antigens by macrophages and dendritic cells, cationic liposomes were used as vehicles for delivery. The CTL response and antibody production are enhanced by encapsulated cationic liposomes such as lipofectamine, DC-Chol, DC-Chol/DOPE, EPC/SA/C etc (10).

Although liposomes are potent vehicles for delivering antigen to APCs, it is investigated to enhance of immunogenicity and adjuvanticity. The immunostimulatory activities of CpG-DNA have gained attention as a potentially useful form of therapeutics for immunoadjuvants compare to other immune-stimulating agents such as flagella, lipid A, cytokines etc (17, 18). Several investigators have shown that CpG-DNA upregulates antigen-presenting cell activity, Th1 immune response, immunoglobulin (Ig) isotype switching (19-21). The immunostimulatory activities as a potent adjuvant are enhanced by liposome-encapsulated CpG-DNA. Suzuki et al., show that CpG-DNA encapsulated in cationic liposomes induces expression of IL-12 and IFN-γ and CpG-DNA-liposome coencapsulated with ovalbumin (OVA) caused the induction of OVA-specific CTLs, which exhibited potent cytotoxicity against OVA-expressing tumor (22). In addition, SSCL improves the uptake by B cells, dendritic cells, and macrophages and coencapsulation of CpG-DNA with OVA magnified the Ag-specific IFN-γ and IgG production (23). Furthermore, Li et al., investigate that CpG-DNA and HER-2/neu-derived peptide coencapsulated in DSPC/Chol liposomes enhances the CTL response and IgG production (24).

Phosphorothioate-modified CpG-DNAs (PS-DNA), which is a sulfur substitution for the nonbridging oxygens in the backbone providing its nuclease resistance and efficient uptake into cells, have been used for clinical applications (25). However, several studies indicated that PS-DNA induces backbone-related side effects such as transient splenomegaly, lymphoid follicle destruction, and arthritis (26-28). Therefore, investigators developed the natural counterpart of the phosphodiester bond CpG-DNA (PO-DNA) to induce optimal innate immune responses without severe side effects. In contrast to PS-DNA, effects of PO-DNA were not seen in human cells. However, inductions of effective immune responses are reported in human cells stimulated with PO-DNA and non-CpG-DNA encapsulated in liposomes (DOTAP, lipofectin) (29, 30).

In previous studies, we identified the natural phosphodiester bond CpG-DNA (PO-DNA) through computer-assisted analysis of M. bovis genomic DNA and screened the genomic DNA sequences of M. bovis with immunostimulatory activity (31). Our experimental analyses demonstrate that a potent PO-DNA, namely MB-ODN 4531(O), containing CpG motifs has functional effects as a powerful adjuvant for the induction of Ag-driven Th1 responses without severe side effects (31, 32). In this study, we compared the ability of the PO-DNA (MB-ODN 4531(O)) encapsulated in several liposomes to stimulate immune responses in human and mice cells. Further, we show that PO-DNA (MB-ODN 4531(O)) and several peptides coencapsulated in DOPE/CHEMS liposomes significantly enhanced the peptide-specific IgG production. These results suggest that peptide vaccine efficacy were improved by delivery with DOPE/CHEMS liposomes and adjuvants effect with MB-ODN 4531(O), which can be promptly used for application in pandemic of infectious diseases, development of therapeutic antibody, and exposure of bioterrorism agents.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE INVENTION

The present inventors have made intensive studies to develop a novel immunoadjuvant capable of preventing and treating various cancers and infectious diseases. As results, they have identified the peptide epitopes of protein antigens and discovered that encapsulation of said epitopes and oligonucleotides into liposomes with specific compositions give greatly enhanced immunostimulatory activities.

Accordingly, it is an object of this invention to provide a composition for enhancing immune response.

It is another object of this invention to provide a screening method for an epitope having immunogenicity.

It is still another object of this invention to provide a screening method for an antibody against a protein antigen.

It is further object of this invention to provide a method for preparing an antibody against a protein antigen.

It is still further object of this invention to provide a peptide vaccine composition against an influenza A virus, cancer, a hepatitis C virus or a RSV (respiratory syncytial virus).

Other objects and advantages of the present invention will become apparent from the following detailed description together with the appended claims and drawings.

BRIEF DESCRIPTION OF THE DRAWINGS

FIG. 1a-1c represent a humoral responses of BALB/c mice intraperitoneally immunized by liposome (DOPE:CHEMS (1:1)) and HEL (hen egg lysozyme) complex. The HEL-MB-ODN 4531(O)-liposome complex was injected on three occasions at 10 day intervals. Then, the production of IgG (FIG. 1a), Ig G1 (FIG. 1b) and Ig G2a (FIG. 1c) was analyzed to confirm that the titer of total IgG and the production of the IgG2a which is related to Th1 immune response were increased. We defined MB-ODN 4531(O) encapsulated in a DOPE:CHEMS complex as Lipoplex(O).

FIGS. 2a-2e represent the epitope selection from the HA (hemagglutinin) of an avian influenza A (H5N1)/Vietnam/2004 strain considering hydrophilicity, hydrophobicity, secondary structure, antigenicity and amphiphilicity for preparing peptide-PO-DNA(MB-ODN4531(O))-liposome complex. The selected 10 candidate epitopes (hH5N1 HA58, hH5N1 HA113, hH5N1 HA233, hH5N1 HA336, hH5N1 HA363, hH5N1 HA370, hH5N1 HA377, hH5N1 HA384, hH5N1 HA387 and hH5N1 HA394) were prepared as peptide-PO-DNA (MB-ODN4531(O))-liposome complex and then administered to BALB/c mice intraperitoneally on three occasions and the sera were collected. As a result of analyzing the amount of IgG, it is confirmed that the amounts of each peptide-specific total IgG (FIG. 2a), amounts of each peptide-specific IgG1 (FIG. 2b), and the titers of each peptide-specific total IgG (FIG. 2d) and the production of the IgG2a (FIG. 2c) which is related to Th1 immune response were increased. Further, we also examined that the larger amounts of hH5N1 HA370 peptide-specific IgG (IgG2a) was produced in the secondary and tertiary responses (FIG. 2e). Amino acid sequence of A/Vietnam/1203/2004 hH5N1 HA protein is numbered on the basis of alignment with the human H3 sequence (A/Aichi/2/68).

FIG. 3a-3b represent the result derived from the collected sera obtained through the three intraperitoneal administrations to BLAB/c mice of PO-DNA (MB-ODN4531(O)) and peptide (H5N1 HA233) complexed with various liposomes (DOPE:CHEMS (6:4 ratio), DOPE:CHEMS (1:1 ratio), DOPE:CHEMS (1:0 ratio), DOPE:CHEMS (0:1 ratio), lipofectin, lipofectamine, DOTAP, or poloxamer 407). It is indicated that the amounts of total IgG (FIG. 3a) and the titers of total IgG (FIG. 3b) against H5N1 HA233 peptide are highest where the molar ratio of DOPE:CHEMS is 1:1.

FIG. 4 represents the result derived from the collected sera obtained through the three intraperitoneal administrations to BLAB/c mice of peptide (H5N1 HA233) and liposome (DOPE:CHEMS (1:1)) complexed with PO-DNA, PS-DNA or various non-CpG-DNAs. It is indicated that the amount of total IgG against H5N1 HA 233 peptide is highest where PO-DNA 4531(O) or PS-DNA 4531(S) was complexed than the non-CpG-DNA. The adjuvant effect of MB-ODN 4531 in the H5N1 HA233 peptide-specific IgG production was CG sequence-dependent and backbone modification-independent.

FIGS. 6a-6d represent the effect on IgG production of immunization with a complex of Lipoplex(O) and conserved sequences corresponding to hH5N1 HA233 epitope. The 14 amino acid long conserved sequences in influenza A virus H5N1 strains (Table 5) and various influenza A virus subtypes (Table 6) corresponding to hH5N1 HA233 epitope of A/Viet Nam/1203/2004 strain were synthesized. Three BALB/c mice were immunized i.p. three times at 10 day intervals with 50 µg of each peptide and 50 µg of MB-ODN 4531(O) coencapsulated in DOPE:CHEMS (1:1 ratio) complex (represented as Lipoplex(O)+peptide). The antisera were collected 10 day after final immunization, and then amounts of anti-each peptide-specific total IgG (FIG. 6a, FIG. 6d), amounts of anti-each peptide-specific IgG1 (FIG. 6b), amounts of anti-each peptide-specific IgG2a (FIG. 6c) were assayed by an ELISA.

FIG. 7b) and MB-ODN 4531(O) coencapsulated in DOPE:CHEMS complex on IgG production. The 17 amino acid long conserved sequences in influenza A virus subtypes (H7 and H9) (Table 6, Table 9) corresponding to hH5N1 HA370 (or hH5N1 HA233) epitope of A/Viet Nam/1203/2004 strain were synthesized. Three BALB/c mice were immunized i.p. three times at 10 day intervals with 50 µg of each peptide and 50 µg of MB-ODN 4531(O) coencapsulated in DOPE:CHEMS (1:1 ratio) complex (represented as Lipoplex(O)+peptide). The antisera were collected 10 day after final immunization, and then amounts of anti-each peptide-specific total IgG were assayed by an ELISA.

FIG. 8a-8f represent the analysis of hemagglutination inhibition and virus neutralization confirming the specific recognition of a H5N1 HA protein and a H1N1 HA protein by antisera which is generated by PO-DNA (MB-ODN 4531(O))-peptide (hH5N1 HA233, hH5N1 HA370, hH1N1-WSN HA233, hH1N1-HK HA233)-DOPE:CHEMS complex. FIG. 8a shows that each antisera produced by PO-DNA (MB-ODN 4531(O))-peptide (hH5N1 HA233, hH5N1 HA370, hH1N1-WSN HA233, hH1N1-HK HA233)-DOPE:CHEMS complex inhibits the chicken erythrocyte's hemagglutination induced by recombinant H5N1 virus (rH5N1 virus PR8/H5Lo) and A/WSN/1993 virus. FIG. 8b-f show that each antisera produced by PO-DNA (MB-ODN 4531(O))-peptide (hH5N1 HA233, hH5N1 HA370, hH1N1-WSN HA233, hH1N1-HK HA233)-DOPE:CHEMS complex inhibits the infection of MDCK cells by rH5N1 virus PR8/H5Lo and A/WSN/1993 virus.

FIG. 9a-9d represent prophylactic efficacy of vaccination by PO-DNA (MB-ODN 4531(O))-peptide (hH5N1 HA370)-DOPE:CHEMS complex in mice challenged with the rH5N1 virus. BALB/c mice were immunized i.p. with PO-DNA (MB-ODN 4531(O))-peptide (hH5N1 HA370)-liposome complex on two occasions at 10 day intervals followed by nasal administration of a 10LD50 rH5N1 viruses (PR8/H5Lo). FIG. 9a shows that the mice administered with PO-DNA (MB-ODN 4531(O))-peptide (hH5N1 HA370)-liposome complex survived after nasal administration of the 10LD50 rH5N1 virus. FIG. 9b indicates that the mice administered with PO-DNA (MB-ODN 4531(O))-peptide (hH5N1 HA370)-liposome complex regained their weights after nasal administration of the 10LD50 rH5N1 virus. FIG. 9c represent that the mice administered with PO-DNA (MB-ODN 4531 (O))-peptide (hH5N1 HA370)-liposome complex had normal lung tissue after nasal administration of the 10LD50 rH5N1 virus. FIG. 9d shows that the viruses in lung tissue were decreased in the mice administered with PO-DNA (MB-ODN 4531(O))-peptide (hH5N1 HA370)-liposome complex in 3 days and 6 days after nasal administration of the 10LD50 rH5N1 virus.

FIG. 10a-10d represent prophylactic efficacy of vaccination by PO-DNA (MB-ODN 4531(O))-peptide (hH5N1 HA370)-DOPE:CHEMS complex in mice challenged with the mouse adapted A/WSN/1933 H1N1 virus (maA/WSN/1933 virus). BALB/c mice were immunized i.p. with PO-DNA (MB-ODN 4531(O))-peptide (hH5N1 HA370)-liposome complex on two occasions at 10 day intervals followed by nasal administration of a 10LD50 maA/WSN/1933 virus. FIG. 10a shows that the mice administered with PO-DNA (MB-ODN 4531(O))-peptide (hH5N1 HA370)-liposome complex survived after nasal administration of the 10LD50 maA/WSN/1993 virus. FIG. 10b indicates that the mice administered with maA/WSN/1933 virus complex regained their weights after nasal administration of the 10LD50 maA/WSN/1993 virus. FIG. 10c represent that the mice administered with PO-DNA (MB-ODN 4531(O))-peptide (hH5N1 HA370)-liposome complex had normal lung tissue after nasal administration of the 10LD50 maA/WSN/1993 virus. FIG. 10d shows that the viruses in lung tissue viruses were decreased in the mice administered with PO-DNA (MB-ODN 4531(O))-peptide (hH5N1 HA370)-liposome complex in 3 days and 6 days after nasal administration of the 10LD50 maA/WSN/1993 virus.

FIG. 11a-11c represent prophylactic efficacy of vaccination by PO-DNA (MB-ODN 4531(O))-peptide (hH5N1 HA233)-DOPE:CHEMS complex in mice challenged with the rH5N1 viruses. BALB/c mice were immunized i.p. with PO-DNA (MB-ODN 4531(O))-peptide (hH5N1 HA233)-liposome complex on two occasions at 10 day intervals followed by nasal administration of a 10LD50 rH5N1 viruses (PR8/H5Lo). FIG. 11a shows that the mice administered with PO-DNA (MB-ODN 4531(O))-peptide (hH5N1 HA233)-liposome complex survived after nasal administration of the 10LD50 rH5N1 viruses. FIG. 11b indicates that the mice administered with PO-DNA (MB-ODN 4531(O))-peptide (hH5N1 HA233)-liposome complex restored their weights after nasal administration of the 10LD50 rH5N1 virus. FIG. 11c represent that the mice administered with PO-DNA (MB-ODN 4531(O))-peptide (hH5N1 HA233)-liposome complex had normal lung tissue after nasal administration of the 10LD50 rH5N1 virus.

FIG. 12a-12b represent prophylactic efficacy of vaccination by PO-DNA (MB-ODN 4531(O))-peptide (hH5N1 HA233)-DOPE:CHEMS complex in mice challenged with the maA/WSN/1933 virus. BALB/c mice were immunized i.p. with PO-DNA (MB-ODN 4531(O))-peptide (hH5N1 HA233)-liposome complex on two occasions at 10 day intervals followed by nasal administration of a 10LD50 maA/WSN/1933 virus. FIG. 12a shows that the mice administered with PO-DNA (MB-ODN 4531(O))-peptide (hH5N1 HA233)-liposome complex survived after nasal administration of the 10LD50 maA/WSN/1993 virus. FIG. 12b indicates that the mice administered with PO-DNA (MB-ODN 4531(O))-peptide (hH5N1 HA233)-liposome restored their weights after nasal administration of the 10LD50 maA/WSN/1993 virus.

FIG. 13a-13c represent prophylactic efficacy of vaccination by PO-DNA (MB-ODN 4531(O))-peptide (hH1N1-WSN HA233)-DOPE:CHEMS complex in mice challenged with the maA/WSN/1933 virus or rH5N1 virus (PR8/H5Lo). BALB/c mice were immunized i.p. with PO-DNA (MB-ODN 4531(O))-peptide (hH1N1-WSN HA233)-liposome complex on two occasions at 10 day intervals followed by nasal administration of a 10LD50 maA/WSN/1933 virus or 10LD50 rH5N1 virus PR8/H5Lo. FIG. 13a shows that the mice administered with PO-DNA (MB-ODN 4531(O))-peptide (hH1N1-WSN HA233)-liposome complex survived after nasal administration of the 10LD50 maA/WSN/1933 virus or 10LD50 rH5N1 virus. FIG. 13b indicates that the mice administered with PO-DNA (MB-ODN 4531(O))-peptide (hH1N1-WSN HA233)-liposome complex restored their weights after nasal administration of the 10LD50 maA/WSN/1933 virus or 10LD50 rH5N1 virus. FIG. 13c represent that the mice administered with PO-DNA (MB-ODN 4531(O))-peptide (hH1N1-WSN HA233)-liposome complex had normal lung tissue after nasal administration of the 10LD50 maA/WSN/1933 virus or 10LD50 rH5N1 virus.

FIGS. 14a-14c represent prophylactic efficacy of vaccination by PO-DNA (MB-ODN 4531(O))-peptide (hH1N1-HKN HA233)-DOPE:CHEMS complex in mice challenged with the maA/WSN/1933 virus. BALB/c mice were immunized i.p. with PO-DNA (MB-ODN 4531(O))-peptide (hH1N1-HK HA233)-liposome complex on two occasions at 10 day intervals followed by nasal administration of a 10LD50 maA/WSN/1933 virus. FIG. 14a shows that the mice administered with PO-DNA (MB-ODN 4531(O))-peptide (hH1N1-HK HA233)-liposome complex survived after nasal administration of the 10LD50 maA/WSN/1933 virus. FIG. 14b indicates that the mice administered with PO-DNA (MB-ODN 4531(O))-peptide (hH1N1-HK HA233)-liposome complex restored their weights after nasal administration of the 10LD50 maA/WSN/1933 virus. FIG. 14c represents that the mice administered with PO-DNA (MB-ODN 4531(O))-peptide (hH1N1-HK HA233)-liposome had normal lung tissue after nasal administration of the 10LD50 maA/WSN/1933 virus.

FIG. 16a-16f represent that the production of IgG and IgA antibody against each epitope was increased dramatically in sera and BALF (bronchoalveolar lavage fluid) of the PO-DNA (MB-ODN 4531(O))-peptide (hH5N1 HA233, hH5N1 HA370, hH1N1-WSN HA233, hH1N1-HK HA233)-DOPE:

CHEMS complex-administered mice which was then nasally administered with a 10LD50 rH5N1 virus or a 10LD50 maA/WSN/1993 virus.

Figures 17A, 17B:
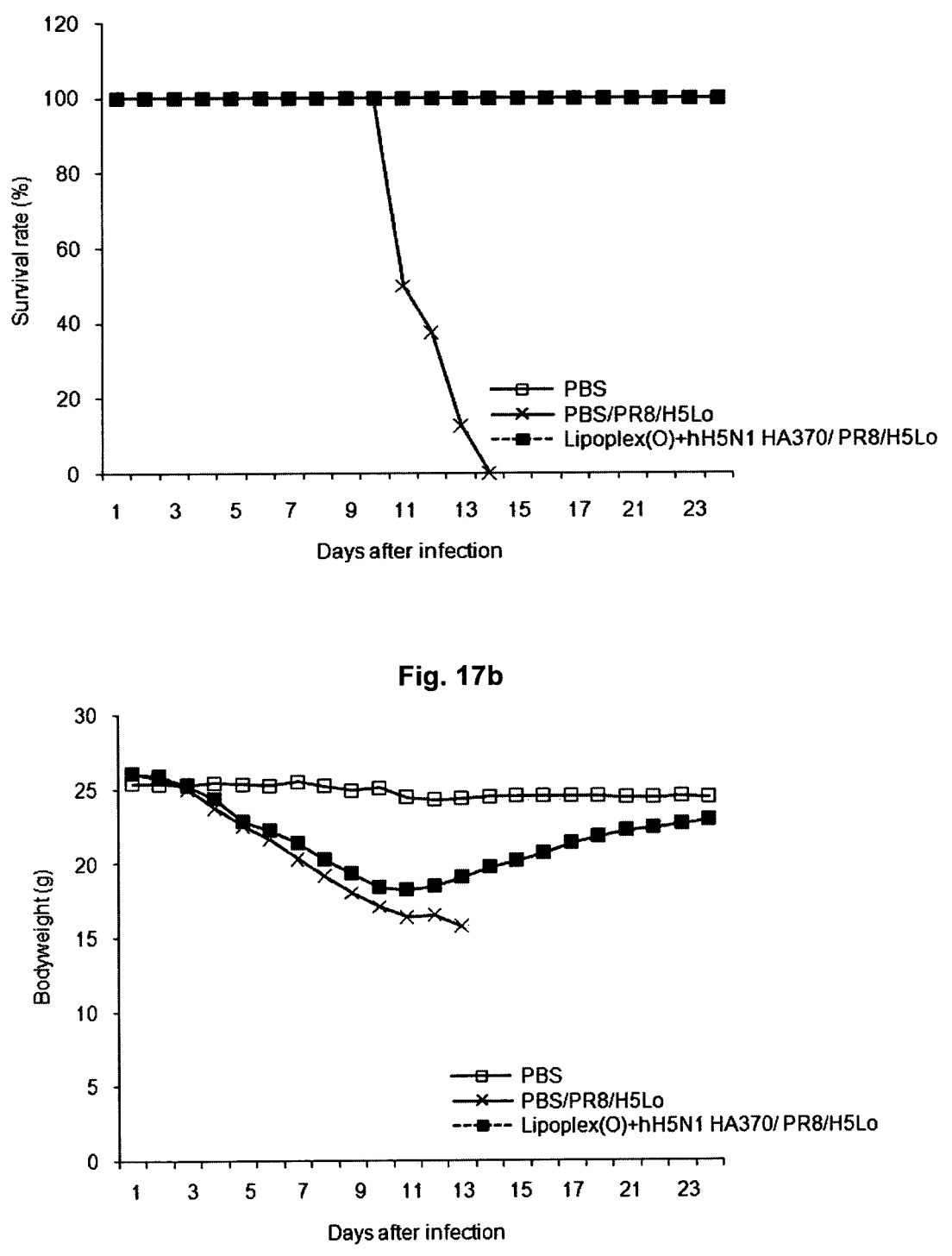
Figure 17C:
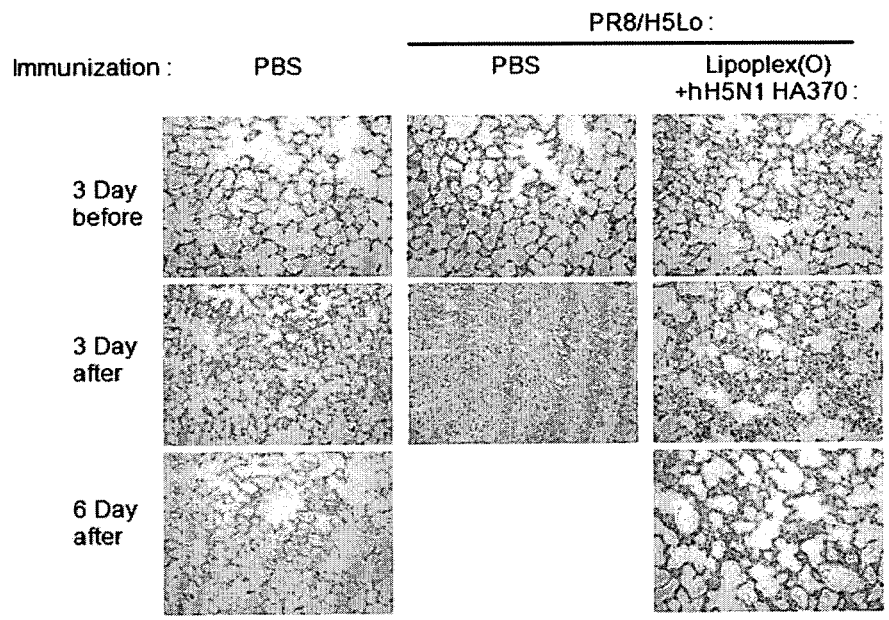
Figure 17D:
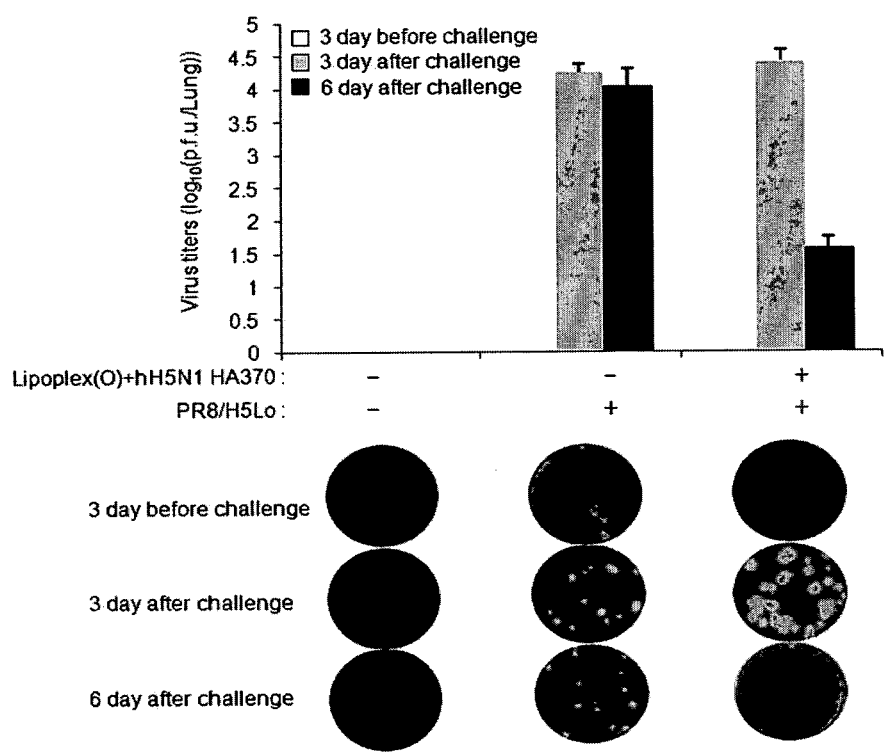

FIG. 17a-17d represent prophylactic efficacy of vaccination by PO-DNA (MB-ODN 4531(O))-peptide (hH5N1 HA370)-DOPE:CHEMS complex in mice challenged with the rH5N1 virus. BALB/c mice were immunized i.p. with PO-DNA (MB-ODN 4531(O))-peptide (hH5N1 HA370)-liposome complex on two occasions at 10 day intervals followed by nasal administration of a 10LD50 rH5N1 virus in two months after the vaccination. FIG. 17a shows that the mice administered with PO-DNA (MB-ODN 4531(O))-peptide (hH5N1 HA370)-liposome complex survived after nasal administration of the 10LD50 rH5N1 virus. FIG. 17b indicates that the mice administered with PO-DNA (MB-ODN 4531(O))-peptide (hH5N1 HA370)-liposome complex restored their weights after nasal administration of the 10LD50 rH5N1 virus. FIG. 17c represent that the mice administered with PO-DNA (MB-ODN 4531(O))-peptide (hH5N1 HA370)-liposome complex had normal lung tissue after nasal administration of the 10LD50 rH5N1 virus. FIG. 17d shows that the viruses in lung tissue viruses were decreased in the mice administered with PO-DNA (MB-ODN 4531(O))-peptide (hH5N1 HA370)-liposome complex in 3 days or 6 days after nasal administration of the 10LD50 rH5N1 virus.

Figure 18A:
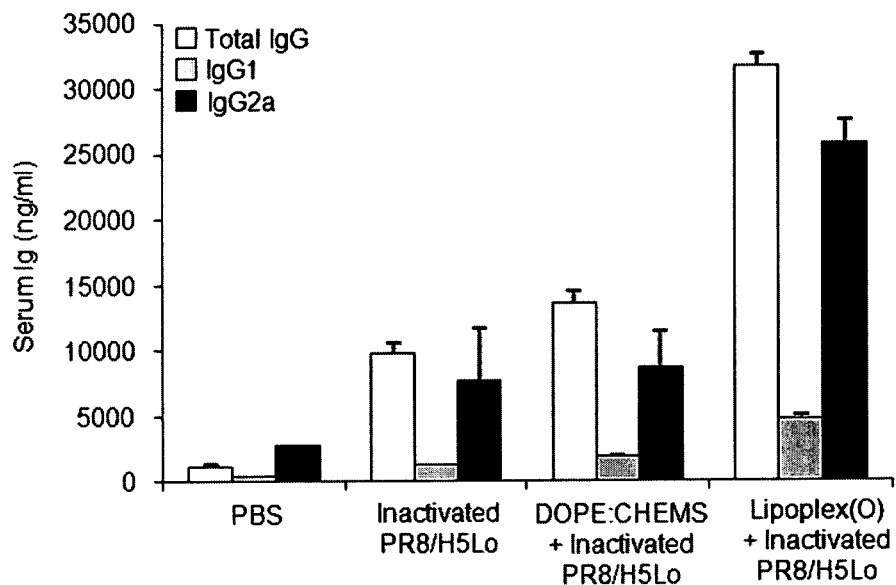
Figure 18B:
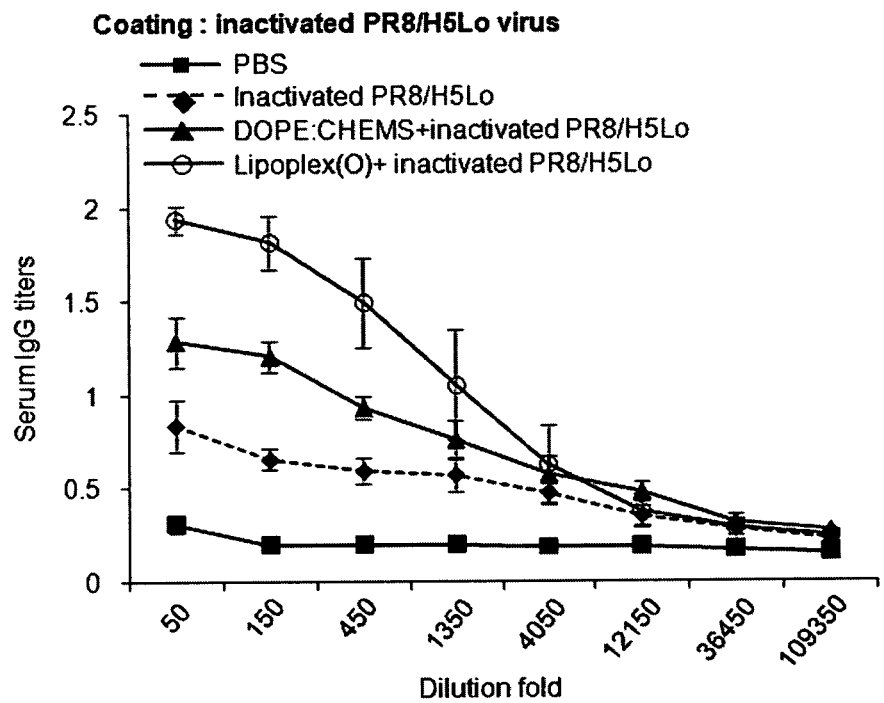

FIG. 18a-18d indicate that the epitope-specific antibody production using PO-DNA (MB-ODN 4531(O))-epitope-DOPE:CHEMS complex is more effective than that using viruses. FIG. 18a shows that the production of total IgG, which bind to virus specifically, and the IgG2a, which is related to Th1 immune response, were increased in mice intraperitoneally administered with a PO-DNA (MB-ODN 4531(O))-UV-inactivated rH5N1 virus-DOPE:CHEMS complex (Lipoplex(O)+inactivated PR8/H5Lo) on three occasions at 10 day intervals. FIG. 18b shows that the titers of total IgG were increased in mice intraperitoneally administered with PO-DNA (MB-ODN 4531(O))-UV-inactivated rH5N1 virus-DOPE:CHEMS complex on three occasions at 10 day intervals. FIG. 18c-18d shows that, in sera vaccinated with using PO-DNA (MB-ODN 4531(O))-epitope (hH5N1 HA233 or hH5N1 HA370)-DOPE:CHEMS complex, the titers of total IgG which binds to each peptide was increased.

Figure 19A:
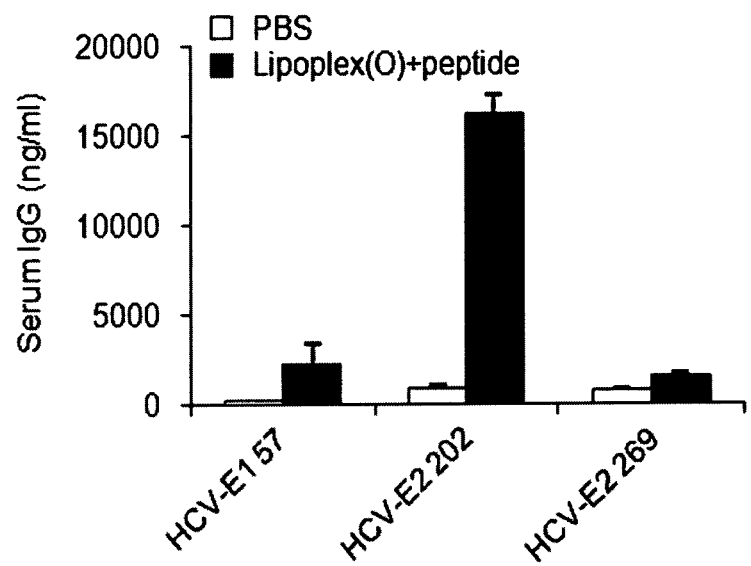
Figure 19B:
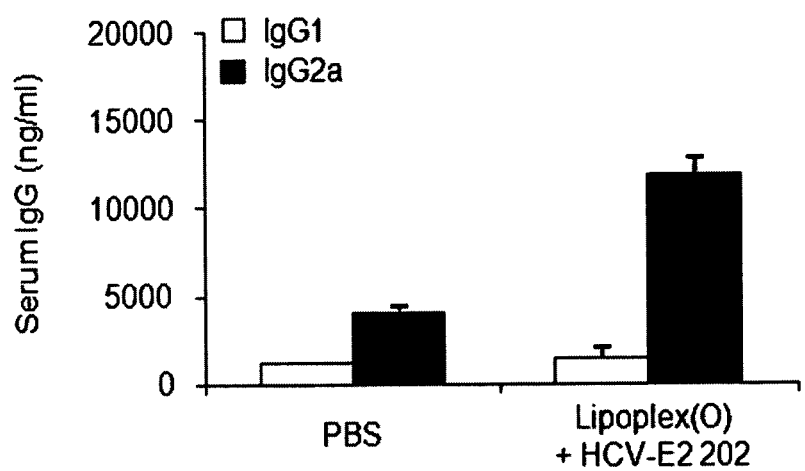
Figure 19C:
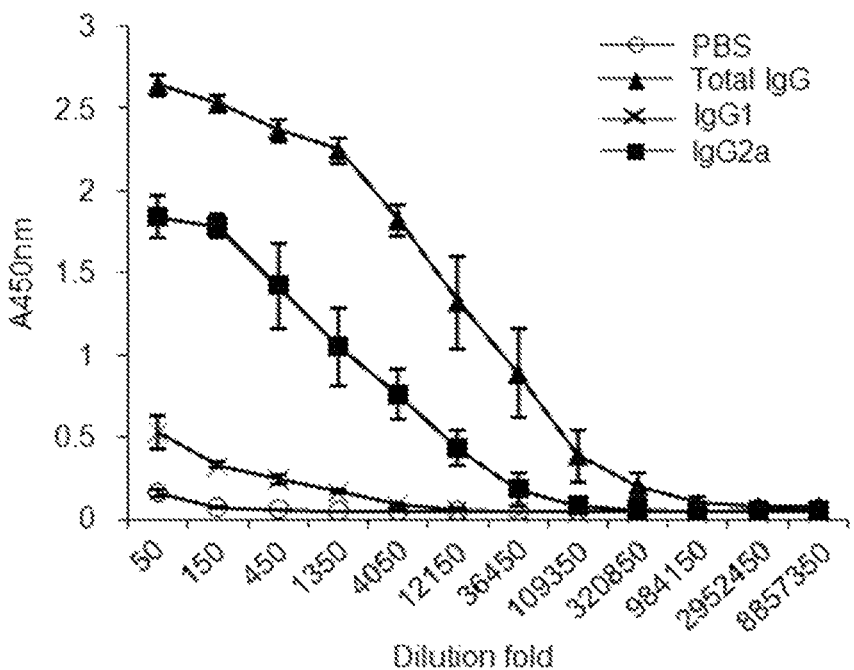
Figure 19D:
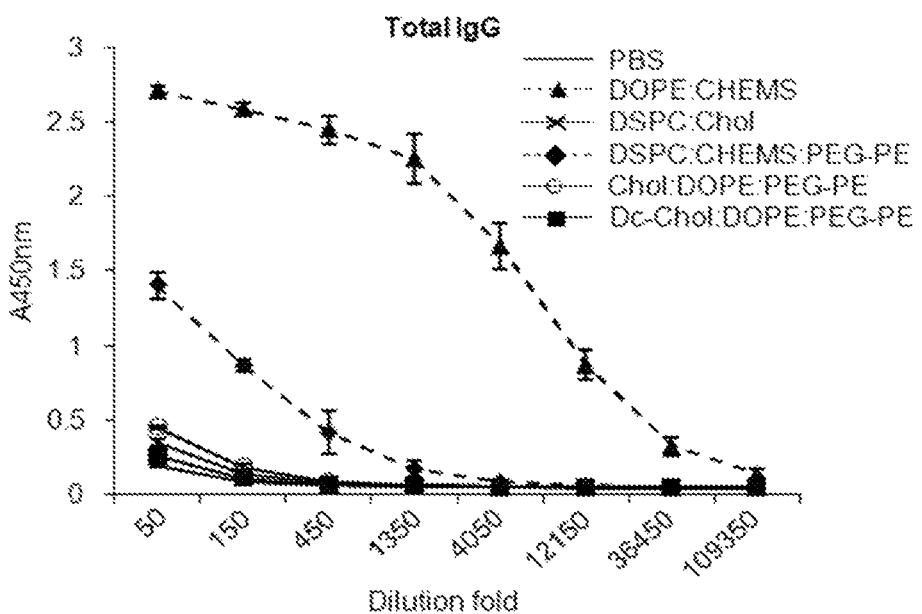

FIG. 19a-19d represent the epitope selection from three candidate epitopes of HCV-E1 protein (Table 10) considering hydrophilicity, hydrophobicity, secondary structure, antigenicity and amphiphilicity for development of a PO-DNA (MB-ODN4531 (O))-peptide-DOPE:CHEMS complex based vaccine. The selected 3 candidate epitopes (HCV-E1 57, HCV-E1 202, HCV-E1 269) were prepared as PO-DNA (MB-ODN4531 (O))-each peptide-liposome complex and then administered to BALB/c mice intraperitoneally on three occasions and the sera were collected. It is confirmed that the production of HCV-E1 57 peptide-specific total IgG (FIG. 19a) was increased. In addition, the amounts of total IgG (FIG. 19a) and the amounts and titers of IgG2a which is related to Th1 immune response (FIGS. 19b and 19c) were increased in sera vaccinated with HCV-E1 202 peptide. Further, the present inventors also collected sera from BALB/c mice intraperitoneally administrated on three occasions with MB-ODN4531 (O) and peptide (HCV-E1 202) complexed with various liposomes. The titer of HCV-E1 202 peptide specific total IgG was highest when the molar ratio of DOPE:CHEMS was 1:1 (FIG. 19d).

Figures 20A, 20B:
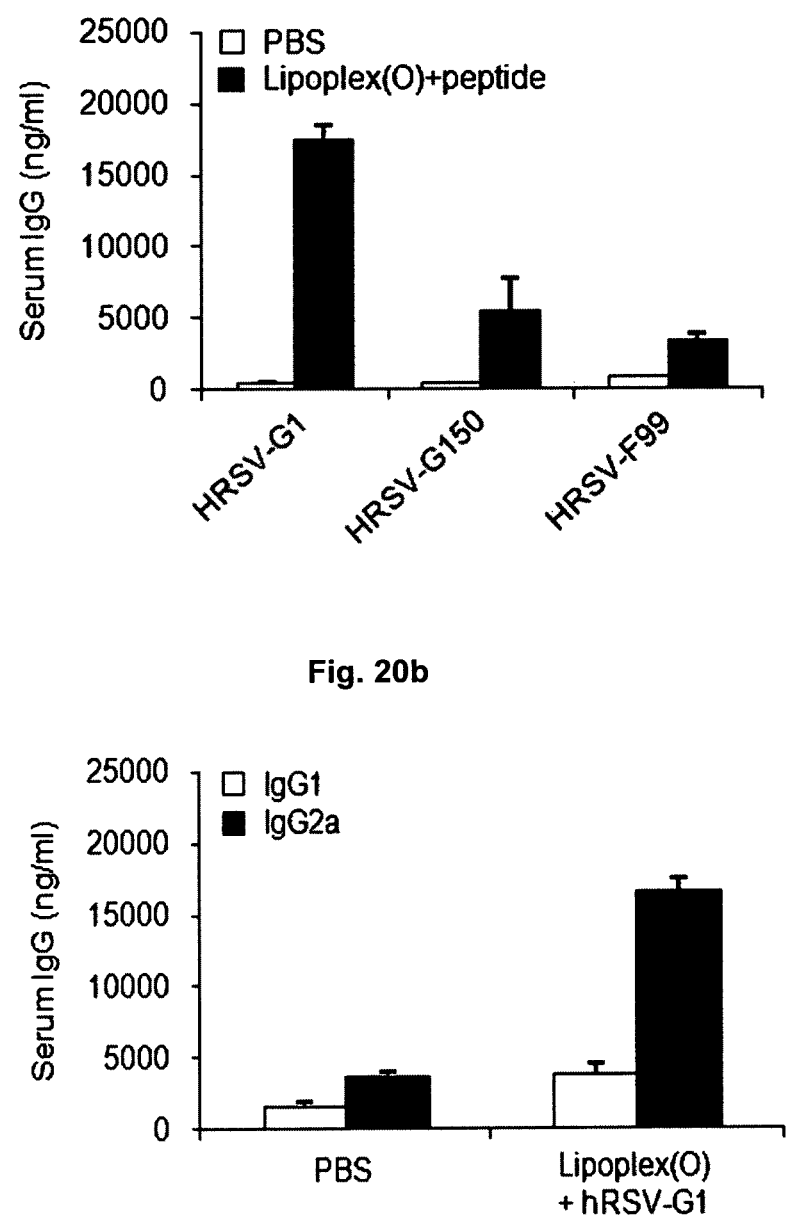
Figure 20C:
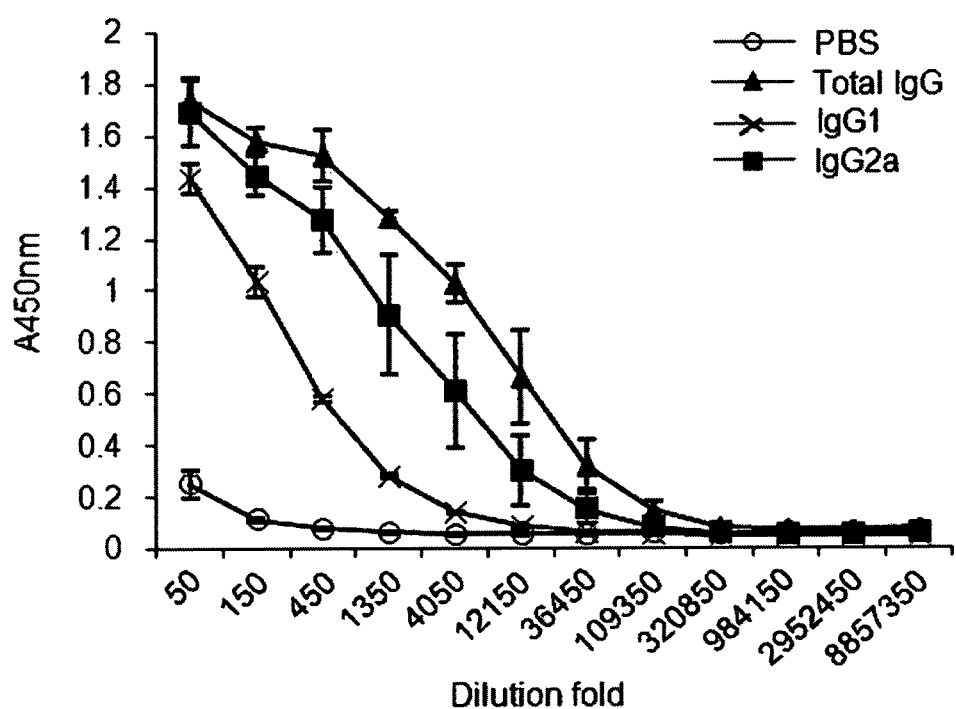
Figure 21A:
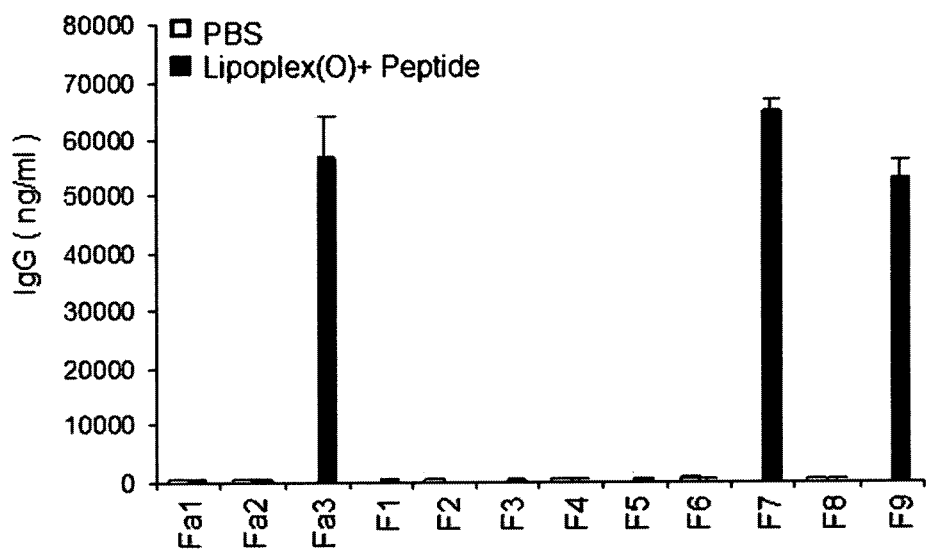
Figure 21B:
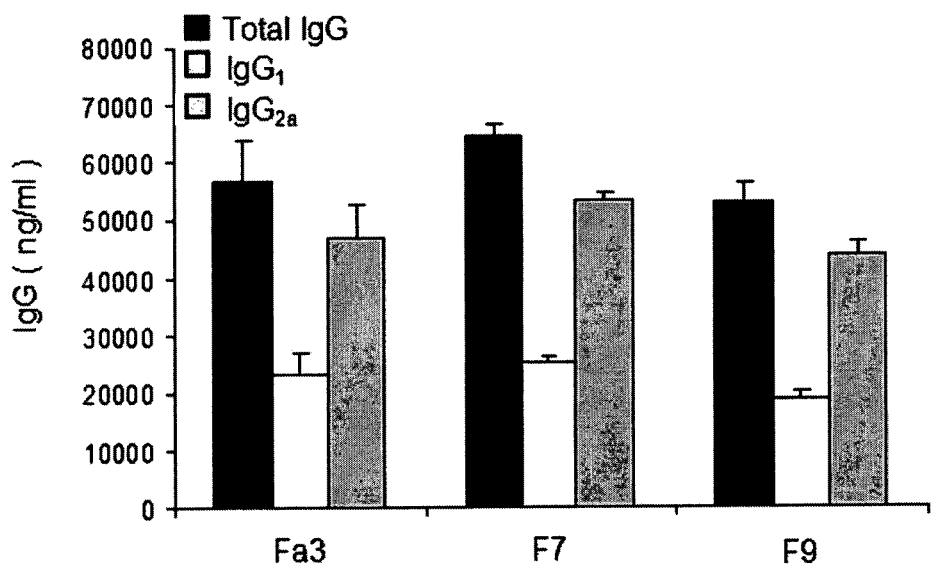
Figure 21C:
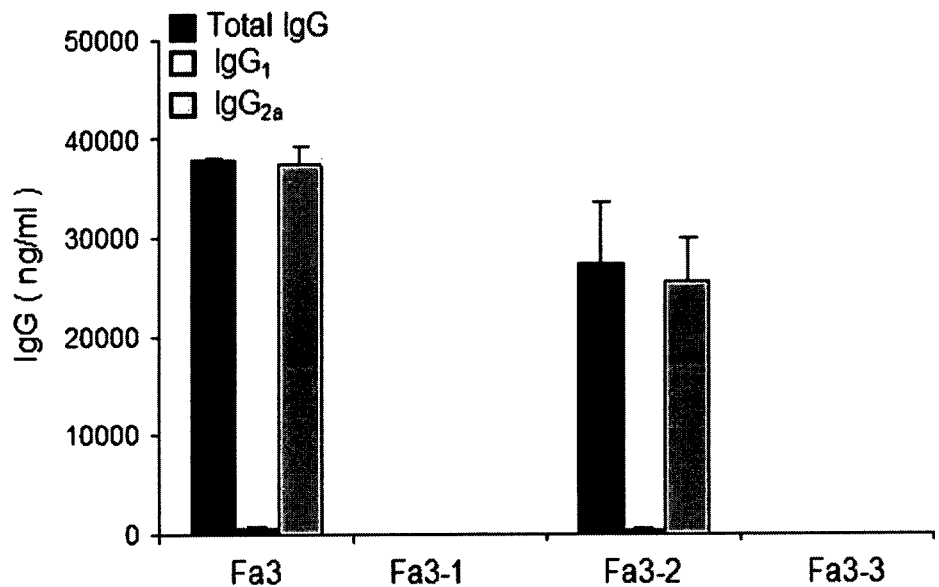
Figure 21D:
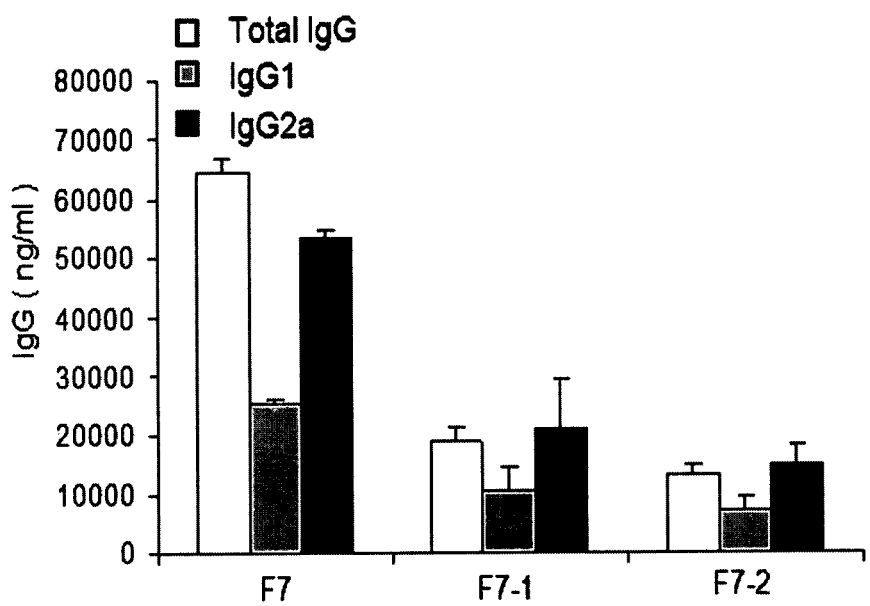

FIG. 20a-20c represent the epitope selection from three candidate epitopes (Table 10) among HSRV (human respiratory syncytial virus) G and F protein considering hydrophilicity, hydrophobicity, secondary structure, antigenicity and amphiphilicity for development of a PO-DNA (MB-ODN4531 (O))-peptide-DOPE:CHEMS complex based vaccine. The selected 3 candidate epitopes (HSRV-G1, HSRV-G150, HSRV-F99) were prepared as MB-ODN4531 (O)-each peptide-liposome complex and then administered to BALB/c mice intraperitoneally on three occasions and the sera were collected. It is confirmed that the production of HSRV-G1 peptide-specific total IgG (FIG. 20a) and IgG2a (FIG. 20b) were increased. In addition, the titer of HSRV-G1 peptide specific total IgG (FIG. 20c) and the production of IgG2a which is related to Th1 immune response (FIGS. 20b and 20c) were increased in sera vaccinated with HSRV-G1 peptide.

FIG. 21a-21d represent the epitope selection from seventeen candidate epitopes (Table 11 and 12) among HSRV (human respiratory syncytial virus) F protein considering hydrophilicity, hydrophobicity, secondary structure, antigenicity and amphiphilicity for development of a PO-DNA-peptide-liposome complex based vaccine. Each of the selected 17 candidate epitopes was prepared as MB-ODN 4531(O)-each peptide-liposome complex and then administered to BALB/c mice intraperitoneally on three or four occasions and the sera were collected. It is confirmed that the production of total IgG (FIGS. 21a, 21b, 21c and 21d) and IgG2a (FIGS. 21b, 21c and 21d) which specifically bind to 4 candidate epitope (HSRV-F3a, HSRV-F3a-2, HSRV-F7, HSRV-F9) peptides were increased.

Figure 22A:
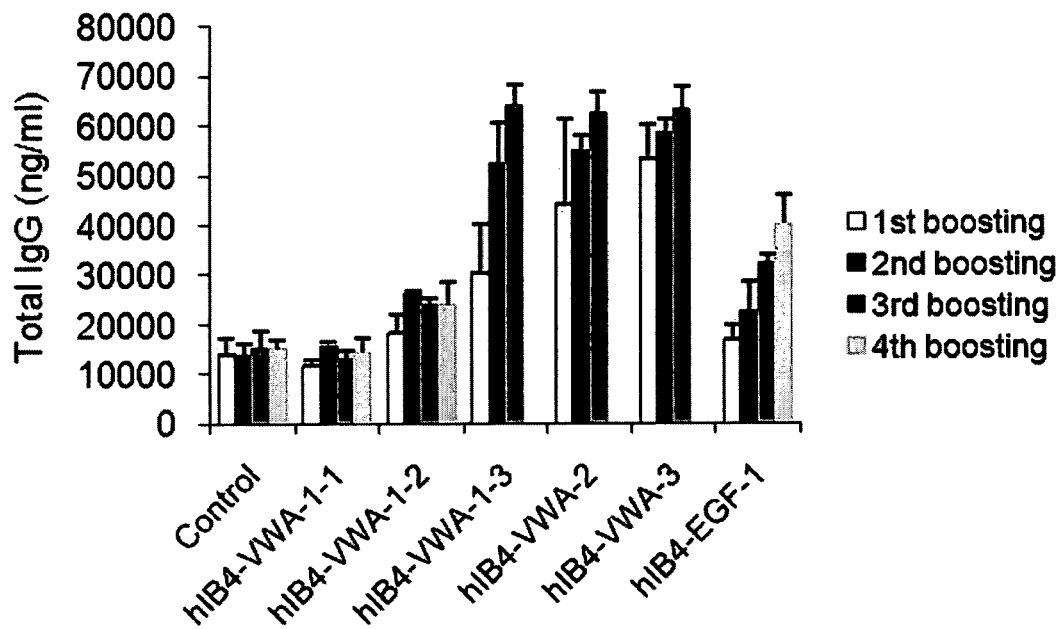
Figure 22B:
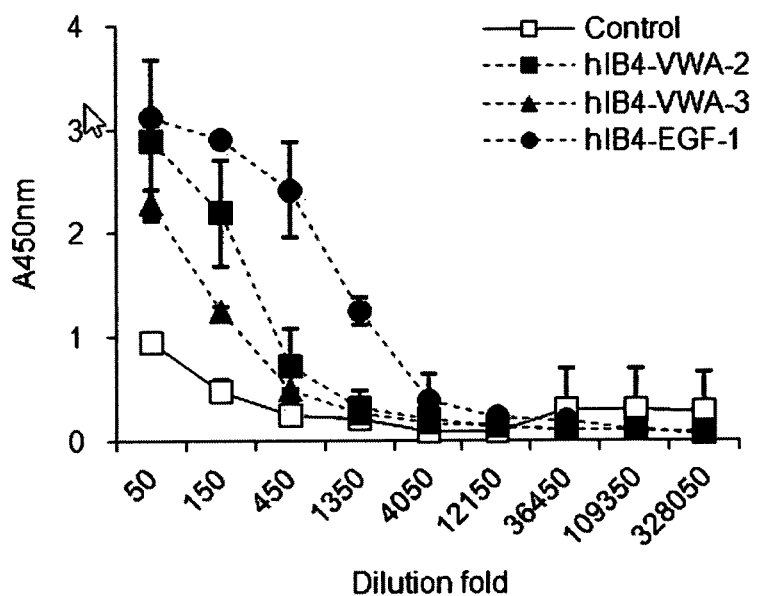

FIG. 22a-22b represent the epitope selection from six candidate epitopes (Table 13) among human integrin β4 (expressed in most carcinoma cells) considering hydrophilicity, hydrophobicity, secondary structure, antigenicity and amphiphilicity for development of a PO-DNA-peptide-liposome complex based vaccine. Each of the selected six candidate epitopes was prepared as MB-ODN 4531 (O)-each peptide-liposome complex and then administered to BALB/c mice intraperitoneally on four occasions and the sera were collected. It is confirmed that the amounts of total IgG (FIG. 22a) and titers of total IgG (FIG. 22b) which specifically bind to 4 candidate epitopes (hIB4-VWA-1-2, hIB4-VWA-1-3, hIB4-VWA-2, hIB4-VWA-3, hIB4-EGF-1) peptides were increased.

Figure 23A:
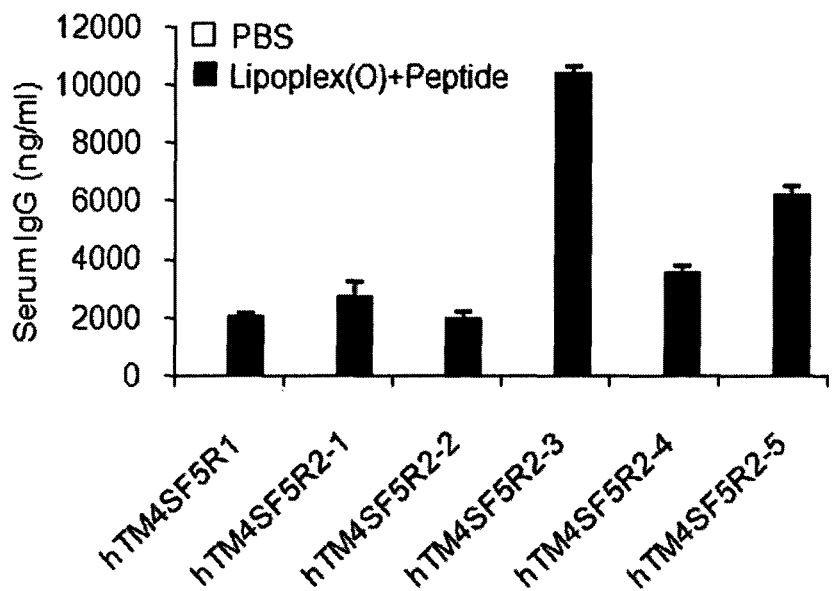
Figure 23B:
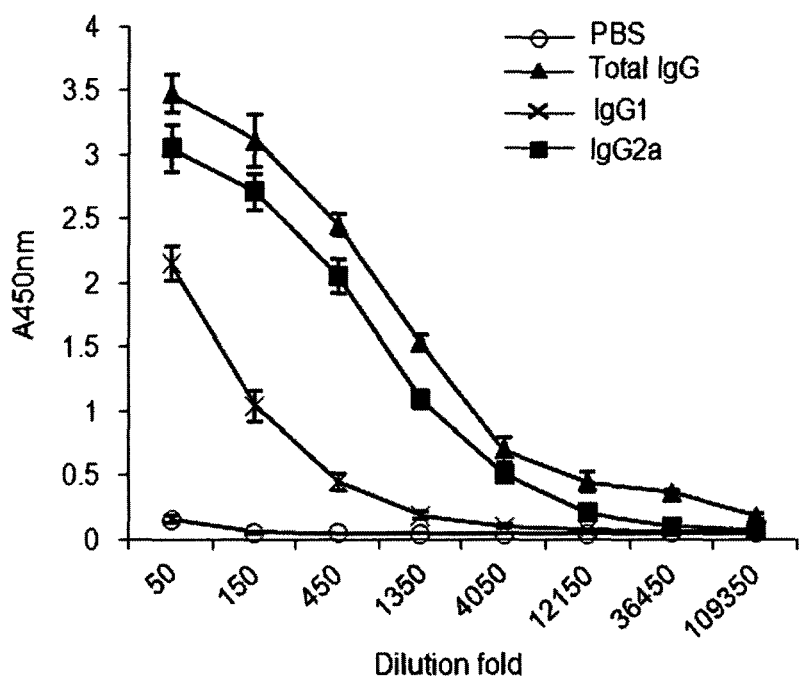
Figure 23C:
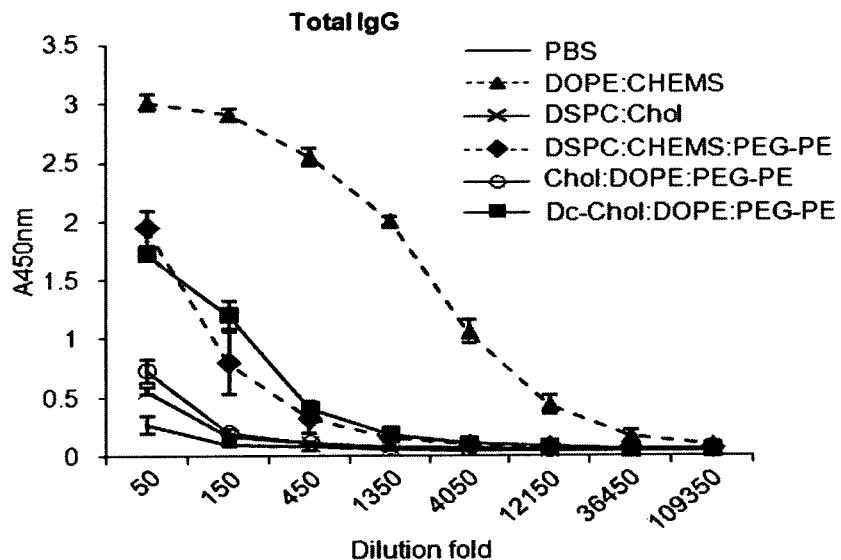
Figure 23D:
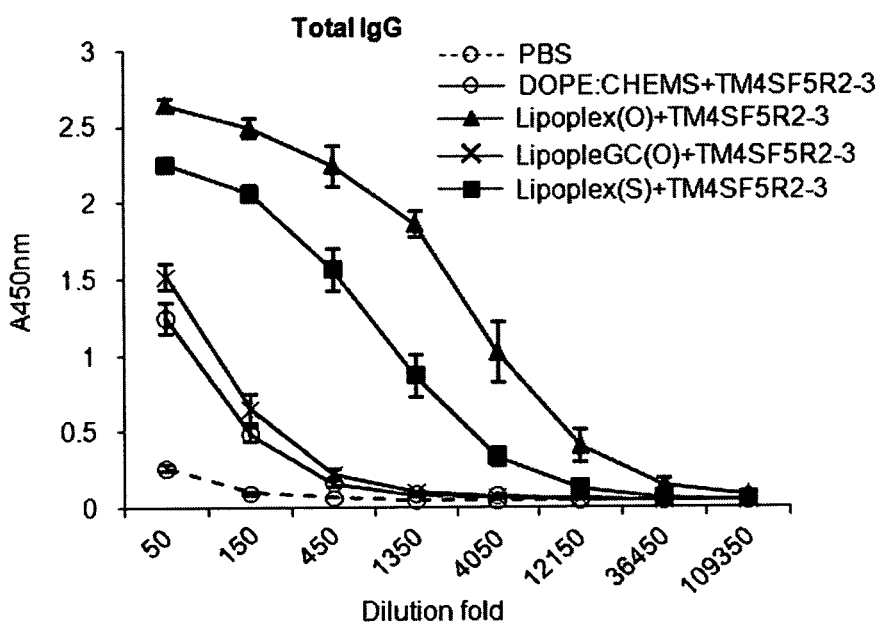
Figure 23E:
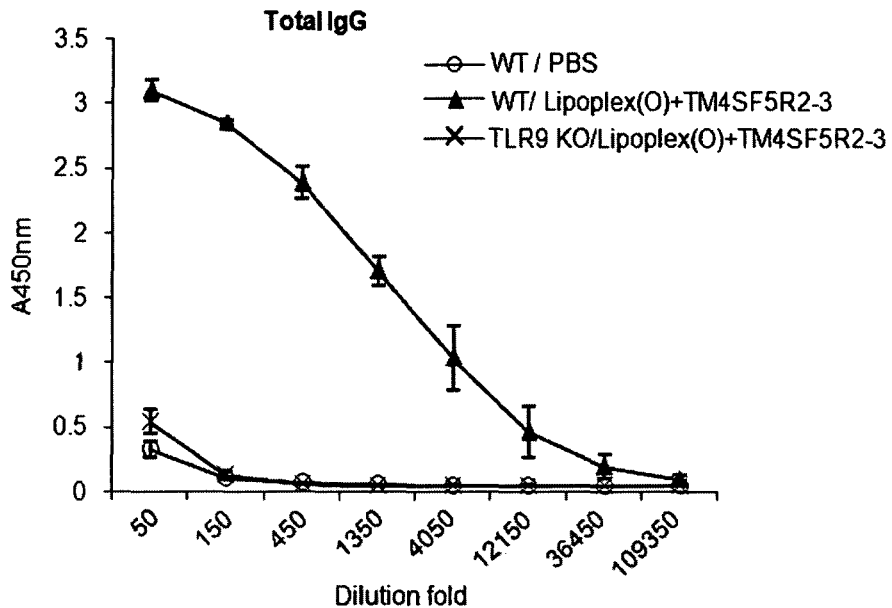
Figure 23F:
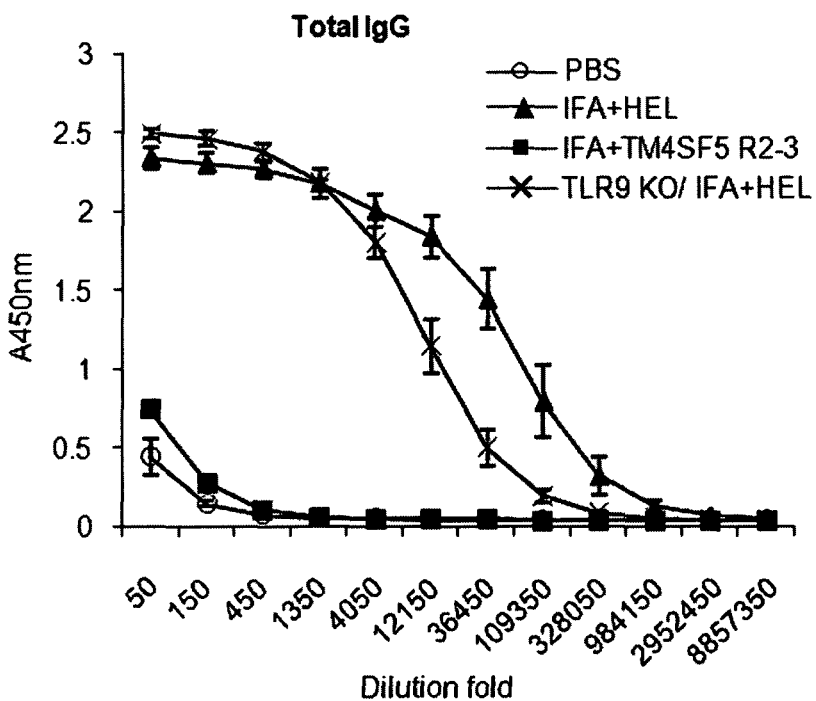

FIG. 23a-23f represent the epitope selection from six candidate epitopes (Table 10) among hTM4SF5 (human tetraspanin transmembrane 4 superfamily member 5) proteins, which is known to be specifically expressed in hepatocarcinoma, considering hydrophilicity, hydrophobicity, secondary structure, antigenicity and amphiphilicity. The selected 6 candidate epitopes (hTM4SF5R1, hTM4SF5R2-1, hTM4SF5R2-2, hTM4SF5R2-3, hTM4SF5R2-4, hTM4SF5R2-5) were prepared as MB-ODN4531 (O)-each peptide-liposome complex and then administered to BALB/c mice intraperitoneally on three occasions and the sera were collected. It is confirmed that the production of hTM4SF5R2-3 and hTM4SF5R2-5 peptide-specific total IgG (FIG. 23a) and IgG2a (FIG. 23b) were increased. In addition, the titer of total IgG (FIG. 23b) and the production of IgG2a which is related to Th1 immune response (FIG. 23b) were increased in sera vaccinated with hTM4SF5R2-3 peptide. Further, the present inventors also collected sera from BALB/c mice intraperitoneally administrated on three occasions with MB-ODN4531 (O) and peptide (hTM4SF5R2-3) complexed with various liposomes. The titer of hTM4SF5R2-3 peptide specific total IgG was highest when the molar ratio of DOPE:CHEMS was 1:1 (FIG. 23c). The present inventors collected sera from the mice administered with hTM4SF5R2-3-CpG-DNA(MB-ODN 4531 (O), MB-ODN 4531GC(O), or MB-ODN 4531(S)) complexed with the liposome (DOPE:CHEMS (1:1)) (FIG. 23*d*). The titer of hTM4SF5R2-3 peptide-specific total IgG was highest in MB-ODN 4531(O). The present inventors collected sera from the TLR9 knockout BALB/c mice administered intraperitoneally with PO-DNA (MB-ODN 4531(O))-hTM4SFR2-3 peptide-DOPE:CHEMS complex on three occasions (FIG. 23*e*-23*f*). TLR9 knockout BALB/c mice did not show any titer of total hTM4SF5R2-3 peptide-specific IgG, which indicated that the antibody production by PO-DNA (MB-ODN 4531(O))-hTM4SFR2-3 peptide-DOPE:CHEMS complex is dependant on TLR9.

Figure 24A:
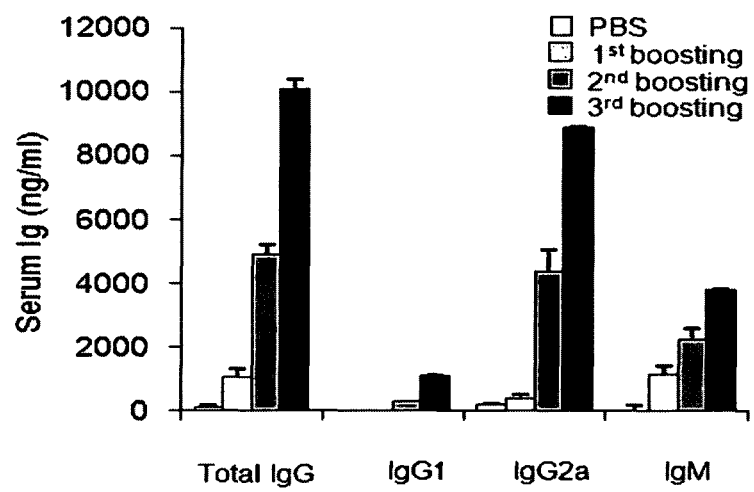
Figure 24B:
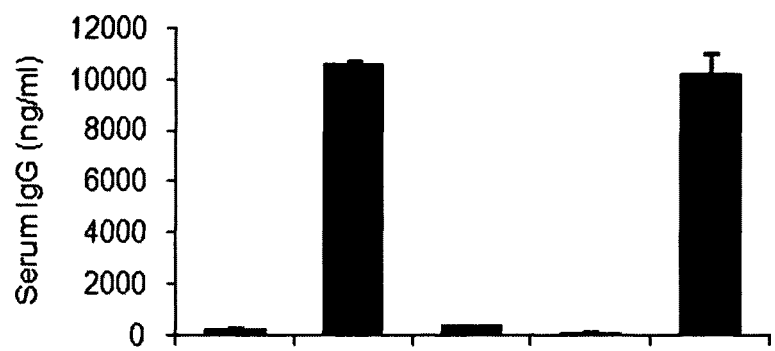

FIG. 24*a*-24*f* represent the effect of MHC class II-mediated presentation and Th1 differentiation on IgG production by immunization with epitope and MB-ODN 4531(O) coencapsulated in DOPE:CHEMS complex. FIG. 24*a* shows the kinetics of IgG production in response to hTM4SF5R2-3 peptide and MB-ODN 4531(O) coencapsulated in DOPE:CHEMS complex. Three BALB/c mice were injected i.p. with hTM4SF5R2-3 peptide and MB-ODN 4531(O) coencapsulated in DOPE:CHEMS complex three times with a 10 day interval. The sera were collected four times i.p. on day −1 relative time of immunization and amounts of the peptide-specific total IgG, IgG1, IgG2a and IgM were assayed by an ELISA. FIG. 24*b* shows the transient depletion of CD4$^+$ cells prevents IgG production by immunization with hTM4SF5R2-3 peptide and MB-ODN 4531(O) coencapsulated in DOPE:CHEMS complex. 100 µg of GK1.5 (anti-CD4 antibody) per mouse was injected four times i.p. on days −3, −1, 1 and 3 relative time of immunization. On day 0, the three mice were injected i.p. with hTM4SF5R2-3 peptide and MB-ODN 4531(O) coencapsulated in DOPE:CHEMS complex (represented as Lipoplex(O)+TM4SF5R2-3) three times with a 10 day interval. The sera were collected and amounts of the peptide-specific total IgG were assayed by an ELISA. Normal IgG was used as control. (FIGS. 24*c* and 24*d*) MHC class II and MHC class II-restricted T cell activation is required for IgG production by immunization with HCVE2-202 peptide and MB-ODN 4531(O) coencapsulated in DOPE:CHEMS complex. C57BL/6 mice, C57BL/6 MHC class knockout mice (MHC-II KO) (FIG. 24*c*), or C57BL/60T-II transgenic mice(OT-II TG) (FIG. 24*d*) (n=3) were injected i.p. with 50 µg of HCVE2-202 peptide and 50 µg of MB-ODN 4531(O) coencapsulated in DOPE:CHEMS complex (represented as Lipoplex (O)+HCVE2-202) on three occasions at 10 day intervals. The sera were collected and amounts of HCVE2-202 peptide-specific total IgG, IgG1, IgG2a were assayed by an ELISA. (FIGS. 24*e* and 24*f*) STAT4 but not STAT6 is required for IgG production by immunization with 50 µg of hTM4SF5R2-3 peptide and 50 µg of MB-ODN 4531(O) coencapsulated in DOPE:CHEMS complex. BALB/c mice, BALB/c STAT4 knockout mice (STAT4 KO) (FIG. 24*e*), or BALB/c STAT6 knockout mice (STAT6KO) (FIG. 24*f*) (n=3) were injected i.p. with 50 µg of hTM4SF5R2-3 peptide and 50 µg of MB-ODN 4531(O) coencapsulated in DOPE:CHEMS (1:1 ratio) complex (represented as Lipoplex(O)+TM4SF5R2-3) on three occasions at 10 day intervals. The sera were collected and amounts of hTM4SF5 R2-3 peptide-specific total IgG, IgG1, IgG2a were assayed by an ELISA. These experiments were performed 2 or 3 times with similar results.

Figure 25A:
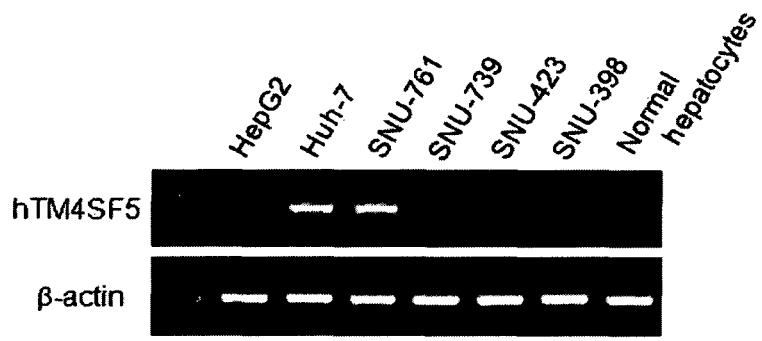
Figure 25B:
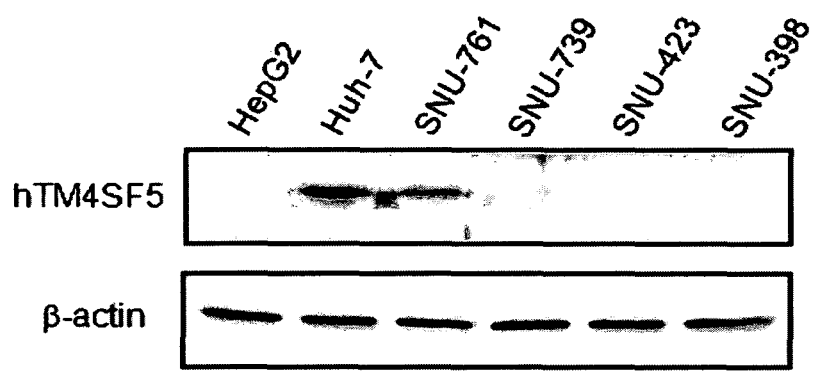
Figure 25C:
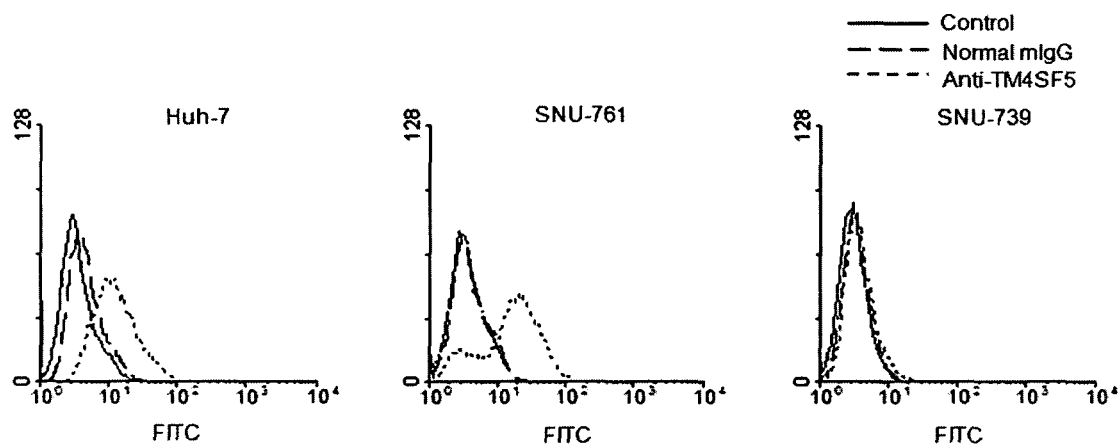
Figure 25D:
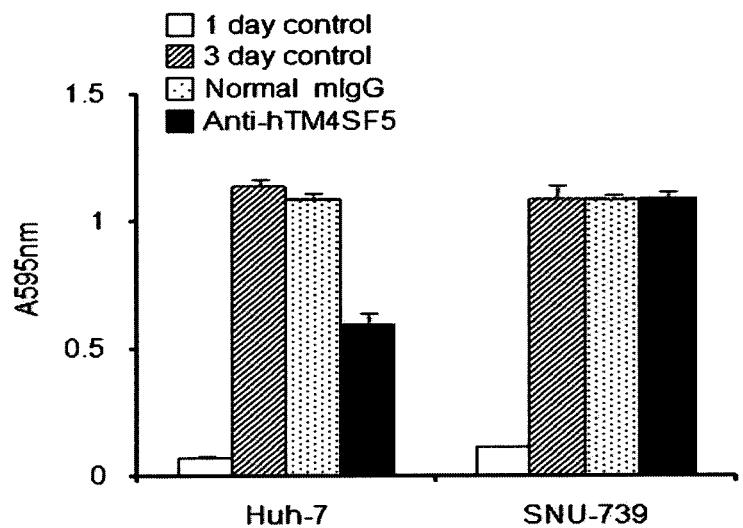
Figure 25E:
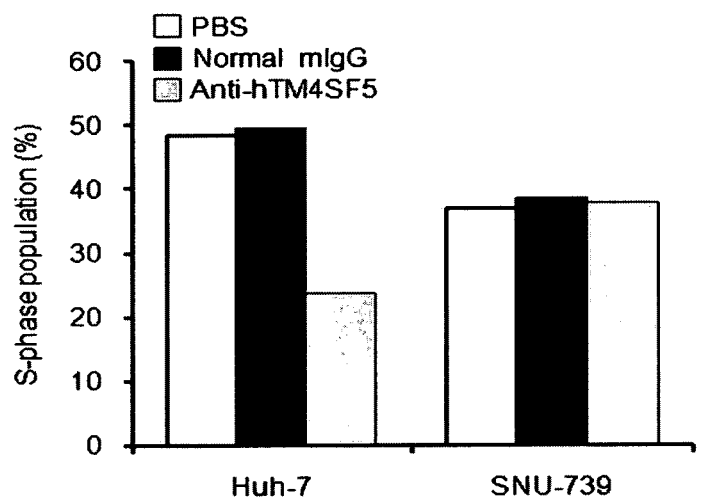
Figure 25F:
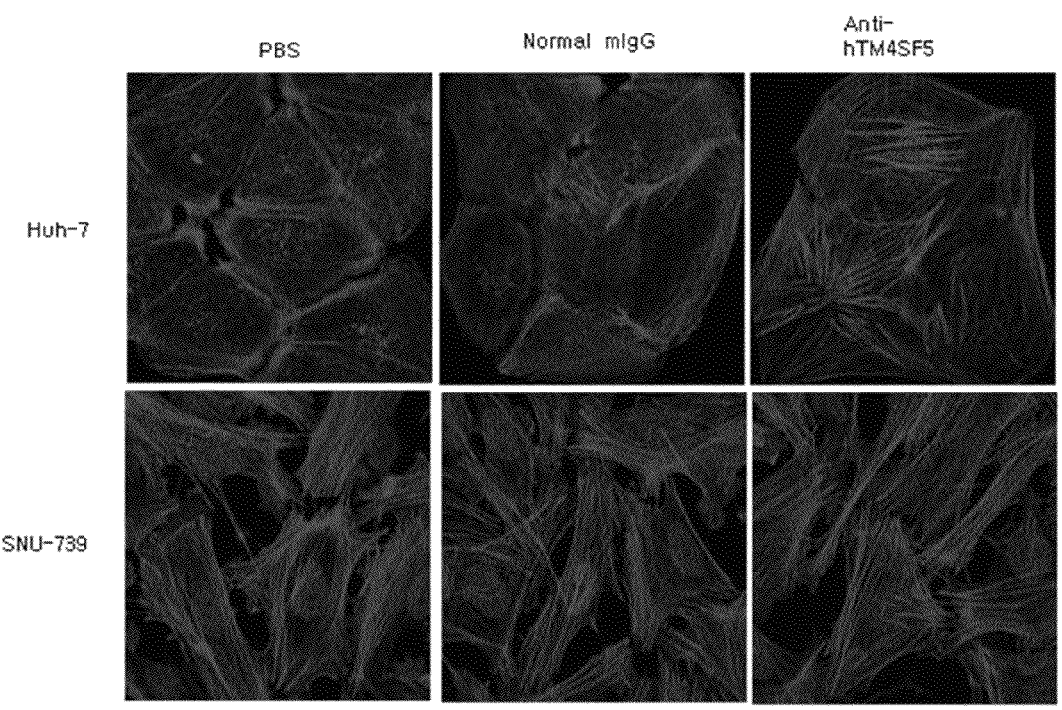

FIGS. 25*a*-25*f* represent that the hTM4SF5R2-3 peptide-specific antibody recognizes the TM4SF5 protein of hepatocarcinoma cells and regulates the function of hepatocarcinoma cells. The expression of TM4SF5 was observed in Huh-7 and SNU-761 by RT-PCR (FIG. 25*a*). The expression of TM4SF5 was observed in Huh-7 and SNU-761 by Western blotting (FIG. 25*b*). It is confirmed by FACS that the hTM4SF5R2-3 peptide-specific monoclonal antibody recognizes the TM4SF5 protein of Huh-7 and SNU-761 cells (FIG. 25*c*). FIG. 25*d* shows through MTT assay that the growth of the Huh-7 cell expressing TM4SF5 was inhibited when the hepatocarcinoma cells were treated with the hTM4SF5R2-3 peptide-specific monoclonal antibody. FIG. 25*e* shows that the S-phase of the Huh-7 cell was decreased by treatment of the hTM4SF5R2-3 peptide-specific monoclonal antibody. FIG. 25*f* represent that when the hepatocarcinoma cells expressing TM4SF5 (Huh-7) were treated with the hTM4SF5R2-3 peptide-specific monoclonal antibody, the actin has a distinct outline of stress fiber supporting an overspread polygonal shape as in the cell which does not express TM4SF5. While an abnormal bundling of the actin is known to be observed in the hepatocarcinoma cell expressing TM4SF5, the stress fiber with distinct outline supporting an overspread polygonal shape is detected in the cell that does not express TM4SF5 by actin staining. The TM4SF5 expressing cells (Huh-7) treated with anti-hTM4SF5R2-3 antibodies strongly induced the distinct outlined stress fiber similar to the actin of the cell which does not express TM4SF5. These results indicate that the antibody is targeted to the hTM4SF5 expressing cell.

Figure 26A:
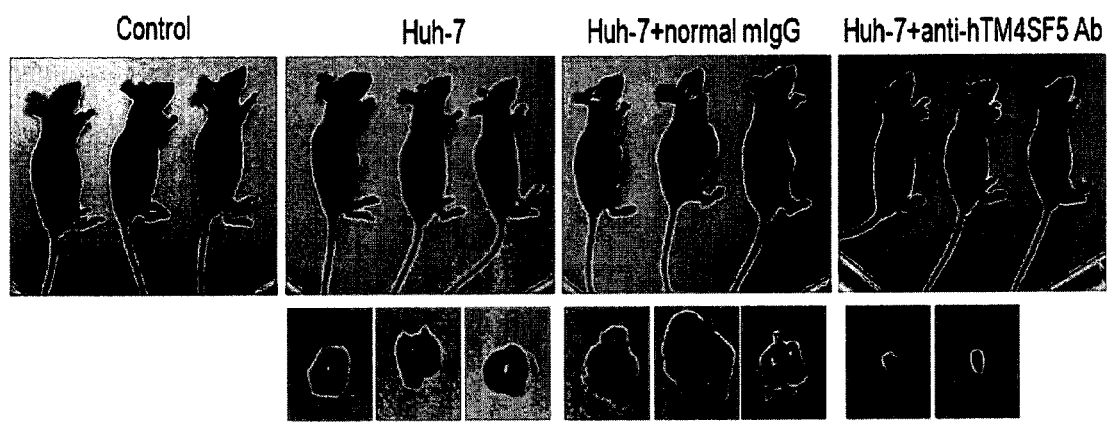
Figure 26B:
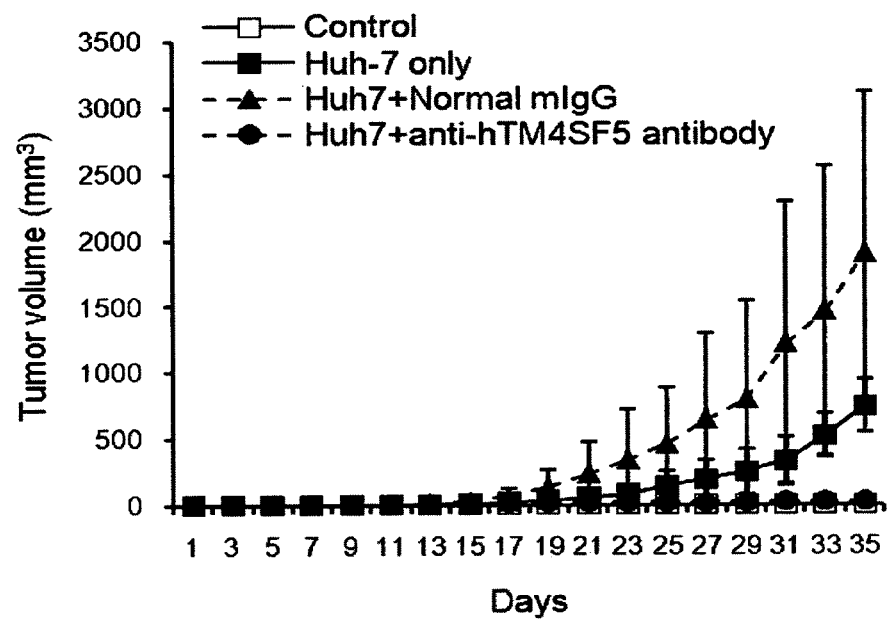

FIGS. 26*a*-26*b* represent that the hTM4SF5R2-3 peptide-specific antibody inhibits human hepatocarcinoma cell growth in vivo. Athymic mice nude mice harboring Huh-7 cells xenografts were treated with 10 mg/Kg hTM4SF5R2-3 peptide-specific antibody delivered five times with a three day intervals on day 7 following tumor implantation (FIG. 26*a*). Mice were sacrificed when the tumor size reached a volume ±2000 mm$^3$ and the weight of tumors were assessed (FIG. 26*b*).

Figure 27B:
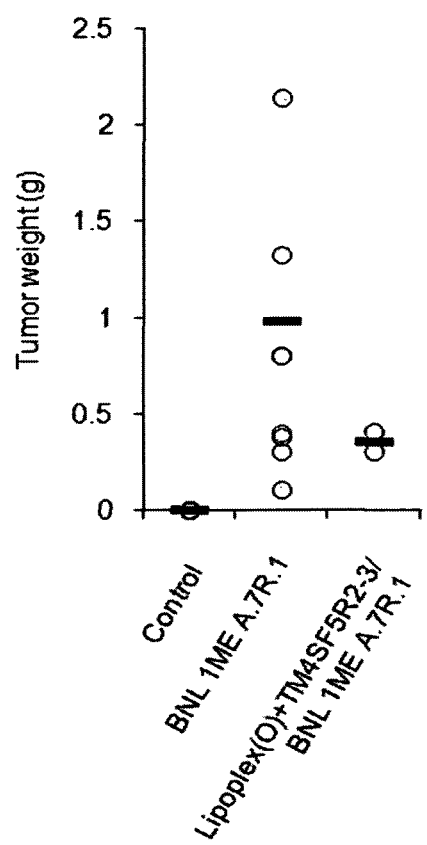

FIG. 27*a*-27*b* represent prophylactic efficacy of vaccination by PO-DNA (MB-ODN 4531(O))-hTM4SF5R2-3 peptide-DOPE:CHEMS complex in allograft hepatocarcinoma model challenged with BNL-HCC cells. BALB/c mice were immunized i.p. with PO-DNA (MB-ODN 4531(O))-hTM4SF5R2-3 peptide-liposome complex on three occasions at 10 day intervals followed by inoculation s.c. in the dorsal right flank with 5×10$^6$ BNL-HCC cells containing 50% Matrigel. The mice were sacrificed 7 weeks after the tumor cell implantation, and the weight of tumors were assessed.

DETAILED DESCRIPTION OF THIS INVENTION

In one aspect of this invention, there is provided a composition for enhancing an immune response comprising as an active ingredient (a) an immunostimulatory oligonucleotide and (b) an epitope encapsulated in a liposome containing anionic surfactants and neutral phospholipids. The present inventors have made intensive studies to develop a novel immunoadjuvant capable of preventing and treating various cancers and infectious diseases. As results, they have identified the peptide epitopes of protein antigens and discovered that epitopes and oligonucleotides encapsulated in liposomes of specific compositions give greatly enhanced immunostimulatory activities.

The term "anionic surfactants" as used herein, refers to reagents composed of amphipathic molecules having both hydrophobic and hydrophilic portion and negatively charged over the whole molecules. Preferably, anionic surfactants of the present invention include, but not limited to, phosphatidylglycerol, cardiolipin, phosphatidylserine, diacylphosphatidylserine, dicetylphosphate, phosphatidic acid, diacylphosphatidic acid, oleic acid, N-dodecanoyl phosphatidylethanoloamine, NSPE (N-succinyl phosphatidylethanolamine, NGPE (N-glutaryl phosphatidylethanolamine), LPG (lysylphosphatidylglycerol) and CHEMS (cholesterylhemisuccinate). More preferably, the anionic surfactant of the present invention is CHEMS.

The term "neutral phospholipids" as used herein, refers to phospholipids with zero net charge over the whole molecules even a part of atoms are charged like zwitterions, as well as those in which each atom has no charge. Preferably, neutral phospholipids of the present invention include, but not limited to, phosphatidylcholine, DPPC (dipalmitoyl phosphatidyl choline), DSPC (1,2-distearoyl-sn-glycero-3-phosphocholine), DMPC (dimyristoylphosphatidylcholine), cholesterl, PEG-PE (polyethylene glycolphosphatidyl ethanolamine), DOPC (dioleoyl phosphatidyl choline) and DOPE (dioleyl phosphatidyl ethanolamine). More preferably, the neutral phospholipid of the present invention is DOPE.

The term "liposome" as used herein refers to lipid carriers prepared by forming a lipid bilayer. The liposome is generally biocompatible and capable of passing through hydrophobic plasma membranes due to its amphiphilicity. The diameter of liposomes is generally 20-2000 nm, but not limited to, depending on preparation methods and lengths of delivered nucleotides.

According to a preferred embodiment, the liposome of this invention is a mixture of CHEMS and DOPE.

The molar ratio of DOPE:CHEMS of the present invention is preferably 7:3-3:7, more preferably 4.5:5.5-5.5:4.5, and most preferably 5.0:5.0.

The preparation of liposomes of the present invention may be performed through various methods known to those skilled in the art, and preferably by organic solution-mixing methods or detergent mixing methods (U.S. Pat. No. 5,705,385; U.S. Ser. No. 08/660,025). More preferably, liposomes may be made by mixing DOPE and CHEMS and evaporated with nitrogen gas to be a form of solvent-free lipid films, and dissolved in alcohol solution and finally mixed with water-soluble nucleotide mixture.

In case of preparing the liposomes of the present invention through mixing organic solvent, said organic solvent includes chloroform, methanol, ethanol, n-propanol or butanol. Preferably, said organic solvent is ethanol.

The term "encapsulation" as used herein refers to enclosure of delivered materials into a relatively stable shell for effectively delivering in vivo.

The term "immunostimulatory" as used herein, refers to inducing initial immune response or increasing existing immune response to antigen by measurable degrees.

The immunostimulatory oligonucleotide of the present invention comprises any of immunostimulatory oligonucleotide known to those skilled in the art. For example, said immunostimulatory oligonucleotide may be hairpin structure-forming palindrome, CpG motif, CpT motif, multiple G domain or other known ISS (immunostimulatory sequence). For example, the immunostimulatory oligonucleotide of the present invention comprises oligonucleotides disclosed in US20080045473, WO 2006/063152 or WO 1998/18810.

Said CpG oligonucleotide includes those developed by the present inventors disclosed in WO 2006/080596. For example, the CpG oligonucleotide represented by the following formula may be used: HKCGTTCRTGCSGM (wherein R is A or G; S is C or G; H is A, T or C; K is G or T; M is C or A).

Immunostimulatory oligonucleotides of the present invention include natural-occurring nucleotides, a backbone-modified nucleotides (e.g., peptide nucleic acid (PNA) (M. Egholm et al. *Nature,* 365:566-568 (1993)), phosphorothioate DNA, phosphorodithioate DNA, phosphoroamidate DNA, amide-linked DNA, MMI-linked DNA, 2'-O-methyl RNA, alpha-DNA and methyl phosphonate DNA), sugar-modified nucleotides (e.g., 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA and anhydrohexytol DNA) and base-modified nucleotides (e.g., C-5 substituted pyrimidine (substitution group includes fluoro-, bromo-, chloro-, iodo-, methyl-, ethyl-, vinyl-, formyl-, ethynyl-, propynyl-, alkynyl-, thiazoryl-, imidazoryl- and pyridyl), 7-deazapurine with C-7 substitution group (substitution group includes fluoro-, bromo-, chloro-, iodo-, methyl-, ethyl-, vinyl-, formyl-, alkynyl, alkenyl, thiazoryl-, imidazoryl- and pyridyl), inosine and diaminopurine). Preferably, oligonucleotides of the present invention are natural-occurring nucleotides.

According to a preferred embodiment, the immunostimulatory oligonucleotide of this invention has a phosphodiester backbone or a phosphothioate backbone.

The length of the immunostimulatory oligonucleotides of the present invention is, but not limited to, preferably 8-100 nucleotides, more preferably 15-50 nucleotides, and most preferably 13-25 nucleotides.

Preferably, the immunostimulatory oligonucleotide of this invention is selected from the group consisting of SEQ ID NO:14 to SEQ ID NO:18. More preferably, the immunostimulatory oligonucleotide of this invention is SEQ ID NO:14.

The present inventors' previous experimental analysis verified that the potential CpG-DNA originated from the *Mycobacterium bovis* genomic DNA exerted effects as a Th1-responsive adjuvant and that it activated the transcription factor NF-κB (31).

In particular, the oligonucleotides of the present invention are MB-ODN 4531, the 20 bp-oligonucleotide at the position 4531 on the *Mycobacterium bovis* genomic DNA (SEQ ID NO:14), MB-ODN 4531(GCO) in which one of CG dinucleotides on the MB-ODN 4531 is substituted with a GC dinucleotide (SEQ ID NO:15), MB-ODN 4531(S)T13 in which 7 bases of the 3'-end of the MB-ODN 4531 are deleted and bridging oxygen atoms in the backbone is substituted with sulfur atoms (SEQ ID NO: 16), the MB-ODN 4531(S) CT oligonucleotide in which one of CG dinucleotides is substituted with a CT dinucleotide and bridging oxygen atoms in the backbone is substituted with sulfur atoms (SEQ ID NO:17) and the MB-ODN 4531(S)CS oligonucleotide in which it has a complementary sequence to MB-ODN 4531 and bridging oxygen atoms in the backbone is substituted with sulfur atoms (SEQ ID NO: 18). The experimental analysis of the present inventors has revealed that the administration of the MB-ODN 4531 oligonucleotide/peptide/liposome complex induced the highest levels of the total IgG among all complexes each having different oligonucleotide.

The term "epitope" as used herein refers to the portion of an antigen that interacts with an antibody. More specifically, the term epitope includes any protein determinant capable of specific binding to an immunoglobulin or T-cell receptor. Also, the epitope of the present invention includes any of molecules or materials capable of enhancing immune responses. For example, the epitope of the present invention includes, but not limited to, a peptide, a nucleic acid encoding said peptide and a glycoprotein.

The term "peptide" as used herein refers to a linear molecule formed by peptide bonds between amino acid residues and the term "peptide epitope" refers to a peptide comprising an epitope capable of inducing specific responses of B cells and/or T cells.

The length of the peptide epitope of the present invention is, but not limited to, preferably 7-30 amino acids, more preferably 10-25 amino acids, most preferably 10-17 amino acids.

According to a preferred embodiment, the epitope of this invention is a peptide epitope having the amino acid sequence selected from the group consisting of SEQ ID NO:1 to SEQ ID NO:13 and SEQ ID NO:19 to SEQ ID NO:46.

The present inventors synthesized peptides originated from the HA protein of an avian influenza A virus, the HA protein of an swine influenza A virus, the HA protein of H1N1 influenza A viruses, the HA protein of H7 influenza A viruses, the HA protein of H9 influenza A viruses, hTM4SF5 (human tetraspanin transmembrane 4 superfamily member 5) protein of a hepatocarcinoma, human integrin (34 (hIB4), an envelope protein of a hepatitis C virus, attachment (G) glycoprotein of RSV (respiratory syncytial virus) (HRSV-G), and the fusion protein of RSV (HRSV-F). And then SEQ ID NO: 1 to SEQ ID NO: 13 and SEQ ID NO: 19 to SEQ ID NO: 46 were obtained by selecting peptides increasing immune responses when administered. Accordingly, the peptide comprising any amino acid sequence of SEQ ID NO: 1 to SEQ ID NO: 9 and SEQ ID NO: 19 to SEQ ID NO: 37 has an immunostimulatory effect for an influenza A virus, the peptide comprising the amino acid sequence of SEQ ID NO: 10 or SEQ ID NO: 11 has an immunostimulatory effect for a hepatocarcinoma, the peptide comprising the amino acid sequence of SEQ ID NO: 42 to SEQ ID NO 46 has an immunostimulatory effect for human integrin β4, the peptide comprising the amino acid sequence of SEQ ID NO: 12 has an immunostimulatory effect for a hepatitis C virus, and the peptide comprising the amino acid sequence of SEQ ID NO: 13 and SEQ ID NO: 38 to SEQ ID NO 41 has an immunostimulatory effect for a RSV.

The composition of the present invention may contain other drugs or immunoadjuvants to provide additional immunostimulatory effects. The types of the immunoadjuvant are known to those skilled in the art (Vaccine Design—The Subunit and Adjuvant Approach, 1995, Pharmaceutical Biotechnology, Volume 6, Eds. Powell, M. F., and Newman, M. J., Plenum Press, New York and London, ISBN 0-306-44867-X). Preferably the immunoadjuvant of the present invention includes aluminium salts or calcium salts (e.g., hydroxide or phosphate).

The examples of the preferred immunoadjuvant are as follows, but not limited to: aluminium salt, calcium salt (e.g., hydroxide or phosphate), granular carrier (WO 96/33739) like oil-in-water emulsion (WO 95/17210, EP 0 399 843) or liposome, immunologically active saponin extract derived from Quillaja Saponaria Molina (e.g., Quil A), 3 De-O-acylated monophosphoryl lipid A, muramyl dipeptide, 3D-MPL (3-O-deacylated monophosphoryl lipid A).

Examples of conditions or diseases for which the composition of the present invention may be used as treatments include, but are not limited to:

(i) cancers (e.g., gastric cancer, lung cancer, breast cancer, ovarian cancer, liver cancer, bronchial cancer, nasopharyngeal cancer, Laryngeal cancer, pancreatic cancer, bladder cancer, colorectal cancer, colon cancer cervical cancer, brain cancer, prostate cancer, bone cancer, skin cancer, thyroid cancer, parathyroid cancer and ureter cancer);

(ii) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus, including H5N1 avian flu virus), a paramyxovirus (e.g., 5-parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(iii) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(iv) other infectious diseases, such chlamydia, fungal diseases including but not limited to candidiasis, aspergillosis, histoplasmosis, cryptococcal meningitis, or parasitic diseases including but not limited to malaria, pneumocystis camii pneumonia, leishmaniasis, cryptosporidiosis, toxoplasmosis, and trypanosome infection;

(v) $T_{H2}$-mediated atopic diseases, such as atopic dermatitis or eczema, eosinophilia, asthma, allergy, allergic rhinitis, and Ommen's syndrome;

(vi) certain autoimmune diseases such as alopecia greata, ankylosing spondylitis, antiphospholipid syndrome, autoimmune Addison's disease, Autoimmune adrenalitis, autoimmune hemolytic anemia, autoimmune hepatitis, autoimmune oophoritis and orchitis, autoimmune thrombocytopenia, Behset disease, bullous pemphigoid, cardiomyopathy, celiac sprue-dermatitis, chronic fatigue immune dysfunction syndrome, Chronic inflammatory demy elinating polyneuropathy, Churg-Strauss syndrome, cicatrical pemphigoid, CREST syndrome, cold haemagglutinin disease, Crohn's disease, discoid lupus erythematosis, essential mixed cryoglobulinemia, Fibromyalgia-Fibromyositis, glomerulonephritis, Graves disease, Guillain-Barre syndrome Hashimotos thyroiditis, idiopathic pulmonary fibrosis, Idiopathic thrombocytopenic purpuras, IgA neuropathy, Juvenile arthritis in ulcerative colitis, lichen planus, lupus erythematosus, Meniere's disease, mixed connective tissue disease, multiple sclerosis, type I or immune-mediated diabetes mellitus, myasthenia gravis, pemphigus vulgaris, Pernicious anemia, polyarteritis nodosa, polychondritis, autoimmune polyglandular syndrome, Polymyalgia rheumatica, polymyositis and dermatomyositis, primary agammaglobulinemia, Primary biliary cirrhosis, psoriasis, psoriatic arthritis, Raynaud's phenomenon, Reiter's syndrome, rheumatoid arthritis, sarcoidosis, scleroderma, stiff-person syndrome, systemic lupus erythematosus, lupus erythematosus, Takayasus Arteritis, temporal arteritis, giant cell arteritis, ulcerative colitis, uveitis, vitiligo and Wegener's granulomatosis;

(vii) inflammatory diseases including asthma, encephilitis, inflammatory colitis, chronic obstructive pulmonary disease, allergy, septic shock, pulmonary fibrosis, undifferentiated spondyloarthropathy, undifferentiated arthropathie, arthritis, Inflammatory osteolysis, and chronic inflammation resulting from infection by chronic virus or bacteria; and (viii) diseases associated with wound repair such as, for example, inhibition of keloid formation and other types of scarring, and enhancing wound healing, including chronic wounds.

Preferably, the composition of the present invention is used for cancers, viral diseases, bacterial diseases, infectious diseases or autoimmune diseases.

The composition of this invention may be provided as a pharmaceutical composition. The pharmaceutical composition of this invention includes a pharmaceutically acceptable carrier besides the active ingredient compound. The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995).

The pharmaceutical composition according to the present invention may be administered orally or parenterally, and preferably, administered parenterally. For parenteral administration, it may be administered intravenously, subcutaneously, intramusculerly, intraperitoneally or transdermally.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, pharmaceutical composition of the present invention may be administered with a daily dosage of 0.001-10000 mg/kg (body weight).

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

In another aspect of this invention, there is provided a screening method for an epitope having immunogenicity comprising the steps of:
(a) encapsulating (i) an immunostimulatory oligonucleotide and (ii) a peptide as a candidate material for an epitope into a liposome containing an anionic surfactant and a neutral phospholipid;
(b) immunizing a non-human animal with said liposome-encapsulated (i) the immunostimulatory oligonucleotide and (ii) the peptide as the candidate material for the epitope;
(c) analyzing the immune response of said immunized non-human animal.

As the epitope, the peptide, the immunostimulatory oligonucleotide and the liposome of the present invention are mentioned above, they are omitted herein to avoid excessive overlaps.

The immunizing method of liposome-encapsulated immunostimulatory oligonucleotide or peptide includes which known to those skilled in the art and preferably is a parenteral administration. For parenteral administration, it may be administered intravenously, subcutaneously, intramusculerly, intraperitoneally or transdermally.

The "non-human animal" used in the present invention includes various animals generally used in the field of the art, and preferably is a mammal, and most preferably is a mouse, a rabbit or a rat.

The measure of immune response in the immunized animal is performed by, for example, analyzing the titer of anti-peptide antibodies (total IgG, IgG1 and IgG2a) from the sera of the subject animal administered with selected the liposome-encapsulated peptide. Preferably, the method for measuring the titer of the antibody includes, but not limited to, ELISA (enzyme-linked immunosorbent assay), lateral flow test, MIA (magnetic immunoassay), immunoprecipitation. More preferably, ELISA analysis may be used.

Where the specific peptide sequence increases the titer of anti-peptide antibody, said specific peptide is determined as an epitope or a peptide vaccine.

In still another aspect of this invention, there is provided a screening method for an antibody against a protein antigen comprising the steps of:
(a) encapsulating (i) an immunostimulatory oligonucleotide and (ii) a peptide of the protein antigen as a candidate material for an epitope into a liposome containing an anionic surfactant and a neutral phospholipid;
(b) immunizing a non-human animal with said liposome-encapsulated (i) the immunostimulatory oligonucleotide and (ii) the peptide as the candidate material for the epitope; and
(c) selecting a peptide epitope having immunogenicity by analyzing the immune response of said immunized non-human animal;
(d) contacting said selected peptide epitope with the antibody of interest to be analyzed;
(e) contacting the resultant of step (d) with said protein antigen; and
(f) analyzing the binding of said protein antigen and the antibody of interest.

The screening method of the present invention may be carried out by various processes, especially by high throughput method through diverse binding assays known to those skilled in the art.

The protein antigen or the candidate antibody of the present invention may be labeled with a detectable label. For example, said detectable label includes, but not limited to, chemical label (e.g., biotin), enzyme label (e.g., horseradish peroxidase, alkaline phosphatase, peroxidase, luciferase, 3-galactosidase and β-glucosidase), radioactive label (e.g., C14, 1125, P32 and S35), fluorescence label (e.g., coumarin, fluorescein, FITC (fluoresein Isothiocyanate), rhodamine 6G, rhodamine B, TAMRA (6-carboxy-tetramethyl-rhodamine), Cy-3, Cy-5, Texas Red, Alexa Fluor, DAPI (4,6-diamidino-2-phenylindole), HEX, TET, Dabsyl and FAM), luminescent label, chemiluminescent label, FRET (fluorescence resonance energy transfer) label or metal label (e.g., gold and silver).

For using the detectably labeled protein antigen or candidate antibody, a binding of protein antigen with antibody may be analyzed through the signal generated by the label. Where using alkaline phosphatase, bromochloroindolylphosphate (BCIP), nitro blue tetrazolium (NBT), naphthol-AS-B1-phosphate and ECF (enhanced chemifluorescence) may be used as a substrate; in the case of using horseradish peroxidase, chloronaphtol, aminoethylcarbazol, diaminobenzidine, D-luciferin, lucigenin (bis-/V-methylacridinium nitrate), resorufin benzyl ether, luminol, Amplex Red reagent (10-acetyl-3,7-dihydroxphenoxazine, Pierce), HYR (p-phenylenediamine-HCL and pyrocatechol), TMB (3,3,5,5-tetramethylbenzidine), ABTS (2,2-Azine-di[3-ethylbenzthiazoline sulfonate]), OPD (o-phenylenediamine) and naphtol/pyronin may be used as a substrate.

Alternatively, the binding of the protein antigen with the antibody may be measured without labeling of interactants. For example, a microphysiometer may be used to analyze the binding of the antibody and antigen. The microphysiometer is a device for determining the cell's environment-acidifying rate using LAPS (light-addressable potentiometric sensor). The change of acidifying rate may be used as an indicator for binding of the candidate antibody and protein antigen binding (33).

Binding capacity of the candidate antibody to the protein antigen may be determined by an real-time BIA (bimolecular interaction analysis) (34, 35). A BIA is a real-time analyzing technique for the specific interaction without labeling of interactants (e.g., BIAcore™). The change of SPR (surface plasmon resonance) is used as an indicator of real-time reaction between the molecules.

In still another aspect of this invention, there is provided a method for preparing an antibody against a protein antigen comprising the steps of:
 (a) encapsulating (i) an immunostimulatory oligonucleotide and (ii) a peptide of the protein antigen as a candidate material for an epitope into a liposome containing an anionic surfactant and a neutral phospholipid;
 (b) immunizing a non-human animal with said liposome-encapsulated (i) the immunostimulatory oligonucleotide and (ii) the peptide as the candidate material for the epitope; and
 (c) selecting a peptide epitope having immunogenicity by analyzing the immune response of said immunized non-human animal;
 (d) producing the antibody by immunizing a non-human animal with said selected peptide epitope.

According to the present invention, the step of obtaining an antibody from an immunized animal is performed by varied method known to those skilled in the art, including ethanol precipitation method, ion exchange adsorption chromatography or protein A or protein G-column chromatography. Alternatively, pure immunoglobulins may be isolated from the mammalian plasma through adsorption chromatography using specific antigen bound agarose beads. Still alternatively, the information of immunoglobulin may be acquired from the cDNA library having genetic information of the antibody protein obtained from a peripheral blood lymph node or a B cell. Based on said information, the immunoglobulin may be prepared in genetically engineered way. The genetic recombinant immunoglobulin protein prepared by above described method contains base sequence of mammal's immunoglobulin amino acid or humanized genetic recombinant immunoglobulin protein with partial mutation thereof (Vaughan T J, et al. Human antibodies design. Nature Biotech 16:535-539 (1998)). The purified antibody may be stored on ice before use. Furthermore, the method of the present invention may additionally comprise a step of generating a monoclonal antibody, a humanized antibody or an affinity maturated antibody through capturing B cells from the immunized animals.

In still another aspect of this invention, there is provided a peptide vaccine composition against an influenza A virus comprising the amino acid sequence selected from the group consisting of SEQ ID NO:1 to SEQ ID NO:9 and SEQ ID NO:19 to SEQ ID NO:37.

In still another aspect of this invention, there is provided a peptide vaccine composition against human integrin protein β4 comprising the amino acid sequence selected from the group consisting of SEQ ID NO:42 to SEQ ID NO:46.

In still another aspect of this invention, there is provided a peptide vaccine composition against a hepatocarcinoma comprising the amino acid sequence selected from the group consisting of SEQ ID NO:10 and SEQ ID NO:11.

In still another aspect of this invention, there is provided a peptide vaccine composition against a hepatitis c virus comprising the amino acid sequence of SEQ ID NO:12.

In still another aspect of this invention, there is provided a peptide vaccine composition against a RSV (respiratory syncytial virus) comprising the amino acid sequence of SEQ ID NO:13 and SEQ ID NO:38 to SEQ ID NO:41.

As the peptide vaccines of the present invention are mentioned in describing the immunostimulatory composition, they are omitted herein to avoid excessive overlaps.

In still another aspect of this invention, there is provided a method for preventing or treating influenza A virus infectious diseases, cancers, hepatocarcinomas, hepatitis C or RSV (respiratory syncytial virus) infectious diseases.

The features and advantages of the present invention will be summarized as follows:
 (a) The present invention provides a composition for enhancing an immune response, an epitope having immunogenicity, screening and preparing methods thereof, an antibody to a peptide antigen and screening and preparing methods thereof.
 (b) The present invention may be effectively used for preventing or treating diverse immune-deficiency diseases such as cancer, influenza virus, hepatitis C virus and RSV (respiratory syncytial virus) by enhancing immune responses.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Oligodeoxynucleotides and Reagents

ODNs (Oligodeoxynucleotides) were synthesized from Samchully Pharm (Seoul, Korea). The MB-ODN 4531 consisted of 20 bases that contained three CpG motifs (underlined): AGCAG<u>CG</u>TT<u>CG</u>TGT<u>CG</u>GCCT. The MB-ODN 4531 sequences used in this study were either phosphodiester (O) or phosphorothioate-modified (S). The phosphorothioate version of MB-ODN 4531(O) is MB-ODN 4531(S). The MB-ODN 4531GC is a derivative of MB-ODN 4531 with one of the CG sequences reversed to GC (underlined): AGCAG<u>GC</u>TTCGTGTCGGCCT. Fluorescent or biotin tags were conjugated to the 3' end of each ODNs. The endotoxin content of the ODNs was less than 1 ng/mg of ODN as measured by a Limulus amebocyte assay (Whittaker Bioproducts, Walkersville, Md., USA).

TABLE 1

| Synthetic ODN derivatives | | |
|---|---|---|
| ODNs | Sequences | Modification |
| MB-ODN 4531(O) | AGCAGCGTTCGTGTCGGCCT | None |
| MB-ODN 4531(GCO) | AGCAGGCTTCGTGTCGGCCT | None |
| MB-ODN 4531(S) | AGCAGCGTTCGTGTCGGCCT | S |
| MB-ODN 4531(S)T13 | AGCAGCGTTCTTG | S |

TABLE 1-continued

Synthetic ODN derivatives

| ODNs | Sequences | Modification |
|---|---|---|
| MB-ODN 4531(S)CT | AGCAGCGTTCTTGTCGGCCT | S |
| MB-ODN 4531(S)CS | AGGCCGACAAGAACGCTGCT | S |

The changes of CG dinucleotide to GC or CT are indicated in bold letter underlined. MB-ODN 4531(S)CS is the complementary sequences of the MB-ODN 4531. None, phosphodiester backbone linkage; S, phosphorothioate backbone modification

Example 2

Selection of Candidate Epitope and Synthesis of Peptides

Peptide sequences were selected based on hydrophilicity, hydrophobocity, secondary structure, antigenicity index, amphipathicity. To identify the effect of epitope-based peptides, we synthesized peptides as a 14 or 17 amino acid long from HA proteins of several influenza A strain (Table 2, 3, 4, 5, 6, 7, 8, and 9), hTM4SF5 (human tetraspanin transmembrane 4 superfamily member 5) protein of a hepatocarcinoma, an envelope protein of a hepatitis C virus, attachment (G) glycoprotein of RSV (respiratory syncytial virus) (G(hRSV-G)) (Table 10), the fusion protein of RSV (HRSV-F) (Table 11 and 12), and human integrin β4 (hIB4) (Table 13). The amino acid sequence of influenza A viruses HA protein is numbered on the basis of alignment with the human H3 sequence (A/Aichi/2/68). Peptides were synthesized by the Fmoc solid-phase method by use of an automated peptide synthesizer (Peptron III-R24, Peptron, Daejeon, Korea). After deprotection of the synthesized peptides from the resin, the peptides were purified and analyzed by reverse-phase HPLC (Waters 2690 Separations Module, Waters, Milford, USA) using Vydac C8 analytical RP column to a purity of >90%. The peptide was identified by use of a mass spectrometer (HP 1100 Series LC/MSD, Hewlett-Packard, Roseville, USA).

TABLE 2

Candidate epitopes of A/Viet Nam/1203/2004 hH5N1 HA protein

| Strain | Sequences | Location | Abbreviation |
|---|---|---|---|
| A/Vietnam/ 1203/2004 H5N1 | ILEKKHNGKLC | 58-68 | hH5N1 HA58 |
| | CYPGDFNDYEELK | 113-125 | hH5N1 HA113 |
| | IATRSKVNGQSGRM | 233-246 | hH5N1 HA233 |
| | LRNSPQRERRRKKRG | 336-350 | hH5N1 HA336 |
| | VDGWYGYHHSNEQGSGYA | 363-380 | hH5N1 HA363 |
| | HHSNEQGSGYAADKEST | 370-386 | hH5N1 HA370 |
| | SGYAADKESTQKAIDGVT | 377-394 | hH5N1 HA377 |
| | ESTQKAIDGVTNKVNSII | 384-401 | hH5N1 HA384 |
| | QKAIDGVTNKVNSI | 387-400 | hH5N1 HA387 |
| | TNKVNSIIDKMNTQ | 394-407 | hH5N1 HA394 |

Peptide sequences for epitope screening were selected from A/Vietnam/1203/2004 H5N1 HA protein (NCBI database, AAW80717) based on hydrophilicity, hydrophobicity, secondary structure, antigenicity index, and amphipathicity (http://tools.immuneepitpoe.org/main/index.html). The amino acid sequence of A/Vietnam/1203/2004 hH5N1 HA protein is numbered on the basis of alignment with the human H3 sequence (A/Aichi/2/68).

TABLE 3

Conservation of sequences corresponding to hH5N1 HA370 epitope within influenza A H5N1 and H1N1 strains

| Strains (subtypes) | Accession No. | Abbreviation | Sequences |
|---|---|---|---|
| A/Vietnam/1203/2004 (H5N1) | AAW80717 | hH5N1 HA370 | HHSNEQGSGYAADKEST |
| A/Hong Kong/485/97 (H5N1) | AAD52043 | hH5N1-HK HA370 | HHSNEQGSGYAADQEST |
| A/WSN/1933 (H1N1) | AAA43209 | hH1N1-WSN HA370 | HHQNEQGSGYAADQKST |
| A/New York/604/1995 (H1N1) | ABE11867 | hH1N1-NY HA370 | HHQNEQGSGYAADKKST |
| A/Ohio/3559/1988 (H1N1) | ABU80400 | hH1N1-OH HA370 | HHQNEQGSGYAADRKST |

The amino acid sequence of influenza A viruses HA protein is numbered on the basis of alignment with the human H3 sequence (A/Aichi/2/68).

TABLE 4

Conservation of sequences corresponding to hH5N1 HA370 epitope within swine-origin influenza A H1N1 strains

| Strains (isolation number)* | ACCESSION No. | Abbreviation | Sequences |
| --- | --- | --- | --- |
| A/Vietnam/1203/2004 (H5N1) | AAW80717 | hH5N1 HA370 | HHSNEQGSGYAADKEST |
| A/Texas/05/2009 (H1N1) (1749/1750) | ACP41934 | A/H1N1-TX HA370 | HHQNEQGSGYAADLKST |
| A/San Antonio/PR922/2009 (H1N1) (1/1750) | ACU29959 | A/H1N1-SA HA370 | HHQNEQGSGYAADMKST |

(isolation number)* denotes the number of strains containing the specific sequences among the 1750 different strains of swine-origin influenza A H1N1 virus isolated up to date.

TABLE 5

Sequence alignment of hH5N1 HA233 epitope from A/Vietnam/1203/2004 and corresponding sequences from other H5N1 strains

| Strain/isolation (isolation number) | Accession No. | Abbreviation | Sequence |
| --- | --- | --- | --- |
| A/Viet Nam/1203/2004 (229) | AAW80717 | hH5N1 HA233 | IATRSKVNGQSGRM |
| A/Hong Kong/482/97 (20) | AAC32100 | hH5N1 HA233-1 | IATRPKVNGQSGRM |
| A/Hong Kong/213/03 (9) | BAE07201 | hH5N1 HA233-2 | IATRSKVNGQNGRM |
| A/Indonesia/TLL007/2006 (4) | ABW74707 | hH5N1 HA233-3 | MATRSKVNGQSGRM |
| A/Viet Nam/JP4207/2005 (3) | ABO10183 | hH5N1 HA233-4 | IATRSKVNGQSGRI |
| A/Hong Kong/483/97 (2) | AAC32099 | hH5N1 HA233-5 | IATRPKVNGQSGRI |
| A/Egypt/14724-NAMRU3/2006 (2) | ABM54179 | hH5N1 HA233-6 | IATRSKINGQSGRI |
| A/Viet Nam/CL100/2004 (2) | ABE97630 | hH5N1 HA233-7 | IATRSKINGQSGRM |
| A/Anhui/2/2005 (2) | ABD28181 | hH5N1 HA233-8 | IATRSKVNGRSGRM |
| A/Egypt/0636-NAMRU3/2007 (1) | ABM92273 | hH5N1 HA233-9 | IAARSKVNGQSGRM |
| A/Thailand/1(KAN-1A)/2004 (1) | ABL10088 | hH5N1 HA233-10 | IATRSEVNGQSGRM |
| A/Egypt/2289-NAMRU3/2008 (1) | ACI06181 | hH5N1 HA233-11 | IATRSKVNGQIGRM |
| A/Egypt/3300-NAMRU3/2008 (1) | ACI06185 | hH5N1 HA233-12 | IATRSKVNGQSGRV |
| A/Anhui/T2/2006 (1) | ABU80630 | hH5N1 HA233-13 | IATRTKVNGQSGRM |
| A/Indonesia/CDC1032N/2007 (1) | ABM90489 | hH5N1 HA233-14 | TATRSKVNGQSGRM |

(isolation number)* denotes the number of strains containing the specific sequences among the 279 different strains of human H5N1 virus isolated up to date.

TABLE 6

Conservation of the sequence corresponding to H5N1 HA233 epitope in influenza A virus subtypes

| Strains/isolation (subtypes) | Accession No. | Abbreviation | Sequences |
| --- | --- | --- | --- |
| A/Vietnam/1203/2004 (H5N1) | AAW80717 | hH5N1 HA233 | IATRSKVNGQSGRM |
| A/WSN/1933 (H1N1) | AAA43209 | hH1N1-WSN HA233 | IAARPKVKDQHGRM |
| A/Hong Kong/1131/1998 (H1N1) | AAK70451 | hH1N1-HK HA233 | IAKRPKVRDQEGRI |
| A/Thailand/271/2005 (H1N1) | ABK57093 | hH1N1-Thai HA233 | IAKRPKVRGQAGRM |

TABLE 6-continued

Conservation of the sequence corresponding to H5N1 HA233 epitope in influenza A virus subtypes

| Strains/isolation (subtypes) | Accession No. | Abbreviation | Sequences |
|---|---|---|---|
| A/Texas/05/2009 (H1N1) | ACP41934 | A/H1N1-TX HA233 | IAIRPKVRDQEGRM |
| A/Michigan/2/2003 (H1N2) | ABI96104 | hH1N2 HA233 | ITKRPKVRDQEGRI |
| A/mallard/Alberta/202/96 (H2N5) | AAT65325 | mH2N5 HA233 | IATRPKVNGQGGRM |
| A/Hong Kong/1143/99 (H3N2) | AAK62039 | hH3N2 HA233 | IGSRPWVRGVSSRI |
| A/equine/Jilin/1/1989 (H3N8) | AAA43151 | eH3N8 HA233 | IGSRPWVRGQSGRV |
| A/Tern/South Africa/61 (H5N3) | ABI84970 | tH5N3 HA233 | IATRPKVNGQSGRV |
| A/Canada/rv504/2004 (H7N3) | ABI85000 | hH7N3 HA233 | PGARPQVNGQSGRI |
| A/England/268/1996(H7N7) | AAC40998 | hH7N7 HA233 | PGARPQVNGQSGRI |
| A/Hong Kong/1074/99 (H9N2) | CAB95857 | hH9N2 HA233 | IGPRPLVNGLQGRI |
| A/mallard/Astrakhan/263/1982 (H14N5) | ABI84453 | mH14N5 HA233 | IGSRPRVRNQSGRI |
| A/shelduck/WA/1756/1983 (H15N2) | ABB90704 | sH15N2 HA233 | PGARPKVNGQAGRI |

TABLE 7

Conservation of the sequence corresponding to H5N1 HA233 epitope in H1N1 strains reported up to date

| Strains (isolation number)* | Accession No. | Sequences |
|---|---|---|
| A/Hong Kong/1131/1998 (1896) | AAK70451 | IAKRPKVRDQEGRI |
| A/Brazil/11/1978 (68) | ABO38065 | --------G----- |
| A/Chile/1/1983 (67) | ABO38340 | --------N----- |
| A/Iowa/1943 (29) | ABO38373 | --E-----G-A--- |
| A/Nagoya/27/1995 (23) | BAC82887 | -T------------ |
| A/South Australia/26/2000 (17) | ABK79970 | --R----------- |
| A/Puerto Rico/8/34 (15) | AAA43194 | --E-------A--M |
| A/Hickox/1940 (13) | ABI20826 | --E-----G-A--M |
| A/Kyoto/1/1995 (11) | BAC82881 | ------I------- |
| A/Fukushima/2/1988 (10) | AAA43170 | ---------R---- |
| A/Hong Kong/470/1997 (8) | CAD29932 | -V------------ |
| A/Ohio/3559/1988 (4) | ABU80400 | --T-------A--M |
| A/Maryland/2/1980 (3) | ABO33006 | -S------------ |
| A/WSN/1933 (3) | ACF54598 | --A----K--H--M |
| A/Fort Worth/50 (3) | ABD61735 | ----------P--M |
| A/Kojiya/1/1952 (2) | BAA96113 | --------G-P--M |
| A/Malaysia/54 (2) | ABD60966 | --E-----G-P--M |
| A/Texas/UR06-0502/2007 (1) | ABV29612 | V------------- |
| A/Texas/UR06-0502/2007 (1) | ABO38021 | M------------- |
| A/Hong Kong/1134/1998 (1) | AAK70459 | -V------R---- |

TABLE 7-continued

Conservation of the sequence corresponding to H5N1 HA233 epitope in H1N1 strains reported up to date

| Strains (isolation number)* | Accession No. | Sequences |
|---|---|---|
| A/Switzerland/8808/2002 (1) | CAD57618 | -VA-----E-A--- |
| A/Wisconsin/10/1998 (1) | AAO88265 | -TT-------A--M |
| A/New York/626/1996 (1) | ABG47829 | -T------N----- |
| A/Georgia/5/2003 (1) | ABI96112 | -T------G----- |
| A/Memphis/2/1983 (1) | ABG88344 | -S------N----- |
| A/Memphis/1/1983 (1) | ABG88333 | -S------G----- |
| A/Albany/20/1978 (1) | ABP49448 | -SE-----G----- |
| A/Lackland/7/1978 (1) | ABO32992 | -SE-------K--- |
| A/Texas/AF1960/2008 (1) | ACH69241 | --Q----------- |
| A/South Africa/42/2000 (1) | ABO21724 | -----P-------- |
| A/Saga/2/1957 (1) | BAA96117 | --------G-S--M |
| A/Thailand/271/2005 (1) | ABK57093 | --------G-A--M |
| A/Kentucky/UR06-0339/2007 (1) | ABW91526 | --------E----- |
| A/Denver/57 (1) | ABD15258 | ----------S--M |
| A/Singapore/03/1990 (1) | AAA16778 | ----------R--- |
| A/Austria/404738/2008 (1) | ACA03766 | ----------G--- |
| A/New Caledonia/V77245/2007 (1) | ABQ52695 | -----------RKN |
| A/RiodeJaneiro/404/01 (1) | AAY42121 | ------------G- |
| A/Texas/06/2007 (1) | ABW23325 | --------B----- |
| A/Kamata/69/1996 (1) | BAA96123 | ------I-N----- |
| A/Milan/11/2006 (1) | ABZ85909 | ----L--------- |
| A/Kamata/85/1987 (1) | BAA96118 | --I----------- |
| A/Huston/43 (1) | AAM76691 | --G-----G-A--M |
| A/Phila/1935 (1) | ABO38384 | --E-------T--M |
| A/Arizona/14/1978 (1) | ABN59423 | --E----------- |
| A/Lackland/3/1978 (1) | ABO32981 | --E-------A--- |
| A/Henry/1936 (1) | ABO38351 | --E--E----A--M |
| A/Wisconsin/301/1976 (1) | ABV45838 | --A-----G-A--M |
| A/Wilson-Smith/33 (1) | ABD77796 | --A-------P--M |
| A/Wilson-Smith/1933 (1) | ABF21278 | --A-------H--M |
| A/Brevig_Mission/1/18 (1) | AAD17218 | --A-------A--M |
| A/London/1/1919 (1) | AAO65769 | --A---I-G-A--M |

(isolation number)* denotes the number of strains containing the specific sequences corresponding to H5N1 HA233 epitope among the 2209 different strains of human H1N1 virus isolated up to date.

TABLE 8

Conservation of the sequence corresponding to H5N1 HA233 epitope in swine-origin influenza A H1N1 strains up to date

| Strains (isolation number)* | ACCESSION No. | Sequence |
|---|---|---|
| A/Viet Nam/1203/2004 (H5N1) | AAW80717 | IATRSKVNGQSGRM |
| A/Texas/05/2009 (1608/1751) | ACP41934 | --I-P--RD-E--- |
| A/Almati/01/2009 (48/1751) | ACU56931 | --I-P--RE-E--- |
| A/Argentina/HNRG16/2009 (29/1751) | ADA83595 | --I-P--R--E--- |
| A/California/12/2009 (14/1751) | ACT36662 | --I-P--RDXE--- |
| A/Ekaterinburg/01/2009 (10/1751) | ACU56924 | --I-P--RDRE--- |
| A/Finland/614/2009 (9/1751) | ACZ81656 | --I-P--RX-E--- |
| A/Malaysia/8860/2009 (8/1751) | ADD14139 | --I-P--RN-E--- |
| A/Pennsylvania/14/2009 (3/1751) | ACV67237 | -XI-P--RD-E--- |
| A/South Carolina/09/2009 (2/1751) | ACR49284 | --I-P--RB-E--- |
| A/Texas/04/2009 (2/1751) | ACR49285 | --I-P--RXXE--- |
| A/Singapore/9061364 (2/1751) | ACZ04992 | --I-P--RD-E-X- |
| A/Singapore/GP2641/2009 (2/1751) | ACY46823 | --I-P-XXX-XX-- |
| A/Singapore/GP2695/2009 (2/1751) | ACY46873 | --I-P--XD-E--- |
| A/Ancona/04/2009 (1/1751) | ACT83739 | ----P--RD-E--- |
| A/Argentina/HNRG15/2009 (1/1751) | ADA83591 | -SI-P--RD-E--- |
| A/Argentina/HNRG42/2009 (1/1751) | ADA83664 | T-I-P--RD-E--- |
| A/Hiroshima/201/2009 (1/1751) | ACX31934 | -TI-P--RG-E--- |
| A/Novgorod/01/2009 (1/1751) | ADA83043 | --I-P--RERE--- |
| A/Santo Domingo/WR1057N/2009 (1/1751) | ACY77693 | -TI-P--RD-E--- |
| A/Singapore/GP2316/2009 (1/1751) | ACY46813 | X-I-P--RD-EXX- |
| A/Singapore/GP2687/2009 (1/1751) | ACY46863 | --I-P--XD-E-X- |
| A/Singapore/ON1187/2009 (1/1751) | ACY46782 | --I-P--XX-X-X- |
| A/Singapore/ON141/2009 (1/1751) | ACY46123 | --I-P--GD-E--- |
| A/Singapore/ON2081/2009 (1/1751) | ACY46843 | --I-P--XD-XXX- |
| A/Wisconsin/629-50339/2009 (1/1751) | ACZ16840 | --I-T--RD-E--- |

(isolation number)* denotes the number of strains containing the specific sequences corresponding to H5N1 HA233 epitope among the 1751 different strains of swine-origin influenza A H1N1 virus isolated up to date.

TABLE 9

Conservation of the sequence corresponding to A/H1N1 HA370 epitope in influenza A virus subtypes reported up to date

| Strains | ACCESSION No. | ABBREVIATION | Sequences |
|---|---|---|---|
| A/Texas/05/2009 (H1N1) | ACP41934 | A/H1N1-TX HA370 | HHQNEQGSGYAADLKST |
| A/San Antonio/PR922/2009 (H1N1) | ACU29959 | A/H1N1-SA HA370 | HHQNEQGSGYAADMKST |

TABLE 9-continued

Conservation of the sequence corresponding to A/H1N1 HA370 epitope in influenza A virus subtypes reported up to date

| Strains | ACCESSION No. | ABBREVIATION | Sequences |
|---|---|---|---|
| A/WSN/1933 (H1N1) | AAA43209 | hH1N1-WSN HA370 | HHQNEQGSGYAADQKST |
| A/New York/604/1995 (H1N1) | ABE11867 | hH1N1-NY HA370 | HHQNEQGSGYAADKKST |
| A/Ohio/3559/1988 (H1N1) | ABU80400 | hH1N1-OH HA370 | HHQNEQGSGYAADRKST |
| A/Adachi/2/1957 (H2N2) | BAG72216 | hH2N2 HA370 | HHSNDQGSGYAADKEST |
| A/New York/61A/2003 (H3N2) | AAX11455 | hH3N2 HA370 | RHQNSEGTGQAADLKST |
| A/New York/356/2004 (H3N2) | AAZ74419 | hH3N2 HA370-1 | RHQNSEGIGQAADLKST |
| A/Viet Nam/1203/2004 (H5N1) | AAW80717 | hH5N1 HA370 | HHSNEQGSGYAADKEST |
| A/Hong Kong/485/97 (H5N1) | AAD52043 | hH5N1-HK HA370 | HHSNEQGSGYAADQEST |
| A/England/268/1996(H7N7) | AAC40998 | hH7N7 HA370 | RHQNAQGEGTAADYKST |
| A A/Shantou/239/98(H9N2) | AAL32476 | hH9N2-ST HA370 | QHSKYQGVGMAADRDST |
| A/Hong Kong/1074/99(H9N2) | CAB95857 | hH9N2-HK HA370 | QHSNDQGVGMAADRDST |

TABLE 10

Candidate epitopes of human tetraspanin transmembrane 4 superfamily member 5 (hTM4SF5) of human hepatocarcinoma, envelope protein (E protein) of HCV (HCV-E), attachment glycoprotein G and fusion protein (F protein) in human RSV (HRSV-G, HRSV-F)

| Proteins | Peptides | Sequences | Location | Length (mer) |
|---|---|---|---|---|
| hTM4SF5 | TM4SF5R1 | NGETSWTNTNHLSL | 32-45 | 14 |
| | TM4SF5R2-1 | RNGPRCLMNGEWGY | 113-126 | 14 |
| | TM4SF5R2-2 | GEWGYHFEDTAGAY | 122-135 | 14 |
| | TM4SF5R2-3 | NRTLWDRCEAPPRV | 138-151 | 14 |
| | TM4SF5R2-4 | WDRCEAPPRVVPWN | 142-155 | 14 |
| | TM4SF5R2-5 | GAYLLNRTLWDRCEA | 133-147 | 15 |
| | HCVE1 57 | TRDGKLPTTQLRR | 57-69 | 13 |
| | HCVE2 202 | CFRKHPEATYSR | 202-213 | 12 |
| | HCVE2 269 | CDLEDRDRSELSP | 269-281 | 13 |
| HRSV-G | hRSVG1 | MSKHKNQRTARTLEKTWD | 1-18 | 18 |
| HRSV-G | hRSVG150 | PRLKNPPKKPKDDY | 150-163 | 14 |
| HRSV-F | hRSVF99 | NTPAANNRARREAPQYM | 99-115 | 17 |

TABLE 11

Candidate epitopes of hRSV A strain long F protein

| Strain | Sequences | Location | Abbreviation | Variation |
|---|---|---|---|---|
| Human respiratory syncytial virus A | CFASSQNITEEFYQ | 21-34 | HRSV-Fa1 | 5 type |

TABLE 11-continued

Candidate epitopes of hRSV A strain long F protein

| Strain | Sequences | Location | Abbreviation | Variation |
| --- | --- | --- | --- | --- |
| strain Long (hRSV A strain Long) | IKENKCNGTDAKVKL | 64-78 | HRSV-Fa2 | 2 type |
| | KVKLIKQELDKYKNA | 75-89 | HRSV-Fa3 | 4 type |
| | TSPLCTTNTKEGSNI | 318-332 | HRSV-F1 | 2 type |
| | GCDYASNKGVDTVSV | 438-452 | HRSV-F2 | 3 type |
| | LVFPSDEFDASISQV | 481-495 | HRSV-F3 | 1 type |
| | SDEFDASISQVNEKI | 485-499 | HRSV-F4 | 1 type |
| | RSTPVTLSKDQLSGI | 553-567 | HRSV-F5 | 3 type |
| | TDRGWYCDNAGSVSF | 337-351 | HRSV-F6 | 1 type |
| | AGSVSFFPQAETCKV | 346-360 | HRSV-F7 | 3 type |
| | YGKTKCTASNKNRGII | 417-432 | HRSV-F8 | 2 type |
| | CKIMTSKTDVSSSVI | 393-407 | HRSV-F9 | 3 type |

Peptide sequences for epitope screening were selected based on hydrophilicity, hydrophobicity, secondary structure, antigenicity index, amphipathicity from hRSV A strain long F protein.

TABLE 12

Sequence variation of candidate epitopes in hRSV A strain long strains

| Abbreviation | Long strain sequence | Other sequences | Abbreviation |
| --- | --- | --- | --- |
| HRSV-Fa1 | CFASSQNITEEFYQ | CFASGQNITEEFYQ | |
| | | YLTSSQNITEEFYQ | |
| HRSV-Fa2 | IKENKCNGTDAKVKL | IKETKCNGTDTKV | |
| HRSV-Fa3 | KVKLIKQELDKYKNA | KVKLMKQELDKYKNA | HRSV-Fa3-1 |
| | | KVKLIKQELDKYKSA | HRSV-Fa3-2 |
| | | KVKLINQELDKYKNA | HRSV-Fa3-3 |
| HRSV-Fa4 | TPAANNRARRE | TPAANSRARRE | |
| | | TSAANNRARRE | |
| | | TTAANNRARRE | |
| | | TPATNNRARRE | |
| | | TPPTNNRARRE | |
| HRSV-F1 | TSPLCTTNTKEGSNI | TSPLCTTNIKEGSNI | |
| HRSV-F2 | GCDYASNKGVDTVSV | GCDYVSNKGVDTVSV | |
| | | GCDYASNKGMDTVSV | |
| HRSV-F3 | LVFPSDEFDASISQV | none | |
| HRSV-F4 | SDEFDASISQVNEKI | none | |
| HRSV-F5 | RSTPVTLSKDQLSGI | RNTPVTLSKDQLSGI | |
| | | KSTPVTLSKDQLSGI | |
| HRSV-F6 | TDRGWYCDNAGSVSF | none | |
| HRSV-F7 | AGSVSFFPQAETCKV | AGSVSFFPLAETCKV | HRSV-F7-1 |
| | | AGSVSFFPQADTCKV | HRSV-F7-2 |
| HRSV-F8 | YGKTKCTASNKNRGII | YGKTKCTASNKDRGII | |
| HRSV-F9 | CKIMTSKTDVSSSVI | CKIMTSKADVSSSVI | |
| | | CKIMTSKTDISSSVI | |

TABLE 13

Candidate epitopes of human integrin beta 4 (hIB4)

| Protein | Sequences | Location | Abbreviation | Length |
|---|---|---|---|---|
| Human integrin4 | DKVSVPQTDMRPEKL | 176-190 | hIB4-VWA-1-1 | 15 |
| | KEPWPNSDPPFSFKN | 191-205 | hIB4-VWA-1-2 | 15 |
| | PQTDMRPEKLKEPWPNSDP | 181-199 | hIB4-VWA-1-3 | 19 |
| | LTEDVDEFRNKLQGERISGN | 209-228 | hIB4-VWA-2 | 20 |
| | LDTTGTYTQYRTQDYPSVPT | 290-309 | hIB4-VWA-3 | 20 |
| | LQKEVRSARCSFNGD | 459-473 | hIB4-EGF-1 | 15 |

Example 3

Preparation of CpG-DNA-Peptide (or Protein)-Liposome Complex

The following liposomes used in the present invention: CHEMS, Chol, DOPE, and DSPC were purchased from Sigma. DC-Chol and PEG-PE were acquired from Avanti-Polar Lipids (Alabaster, Ala., USA). Complexes of CpG-DNA and protein (or peptide) with DOTAP (Roche, Indianapolis, Ind., USA), lipofectamine (Invitrogen, Carlsbad, Calif., USA), or lipofectin (Invitrogen, Carlsbad, Calif., USA) were prepared according to the manufacturer's specifications. Liposome complexes consisting encapsulated CpG-DNA and protein (or peptide) with DOPE/CHEMS, DSPC/Chol, DSPC/CHEMS/PEG-PE, Chol/DOPE/PEG-PE or Dc-Chol/DOPE/PEG-PE were prepared as reported previously (14, 23) and modified. In brief, DOPE and CHEMS were mixed at a molar ratio of 1:1 and then the mixture were evaporated with nitrogen gas to make solvent-free lipid film, and mixed in ethanol (final concentration of 10%) then resuspended in equal volume of water soluble CpG-DNA and protein (or peptide) mixture with vigorous stirring at room temperature for 30 min. After adjusting pH to 7.0, the lipoplex solution slightly sonicated for 30 seconds using a sonicator, and filtered with 0.22 μm filter and then freeze-thawed was repeated three times in the liquid nitrogen (14, 23).

Example 4

Induction of Humoral Immune Responses by CpG-DNA-Peptide (or Protein)-Liposome Complex <4-1> Immunization Mice were maintained under specific-pathogen-free conditions. Four-week-old male BALB/c (H-$2^b$) mice were purchased from Central Lab. Animal Inc. (Seoul, Korea). The present inventor's animal studies were approved by the Institutional Animal Care and Use Committee of Hallym University.

4 week-old BALB/c mice were injected i.p. with HEL (hen egg lysozyme) (50 μg/mouse) and MB-ODN 4531(O) (50 μg/mouse) complex or HEL-MB-ODN4 531-liposome complex on three occasions at 10 day intervals. After 10 days, blood was obtained by heart punching method and the sera were collected through blood cell precipitation by centrifugation. From the collected sera, the titer of anti-HEL antibodies (total IgG, IgG1, IgG2a) was analyzed by ELISA.

<4-2> ELISA

The mice were sacrificed 10 day after the injection. Sera were collected from the mice and then stored at −70° C. To measure the IgG, IgG1, and IgG2a titer, we coated the 96-well immunoplates (Nalgen Nunc International) with 10 μg/ml of HEL, and then blocked them with PBST containing 1% BSA. The sera were added to the top row of each plate, and serial 1:3 dilutions of PBST were then placed into subsequent rows. We incubated the plates for 4 h at room temperature and washed them with PBST. Next, we added goat anti-mouse IgG antibody-, anti-mouse IgG1 antibody-, or anti-mouse IgG2a antibody-conjugated with horseradish peroxidase and incubated the plates for 2 h. The colorimetric assay was developed with 1-Step ABTS (Pierce Biotechnology Inc., Rockford, Ill., USA), and we used a Labsystems Multiskan microplate reader (GMI Inc., Ramsey, Mich., USA) to measure the absorbance at 405 nm (19).

The humoral immune response of the BALB/c mice intraperitoneally immunized by HEL-MB-ODN 4531 and liposome complex were investigated. The injection of HEL-MB-ODN4531-liposome complex increase the amount of antibodies greater than the injection of HEL only, HEL-MB-ODN 4531 mixture or HEL-liposome complex which confirmed the immunoadjuvant effect of a MB-ODN 4531-liposome complex in humoral immune responses. Incomplete Freund's adjuvant is a representative immunoadjuvant which has been used since 60 years ago. But it has a limitation that it induces no cellular immunostimulatory effect and cannot be applied to humans. MB-ODN 4531-liposome complex proved to act as an immunoadjuvant increasing humoral immunity as well as inducing cellular immune responses through stimulating immune cells. In addition, MB-ODN 4531-liposome complexes are effective in Th1-immune response-specific IgG2a antibody production.

<4-3> Mice and Immunization

Mice were maintained under specific-pathogen-free conditions. Four-week-old male BALB/c (H-$2^b$) mice were purchased from Central Lab. Animal Inc. (Seoul, Korea). The present inventor's animal studies were approved by the Institutional Animal Care and Use Committee of Hallym University.

The mice were injected i.p. with the peptide (50 μg/mouse)-CpG-DNA (MB-ODN 4531)-liposome complex on three or four occasions at 10 day intervals.

<4-4> Antigen-Specific Ig ELISA

The mice were sacrificed 10 day after the injection. Obtained sera were diluted to 1:10 with PBS/0.2% sodium azide and then stored at −20° C. To measure the total amount of IgG, IgG1 and IgG2a, we coated the 96-well immunoplates (Nalgen Nunc International, Rochester, N.Y., USA) with 10

µg/ml of each peptide and then blocked them with 0.05% of Tween 20 in PBS (PBST) containing 1% BSA. The sera were diluted to 1:400 with PBS and added to the wells of each plate.

For detection of the total IgG, IgG1 and IgG2a, we used biotin-conjugated rat anti-mouse IgG antibody, rat anti-mouse IgG1 antibody and rat anti-mouse IgG2a antibody (BD Pharmingen, San Diego, Calif., USA) at a dilution of 1:5,000.

To measure the titer of IgG, IgG1 and IgG2a, we coated the 96-well immunoplates (Nalgen Nunc International, Rochester, N.Y., USA) with 10 µg/ml of each protein or peptide, and then blocked them with PBST containing 1% BSA. The sera were added to the top row of each plate, and serial 1:3 dilutions of PBST were then placed into subsequent rows. We incubated the plates for 2 h at room temperature and washed them with PBST. Next, we added biotin-conjugated rat anti-mouse IgG antibody, rat anti-mouse IgG1 antibody or rat anti-mouse IgG2a antibody and incubated the plates for 2 h. After 3 times wash, the streptavidin conjugated with HRP (horseradish peroxidase) was added to the plate followed by 1 h incubation. Colorimetric analysis was performed using TMB solution (KPL, Gaithersburg, Md., USA), and spectrophotometer (Spectra Max250, Molecular Devices, Downingtown, Pa., USA) was used to analyze absorption at 450 nm.

Example 5

Screening of Epitopes Using CpG-DNA-H5N1 (or Other Influenza Strains) HA Peptide-Liposome Complex <5-1> Immunization of CpG-DNA-H5N1 (or Other Influenza Strains) HA Peptide-Liposome Complex Candidate epitopes (Table 2-Table 9) were selected from HA (hemagglutinin) protein of various influenza A viruses considering hydrophilicity, hydrophobicity, secondary structure, antigenicity and amphiphilicity to prepare CpG-DNA-peptide-liposome complex as described in Example 3. Prepared CpG-DNA-peptide-liposome complexes (50 µg/mouse) were i.p. injected to BALB/c mice on three occasions at 10 day intervals. After 10 days, blood was obtained by heart punching method and the sera were collected through blood cell precipitation by centrifugation. From the collected sera, the titers and amounts of anti-peptide antibodies (total IgG, IgG1, IgG2a) was analyzed by ELISA.
<5-2> ELISA The mice were sacrificed 10 day after the injection. Obtained sera were diluted to 1:10 with PBS/0.2% sodium azide and then stored at −20° C. Each selected peptide (10 µg/ml, sodium bicarbonate buffer, pH 9.6) were added to the 96-well immunoplates (Nalgen Nunc International, Rochester, N.Y., USA) and left for 16 h at 4° C. And then the amounts and the titers of total IgG (FIGS. 2a, 2d, 2e, 5a, 5d, 6a, 6d and 7), IgG1 (FIGS. 2b, 2e, 5b, 6b and 7), IgG2a (FIGS. 2c, 2e, 5c, 6c and 7), which specifically bind to each peptide, were analyzed as described in Example <4-4>.

Figure 1B:
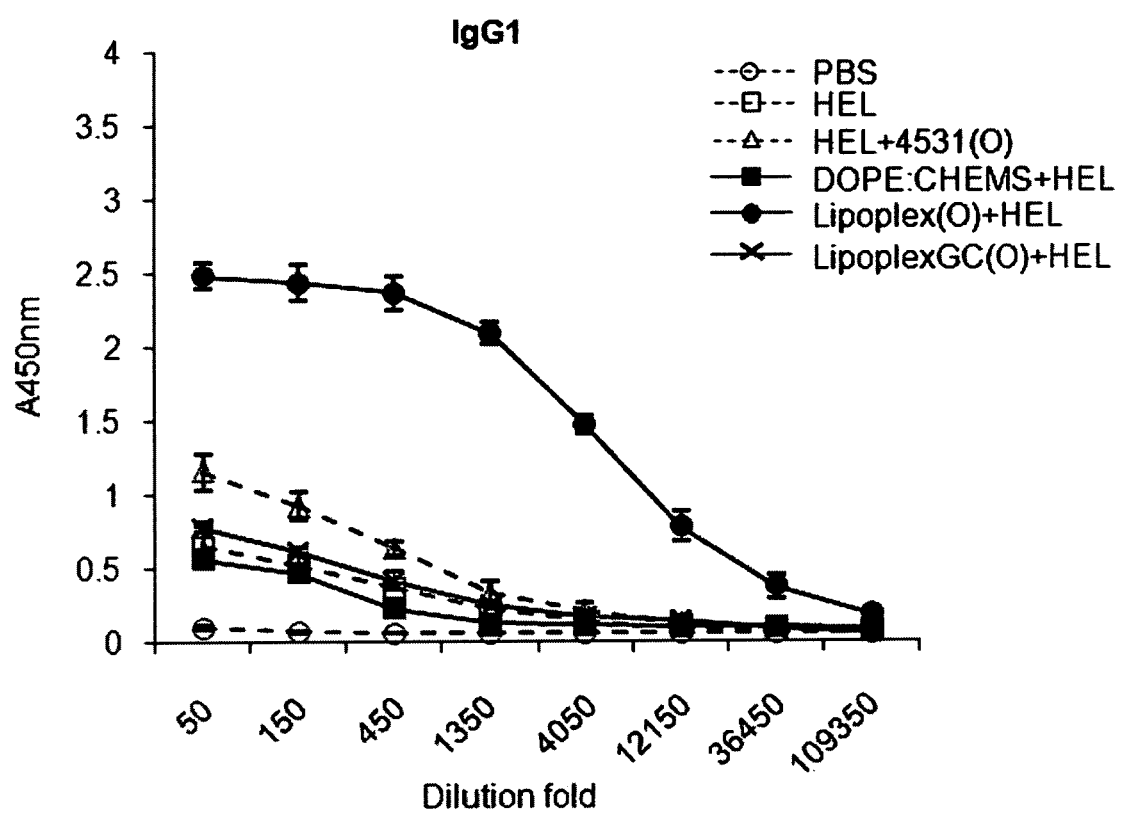
Figure 2A:
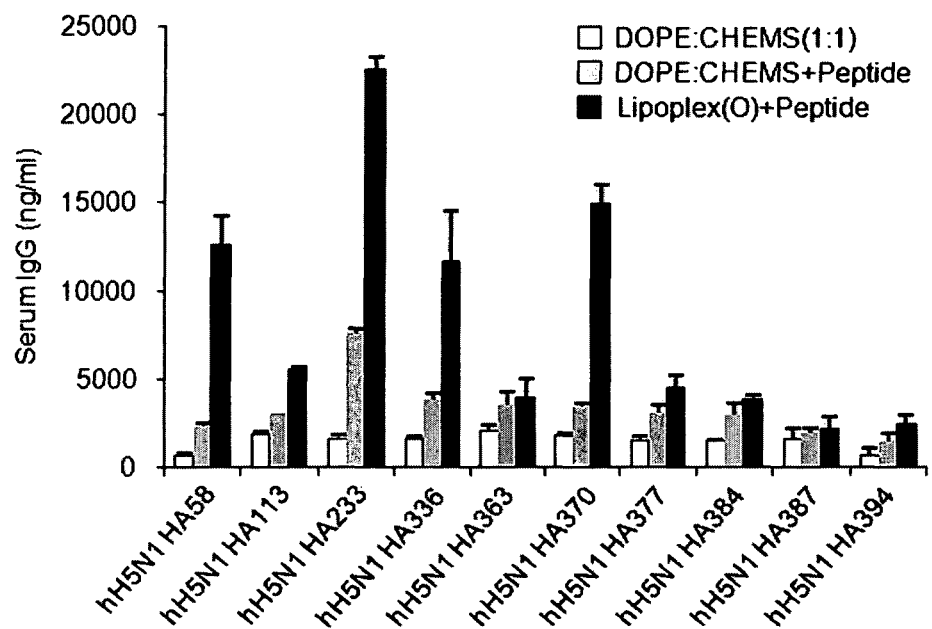
Figure 2B:
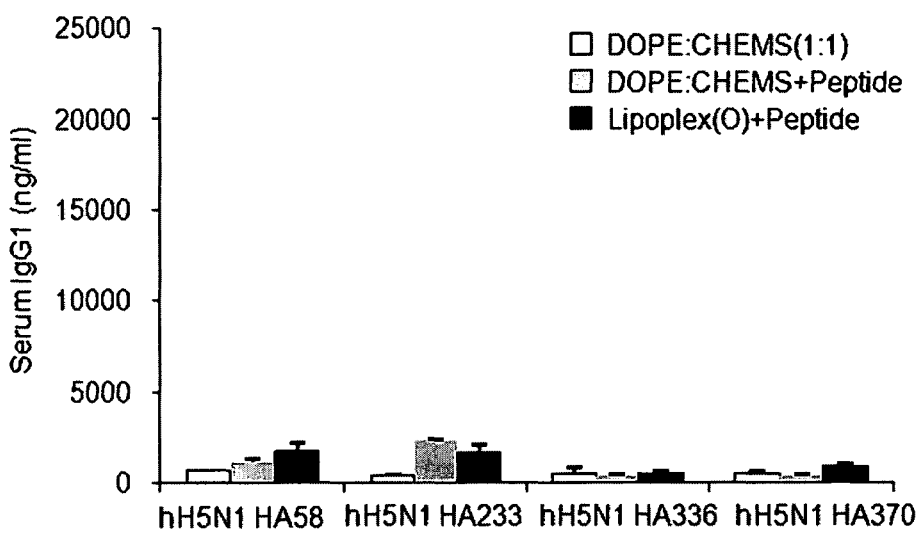
Figure 2C:
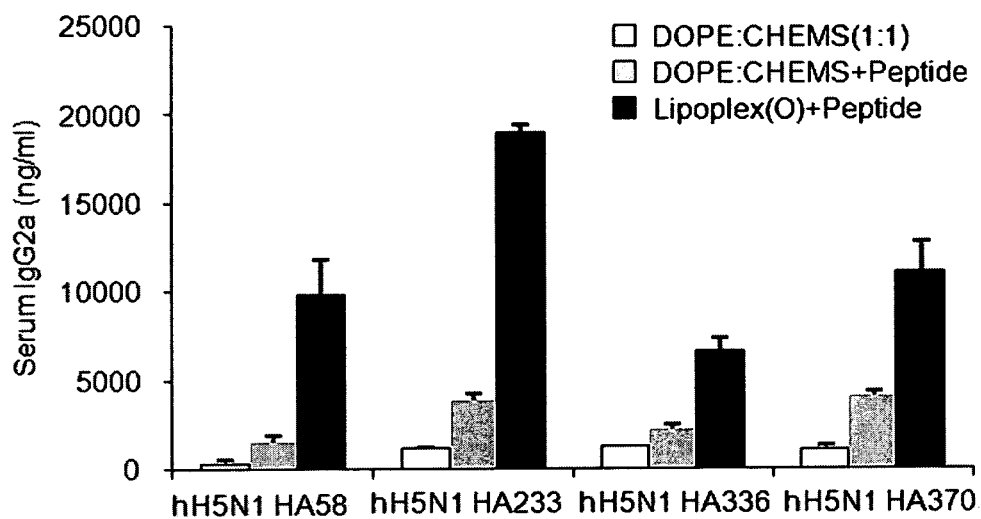
Figure 2D:
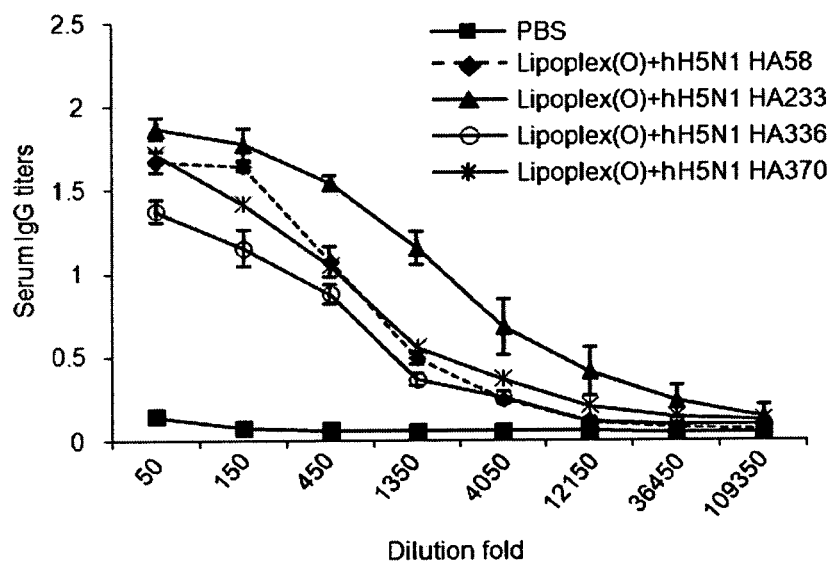
Figure 2E:
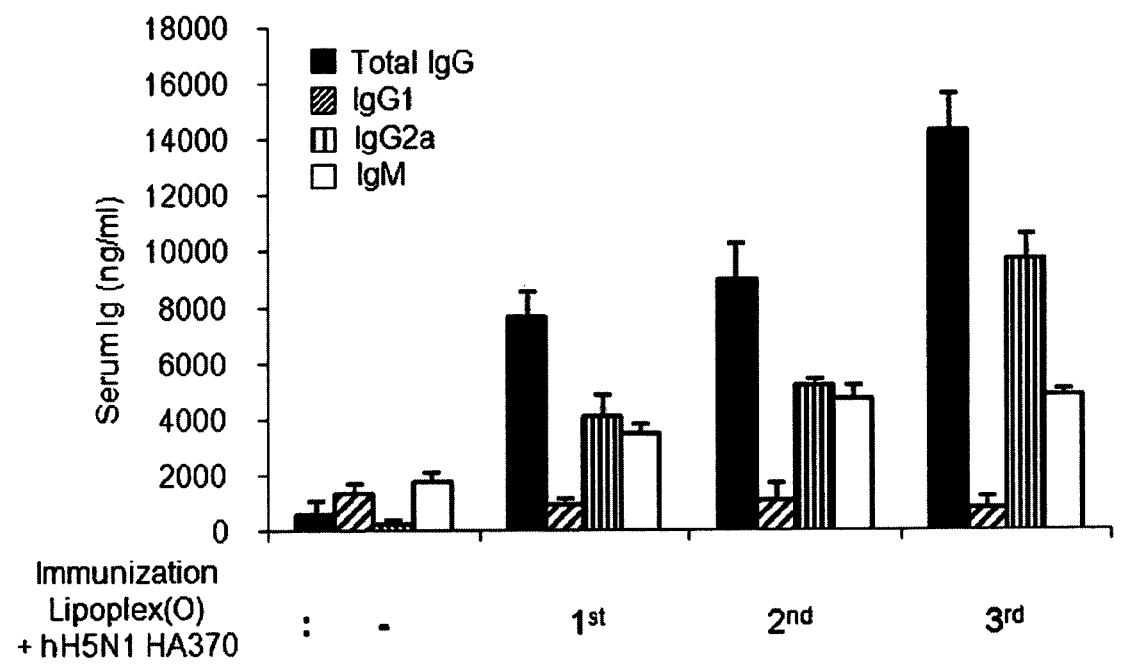
Figure 5A:
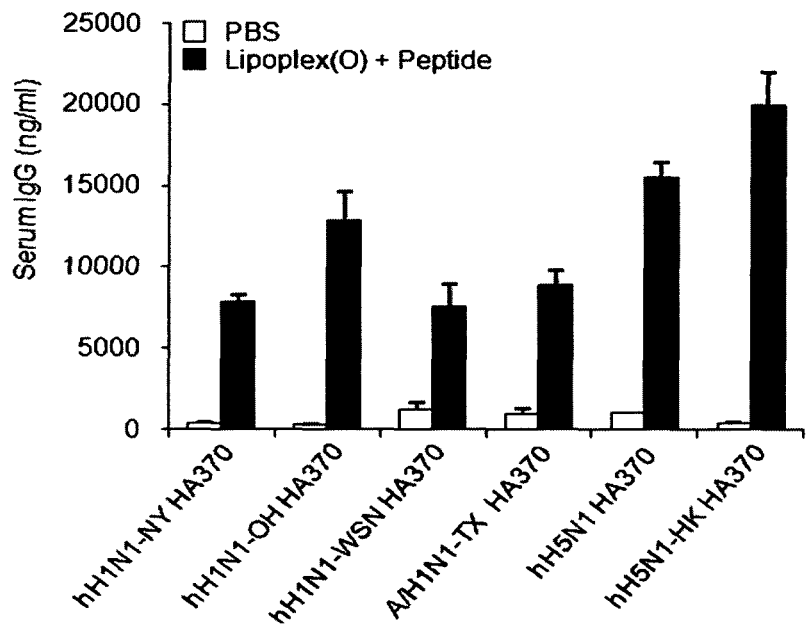
FIGS. 5a-5d represent the conserved sequences corresponding to hH5N1 HA370 epitope in H1N1 strains and H5N1 strains and the conserved sequence-specific IgG production. The 17 amino acid long conserved sequences in H1N1 strains and H5N1 strains corresponding to hH5N1 HA370 epitope of A/Vietnam/1203/2004 strain were synthesized as described in Table 3 and Table 4. Five BALB/c mice were immunized i.p. three times at 10 day intervals with 50 µg of each peptide (hH1N1-NY HA370, hH1N1-OH HA370, hH1N1-WSN HA370, A/H1N1-TX HA370, hH5N1 HA370, and hH5N1-HK HA370) and 50 µg of MB-ODN 4531(O) coencapsulated in DOPE:CHEMS (1:1 ratio) complex (represented as Lipoplex(O)+peptide). The antisera were collected 10 day after final immunization, and then amounts of anti-each peptide-specific total IgG (FIG. 5a), amounts of anti-each peptide-specific IgG1 (FIG. 5b), amounts of anti-each peptide-specific IgG2a (FIG. 5c) and titers of anti-each peptide-specific IgG (FIG. 5d) were assayed by an ELISA.
Figure 5B:
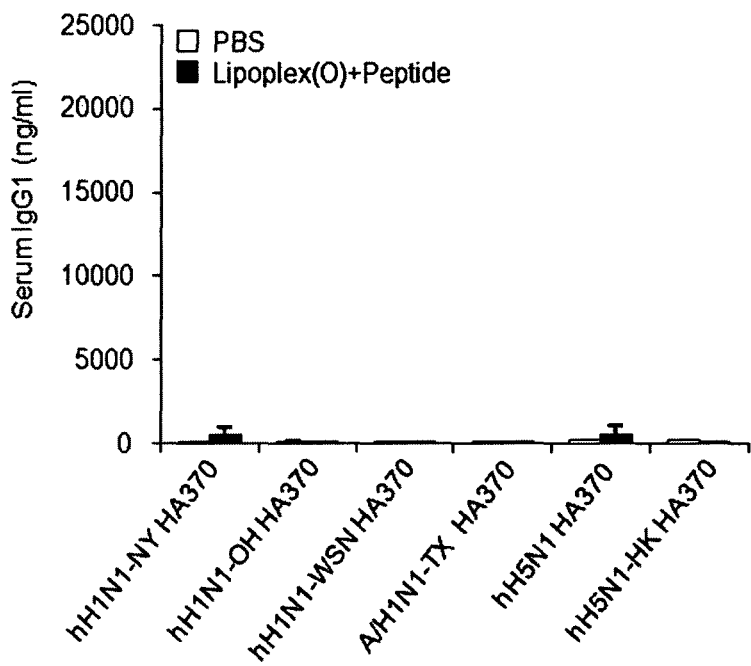
Figure 5C:
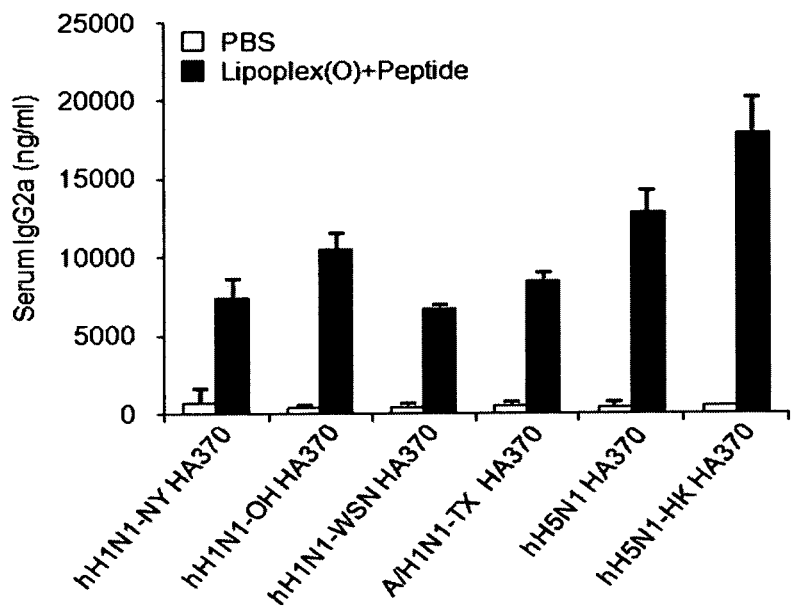
Figure 5D:
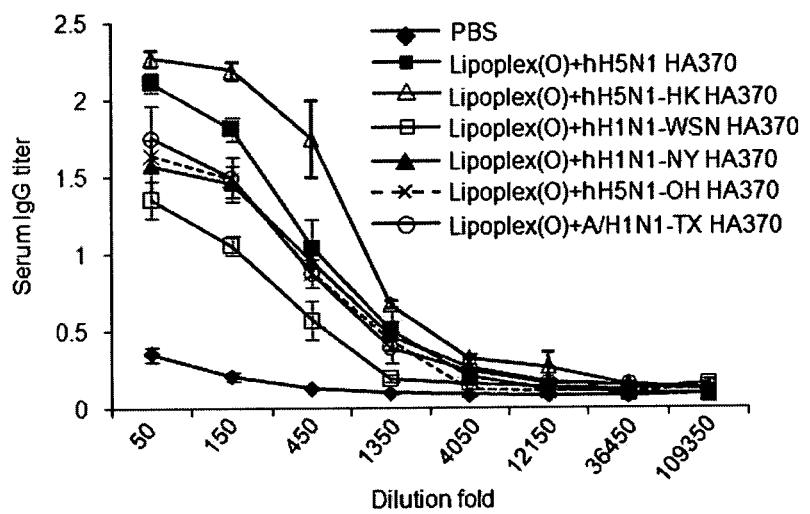
Figure 6A:
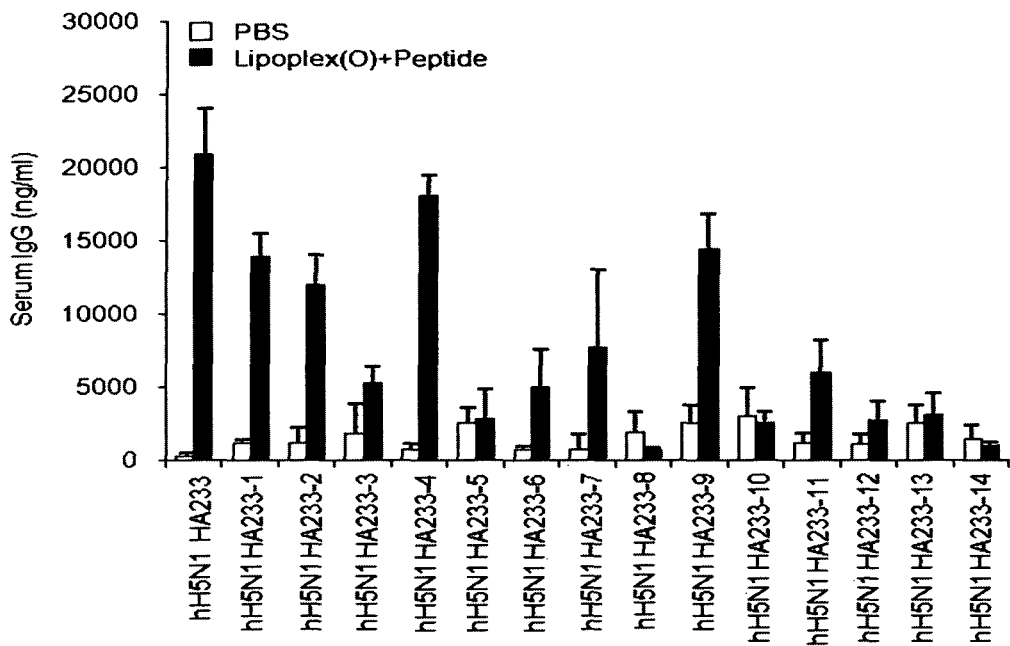
Figure 6B:
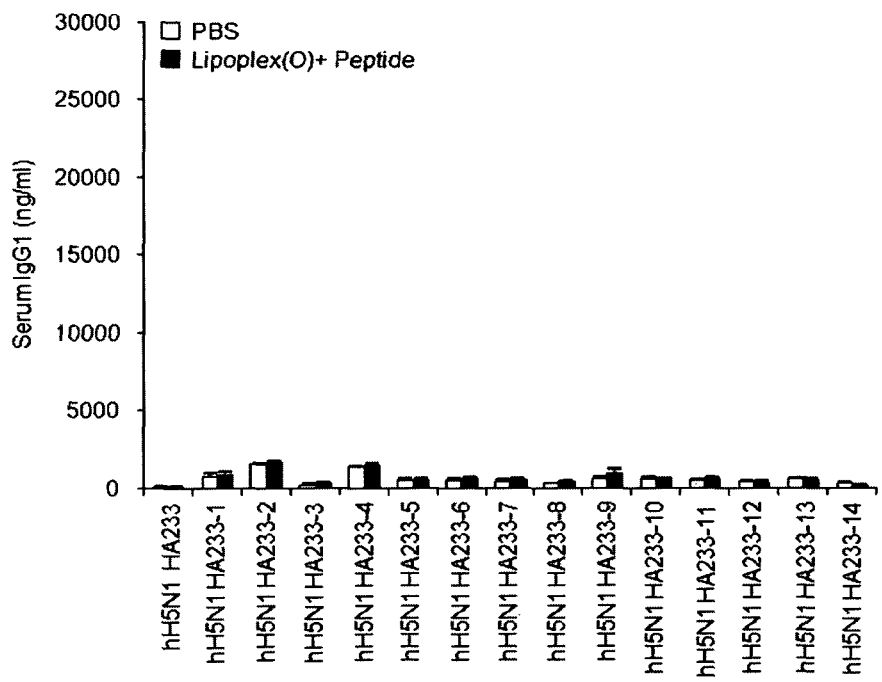
Figures 6C, 6D:
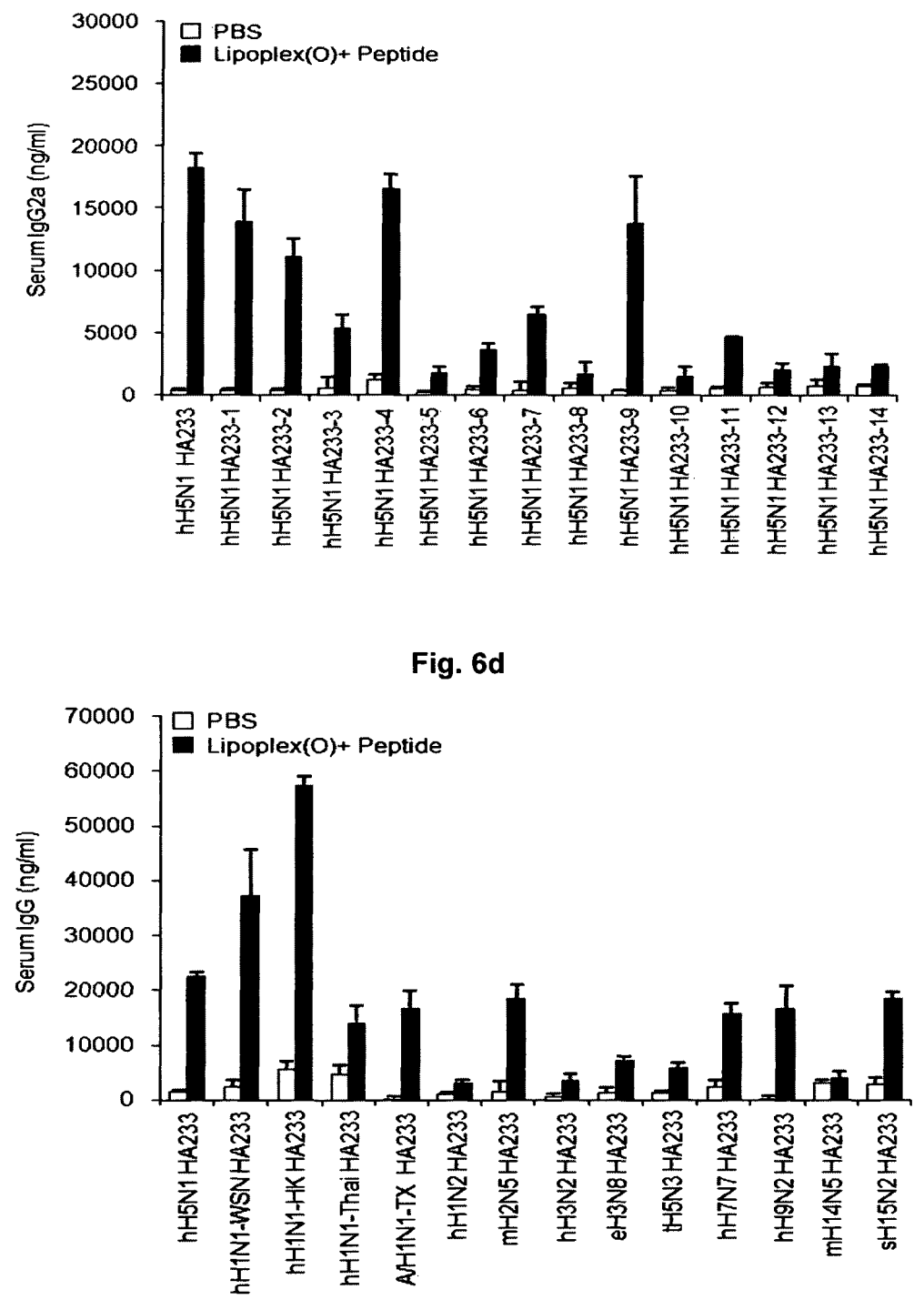

Among the peptides selected from avian influenza A (H5N1)/Vietnam/2004 strain HA protein, hH5N1 HA58, hH5N1 HA233, hH5N1 HA336 and hH5N1 HA370 increased the amount and the titer of total IgG (FIG. 2a, 2d) and IgG2a (FIGS. 2c). And H1N1 peptide corresponding to hH5N1 HA370 peptide (hH1N1-NY HA370, hH1N1-OH HA370, hH1N1-WSN HA370, A/H1N1-TX HA370) and hH5N1-HK HA370 peptide existing in H5N1 viruses (Table 3, Table 4) increased the amount and the titer of total IgG (FIG. 5a, 5d). In addition, production of IgG2a related to Th1 immune responses was also increased (FIG. 5c). Furthermore, hH5N1 HA233-1, hH5N1 HA233-2, hH5N1 HA233-3, hH5N1 HA233-4, hH5N1 HA233-6, hH5N1HA233-7, hH5N1 HA233-9 and hH5N1 HA233-11 peptides, existing in H5N1 virus strains corresponding to hH5N1 HA233 peptide (Table 5) and hH1N1-WSN HA233, hH1N1-HK HA233, hH1N1-Thai HA233, A/H1N1-TX HA233, mH2N5 HA233, hH7N7 HA233, hH9N2 HA233, sH15N2 HA233 peptides, existing in various influenza A virus strains corresponding to hH5N1 HA233 peptide (Table 6) increased the amount of total IgG (FIG. 6d).

Figure 7A:
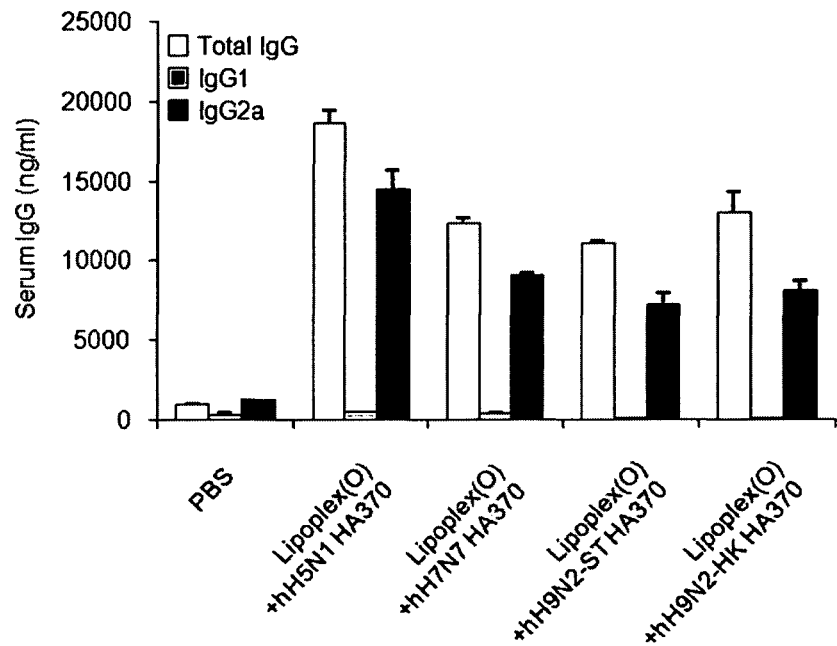
FIGS. 7a-7b represent the effect of conserved sequences corresponding to hH5N1 HA370 (FIG. 7a) (or hH5N1 HA233.
Figure 7B:
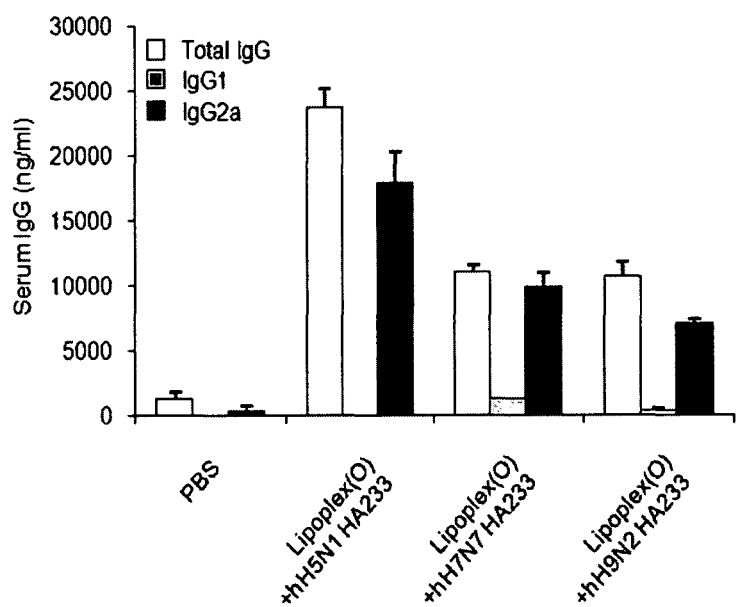

Also, hH7N7 HA370, hH9N2-ST HA370 and hH9N2-HK HA370 peptide existing in H7N7 and H9N2 viruses corresponding to hH5N1 HA370 peptide (Table 9) increased the amount of total IgG (FIG. 7a). hH7N7 HA 233 and hH9N2 HA233 peptides existing in H7N7 and H9N2 viruses corresponding to hH5N1 HA233 peptide (Table 6) increased the amount of total IgG (FIG. 7b).

Example 6

Figure 3B:
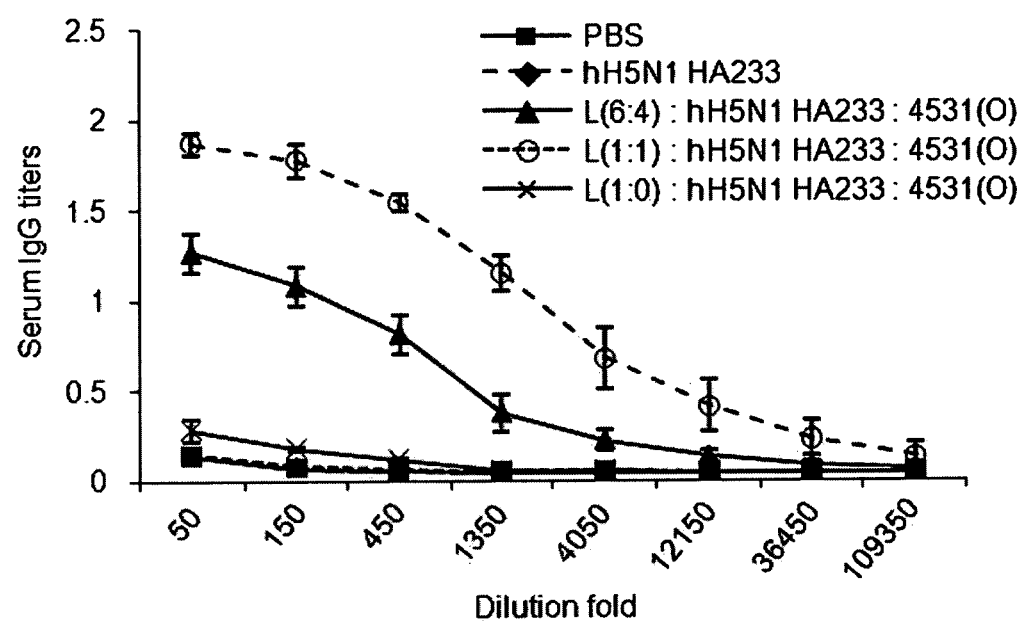

Induction of Humoral Immune Response by CpG-DNA-Peptide-Liposome Complex Depending on the Kinds of Liposomes and CpG-DNAs The MB-ODN 4531-peptide (hH5N1 HA233) was complexed with various liposomes (DOPE:CHEMS (6:4, 1:1, 1:0 and 0:1), lipofectin, lipofectamine, DOTAP and poloxamer 407) as described in Example 3 and i.p. injected to BALB/c mice on three occasions and the sera were collected as described in Example <4-3>. As the results of measuring the amount of hH5N1 HA233 peptide-specific total IgG (FIG. 3a), it was highest at the molar ratio of DOPE:CHEMS (1:1). The titer of H5N1 HA233 peptide-specific total IgG was also highest at the molar ratio of DOPE:CHEMS (1:1) (FIG. 3b).

Peptide (hH5N1 HA233)-liposome (DOPE:CHEMS (1:1)) and various PO-DNAs or PS-DNAs represented in Table 1 were complexed as described in Example 3 and i.p. injected to BALB/c mice on three occasions and then the sera were collected as described in Example <4-3>. As the results of measuring the amount of H5N1 HA233 peptide-specific total IgG, the amount was highest when the complex of PO-DNA MB-ODN 4531(O) and PS-DNA MB-ODN 4531(S) were used (FIG. 4). These results indicate that CG sequence of PO-DNA or PS-DNA plays a significant role.

Example 7

Analysis of Hemagglutination-Inhibition and Virus Neutralization of Antibodies Produced by CpG-DNA-Peptide-Liposome Complex <7-1> Recombinant H5N1 Virus Gene segments of A/Vietnam/1203/2004 (H5N1) and A/Puerto Rico/8/34 (PR8) (H1N1) influenza viruses were cloned into plasmids for virus rescue and gene reassortment by eight-plasmid reverse genetics method (36). Viruses so derived were propagated in the allantoic cavities of 10-d-old embryonated chickens' eggs. These reassortant viruses include "PR8/H5Lo," which bears the HA gene segment of avian-lineage A/Vietnam/1203/2004 and seven complementary gene segments of PR8.
<7-2> Hemagglutination-Inhibition Assay Hemagglutination-inhibition assay was performed as described previously (37). Briefly, viruses were diluted to 4 HA units and incubated with an equal volume of serial two-fold dilutions of receptor-destroying enzyme-treated serum samples for 1 h at room temperature. An equal volume of 0.5% chicken red blood cells was added to the wells and incubated for 30 min to measure the HI titers.

<7-3> Virus Neutralization Assay

Virus neutralization assay in MDCK cells was performed as described previously (38). Approximately 100 PFU/ml of influenza viruses (the rH5N1 virus and A/WSN/1933) were incubated with an equal volume of heat-inactivated twofold serially diluted serum samples at 37° C. for 1 h. After incubation, the mixtures were added to a confluent monolayer of MDCK cells in a minimum essential medium supplemented with 10% FBS and TPCK (L-tosylamido-2-phenyl) ethyl chloromethyl ketone, 1 μg/ml)-treated trypsin. The cells were cultured for 72 h before the determination of the cytopathic effect. The neutralization percentage was calculated by means of the following equation: Neutralization (%, percent inhibition)=[(plaque no. of the virus only treated−plaque no. of serially diluted serum mixed virus)/plaque no. of the virus only treated]×100.

Figure 8A:
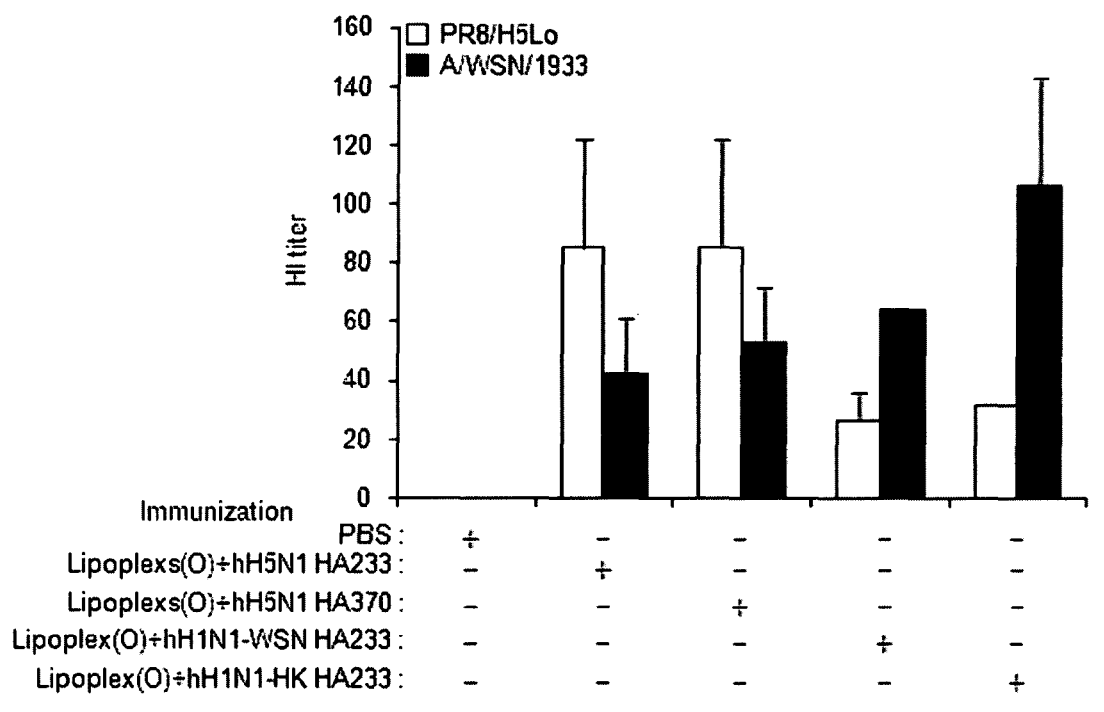

The PO-DNA-peptide (hH5N1 HA233, hH5N1 HA370, hH1N1-WSN HA233 or hH1N1-HK HA233) was complexed with liposome (DOPE:CHEMS) as described in Example 3 and i.p. injected to BALB/c mice on three occasions and the sera were collected as described in Example <4-3>. It was confirmed that hH5N1 HA233, hH5N1 HA370, hH1N1-WSN HA233 or hH1N1-HK HA233 peptide-specific antibodies inhibited the hemagglutination induced by rH5N1 virus PR8/H5Lo and A/WSN/1933 virus (FIG. 8a).

Figure 8B:
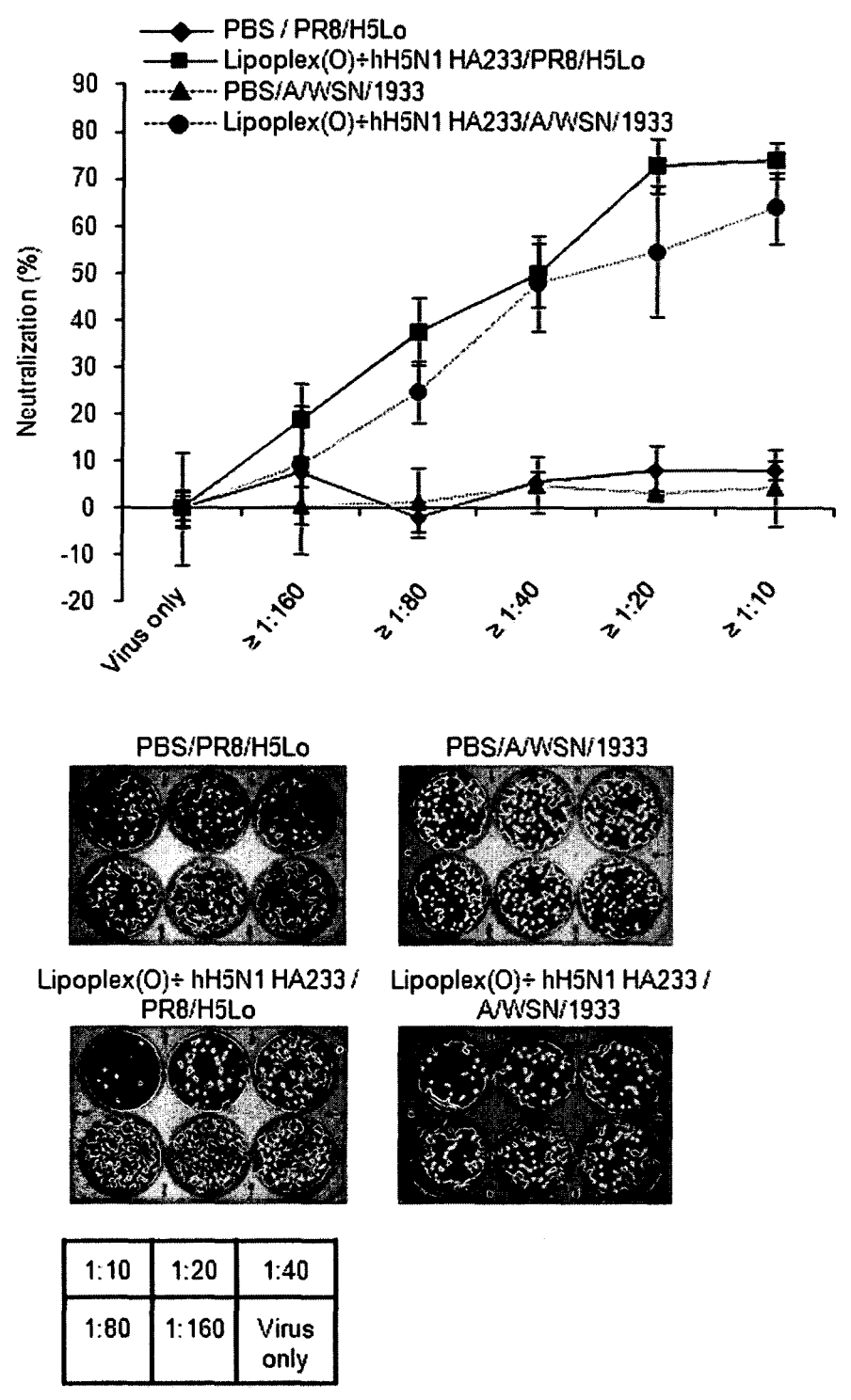

The PO-DNA-peptide (hH5N1 HA233, hH5N1 HA370, hH1N1-WSN HA233, hH1N1-HK HA233 or A/H1N1-TX HA233) was complexed with liposome (DOPE:CHEMS) as described in Example 3 and i.p. injected to BALB/c mice on three occasions and the sera were collected as described in Example <4-3>. The hH5N1 HA233 peptide-specific antibody was treated in advance with the rH5N1 virus PR8/H5Lo and A/WSN/1933 (FIG. 8b) and then infected with MDCK cells. It was confirmed that the titer of the viruses was low and that the hH5N1 HA233 peptide-specific antibody neutralized the viruses.

Figure 8C:
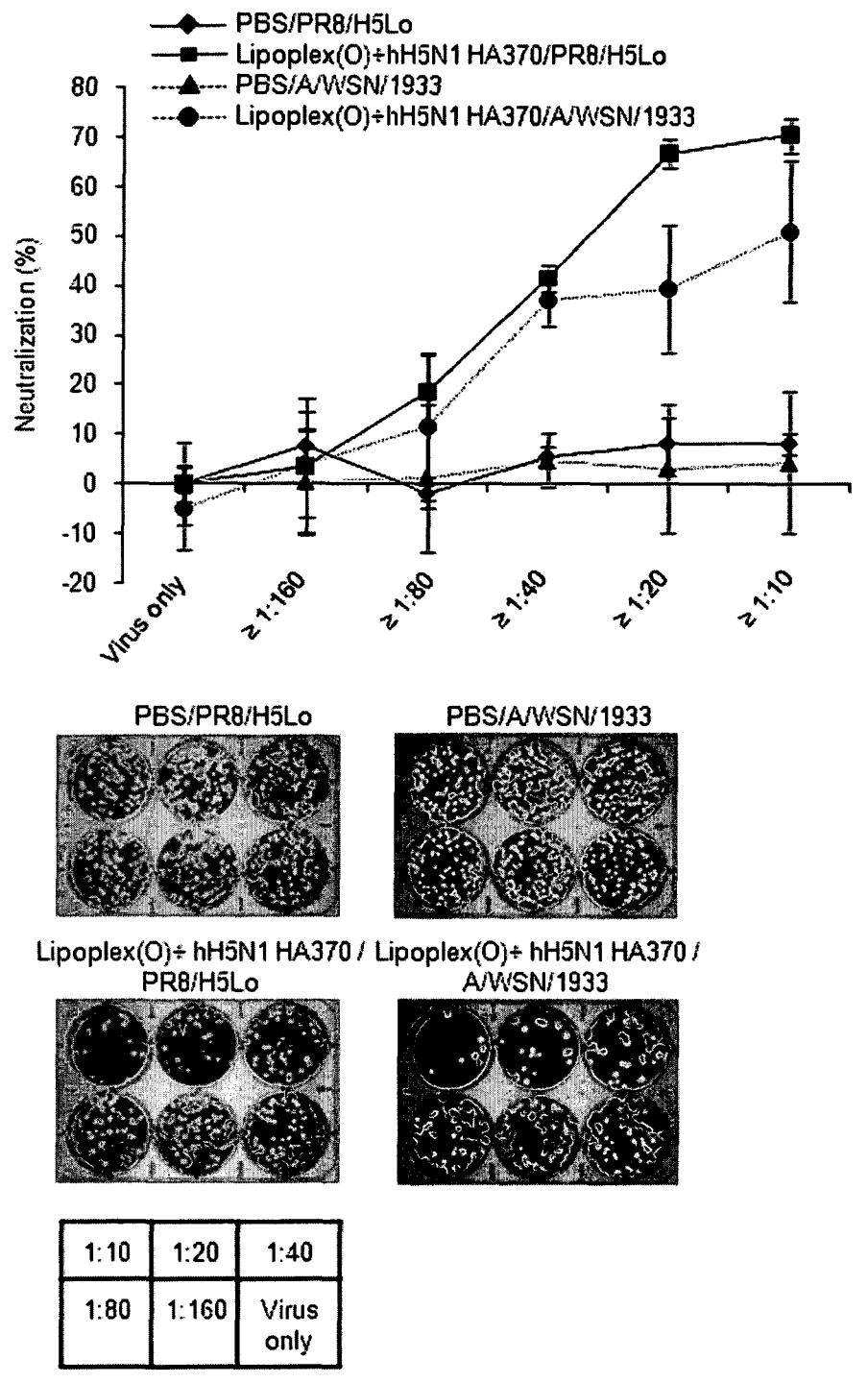

The hH5N1 HA370 peptide-specific antibody was treated in advance with the rH5N1 virus PR8/H5Lo and A/WSN/1933 (FIG. 8c) and then infected with MDCK cells. It was confirmed that the titer of the viruses was low and that the hH5N1 HA370 peptide-specific antibody neutralized the viruses.

Figure 8D:
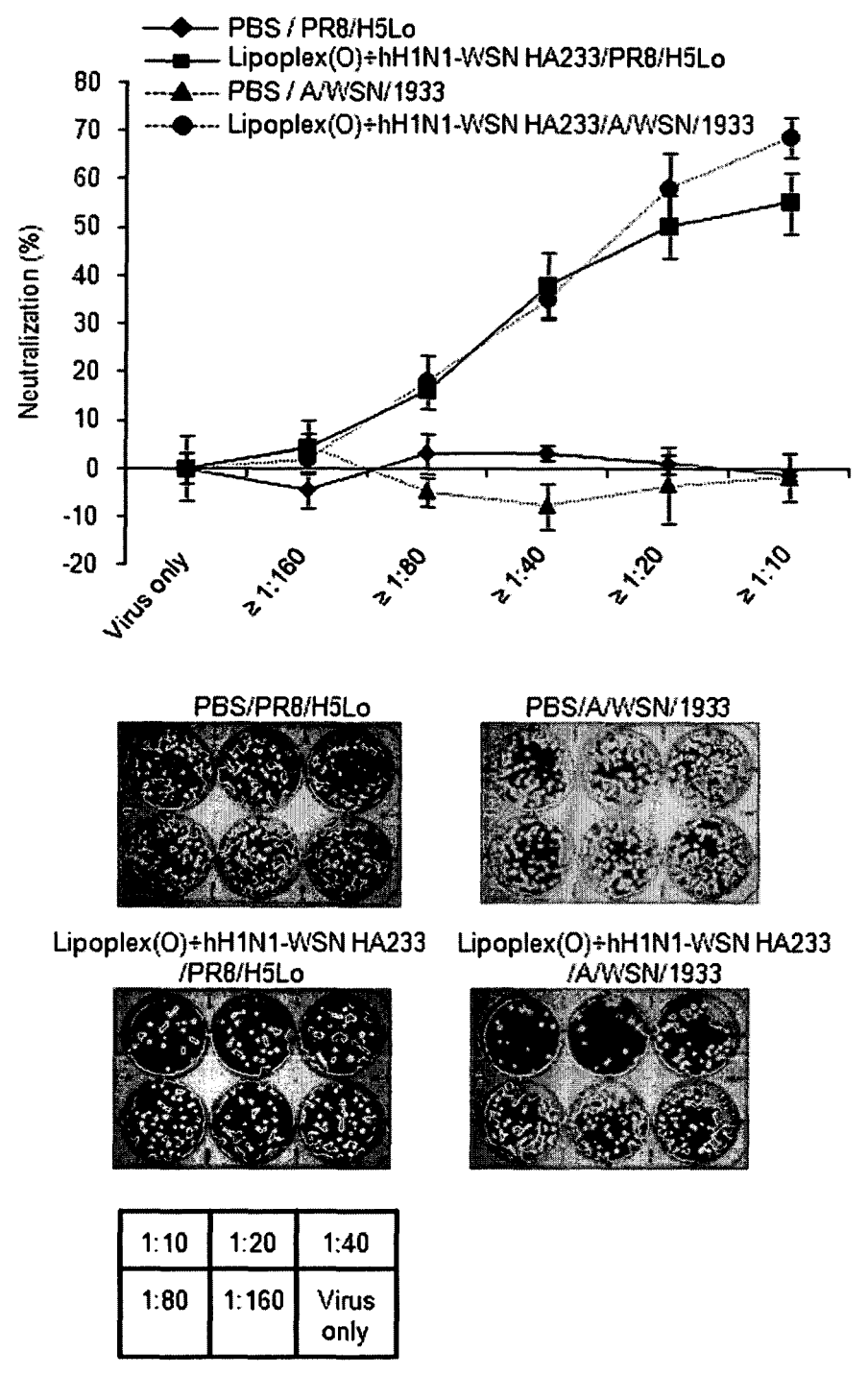
Figure 8E:
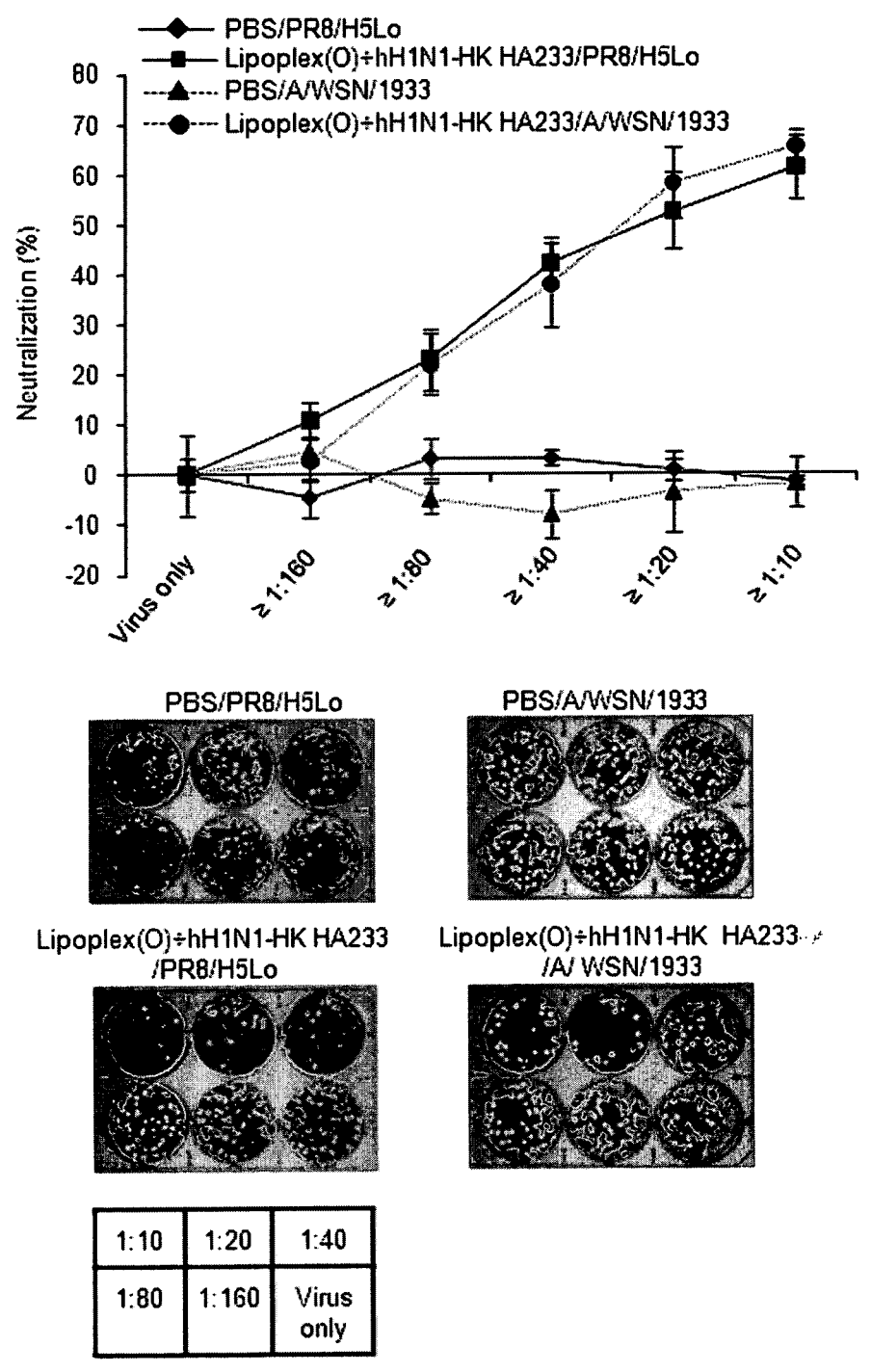

The PO-DNA-peptide (hH1N1-WSN HA233 or hH1N1-HK HA233)-liposome (DOPE:CHEMS) administered serum was treated in advance with the rH5N1 virus PR8/H5Lo and A/WSN/1933 and then infected with MDCK cells. It was confirmed that the titer of the viruses was low and that each peptide-specific antibody neutralized the viruses (FIGS. 8d and 8e).

Furthermore, the PO-DNA-peptide (A/H1N1-TX HA233)-liposome (DOPE:CHEMS) administered serum was treated in advance with the rH5N1 virus PR8/H5Lo and A/WSN/1933 and then infected with MDCK cells. It was confirmed that the titer of the viruses was low and that the A/H1N1-TX HA233 peptide-specific antibody neutralized the viruses (FIG. 8f).

Example 8

Efficacy of Vaccination of CpG-DNA-Peptide-Liposome Complex

<8-1> Vaccination and Virus Challenge Experiments

Four-week-old BALB/c mice were injected i.p. with 50 μg of peptides supplemented with 50 μg of MB-ODN 4531(O) encapsulated in DOPE/CHEMS liposomes twice at 10 day intervals. 10 days after the second immunization, the mice were inoculated intranasally challenged with 10LD50 maA/WSN/1933 or 10LD50 rH5N1 virus.

<8-2> Measurement of Weight and Survival Rate after Virus Challenge

After infection, the mice were observed daily for clinical signs and weighed. 3 days after intranasal infection of the 10LD50 rH5N1 virus, the mice began to lose their weight and died in 12 days. But the mice inoculated with PO-DNA-peptide (hH5N1 HA370, hH5N1 HA233 or hH1N1-WSN HA230)-liposome (DOPE:CHEMS) twice and then infected intranasally with the 10LD50 rH5N1 virus lost their weight until 9 days but gradually recovered and survived (FIGS. 9a, 9b, 11a, 11b, 13a and 13b).

And the mice inoculated with PO-DNA-peptide (hH5N1 HA370, hH5N1 HA233, hH1N1-WSN HA233 or hH1N1-HK HA233)-liposome (DOPE:CHEMS) twice and then infected intranasally with the 10LD50 maA/WSN/1933 virus lost their weight at first and gradually recovered and survived (FIGS. 10a, 10b, 12a, 12b, 13a, 13b, 14a and 14b).

Figures 12A, 12B:
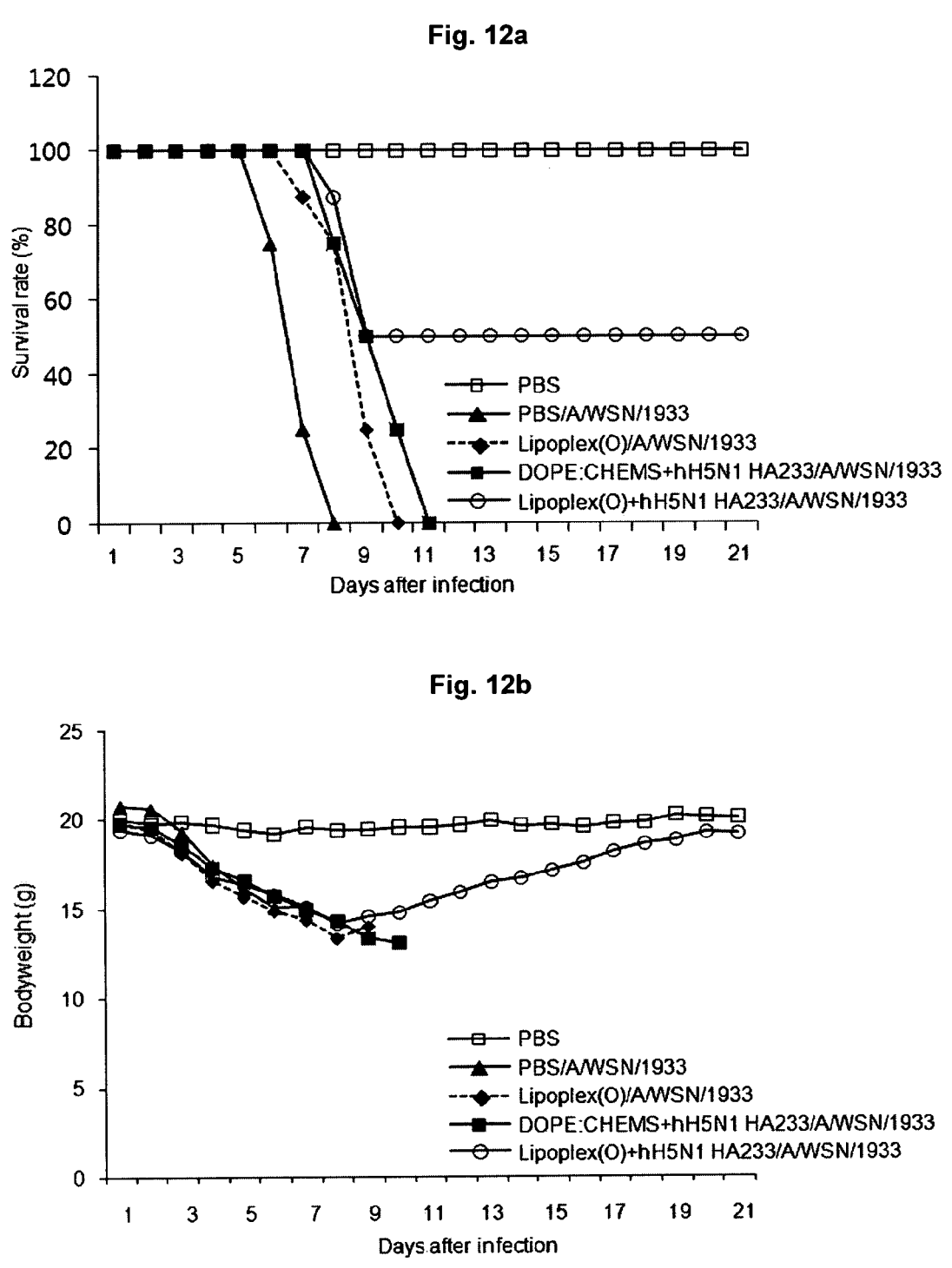

And the mice inoculated with PO-DNA-peptide (hH5N1 HA233)-liposome (DOPE:CHEMS) twice and then infected intranasally with the maA/WSN/1933 virus showed survival rate of 50% (FIG. 12a).

Figures 13A, 13B:
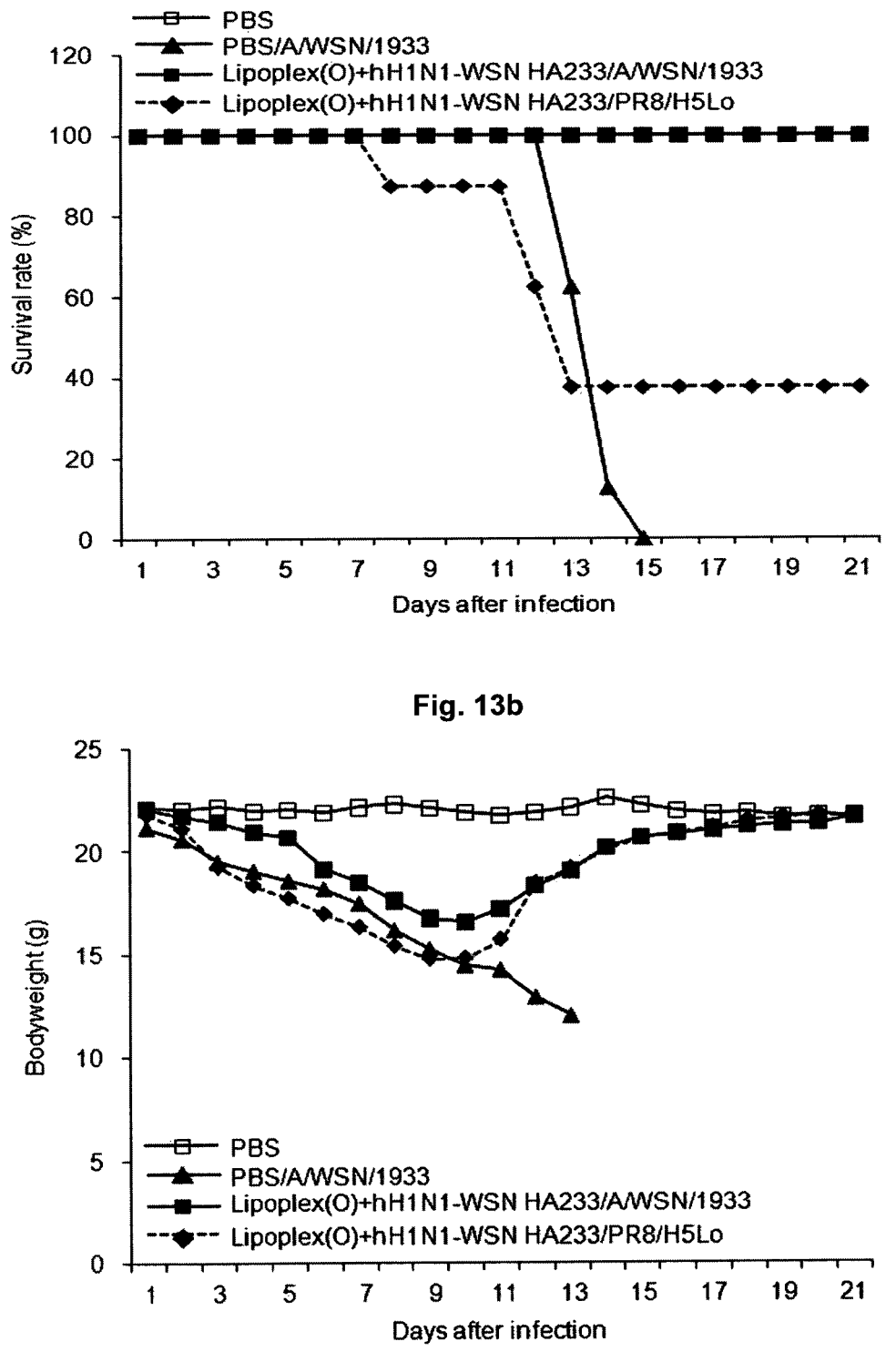

And the mice inoculated with PO-DNA-peptide (hH1N1-WSN HA233)-liposome (DOPE:CHEMS) twice and then infected intranasally with the rH5N1 virus PR8/H5Lo showed survival rate of 38% (FIG. 13a).

<8-3> Staining of Lung Tissue

Figures 9A, 9B:
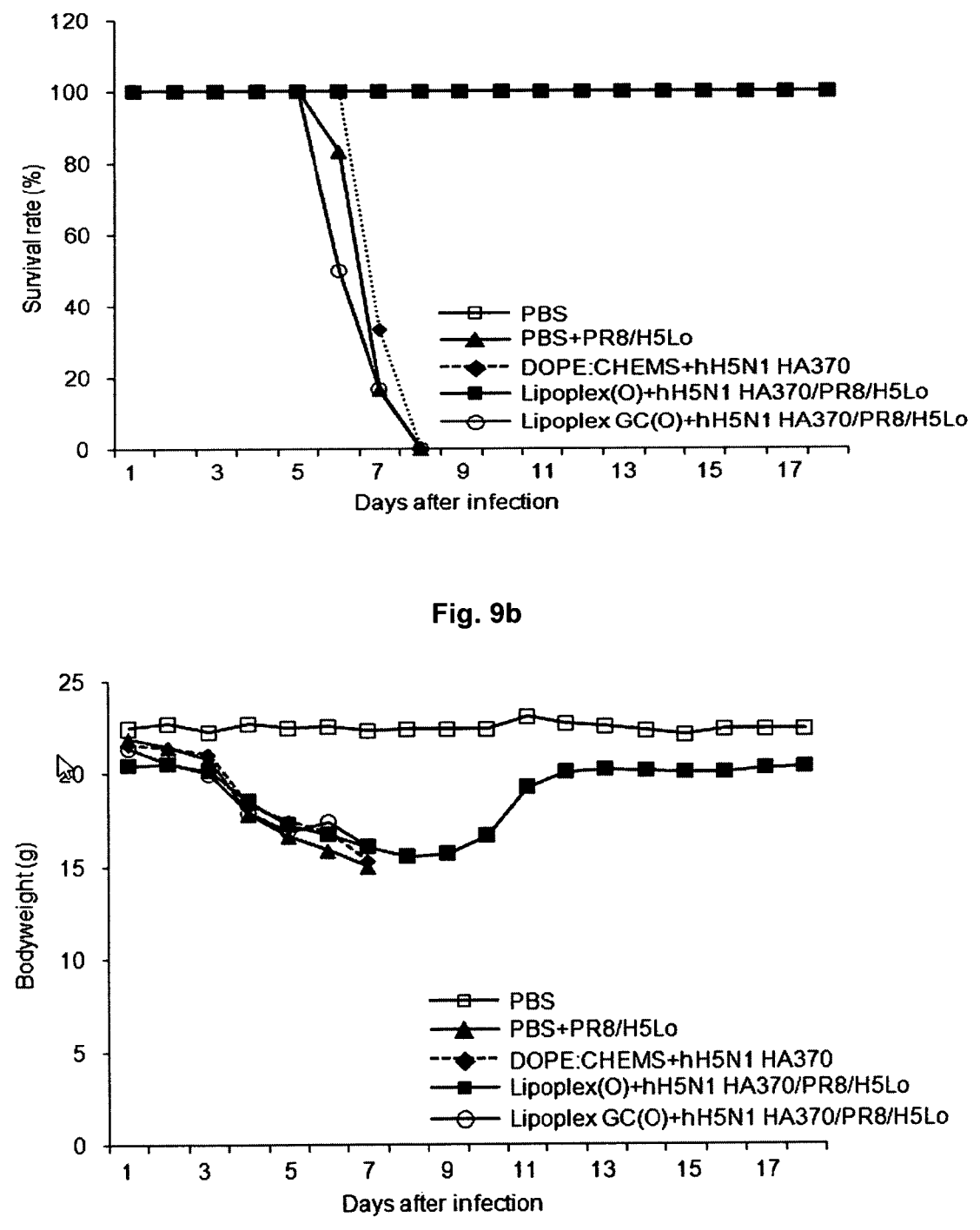
Figures 9C, 9D:
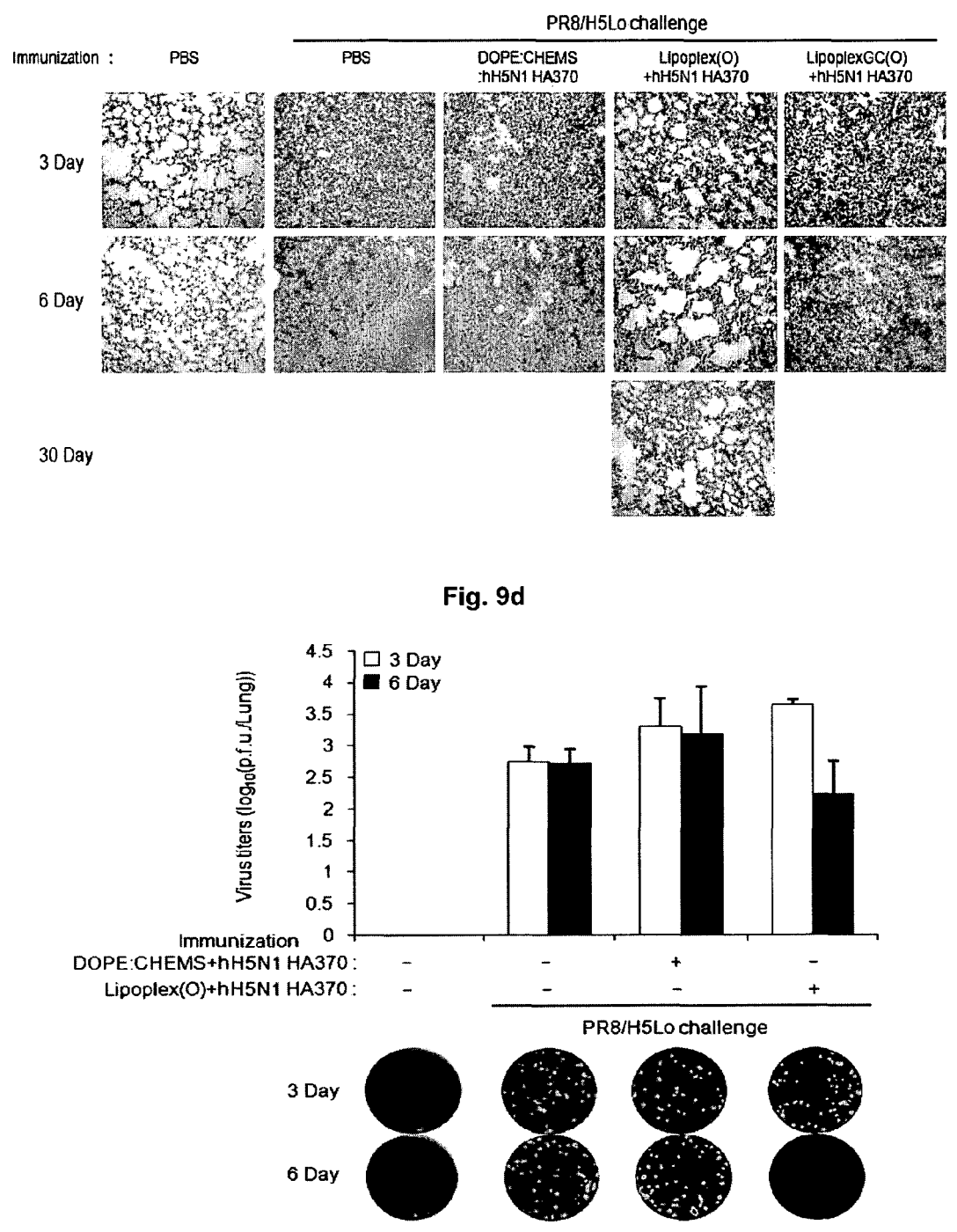
Figures 10A, 10B:
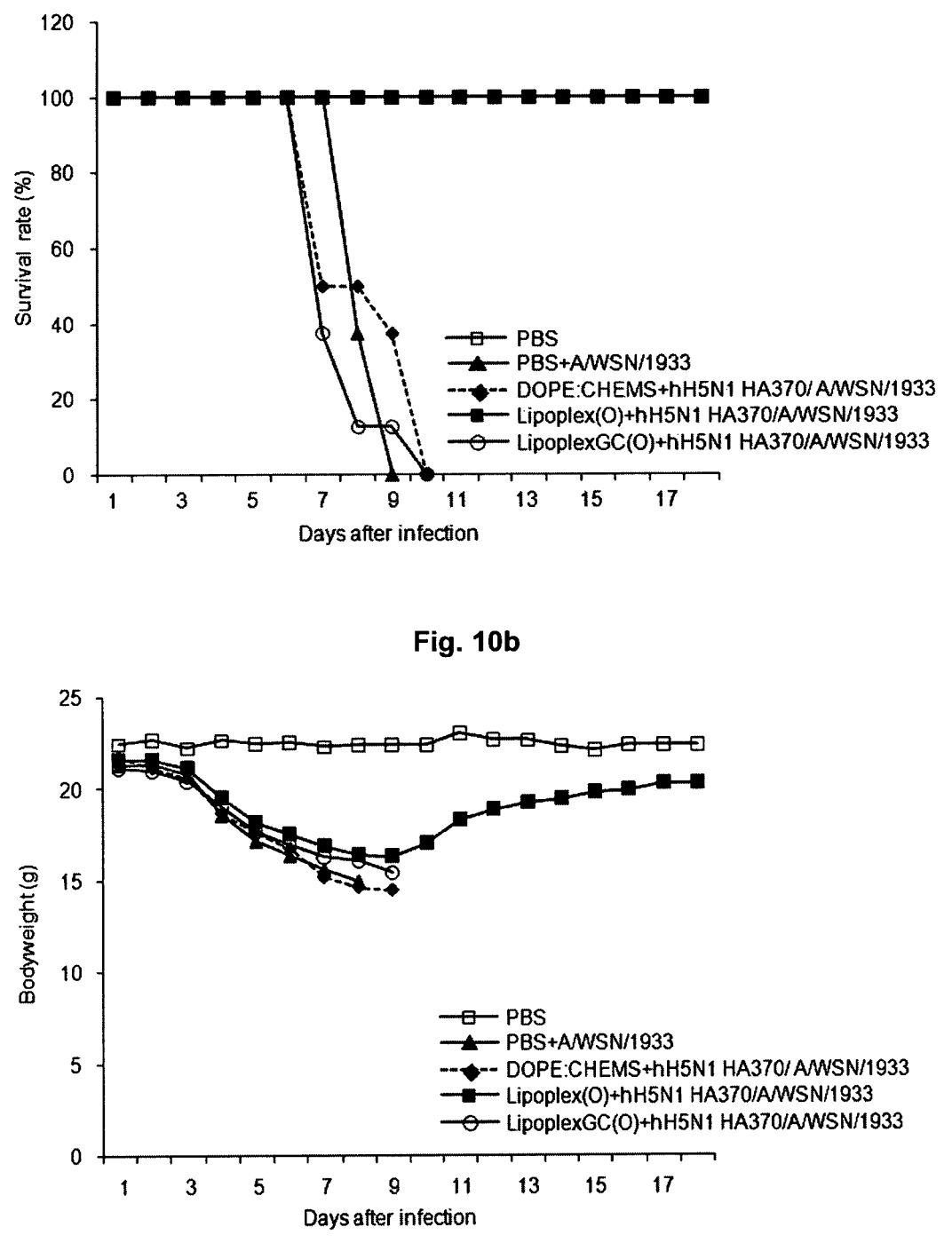
Figures 10C, 10D:
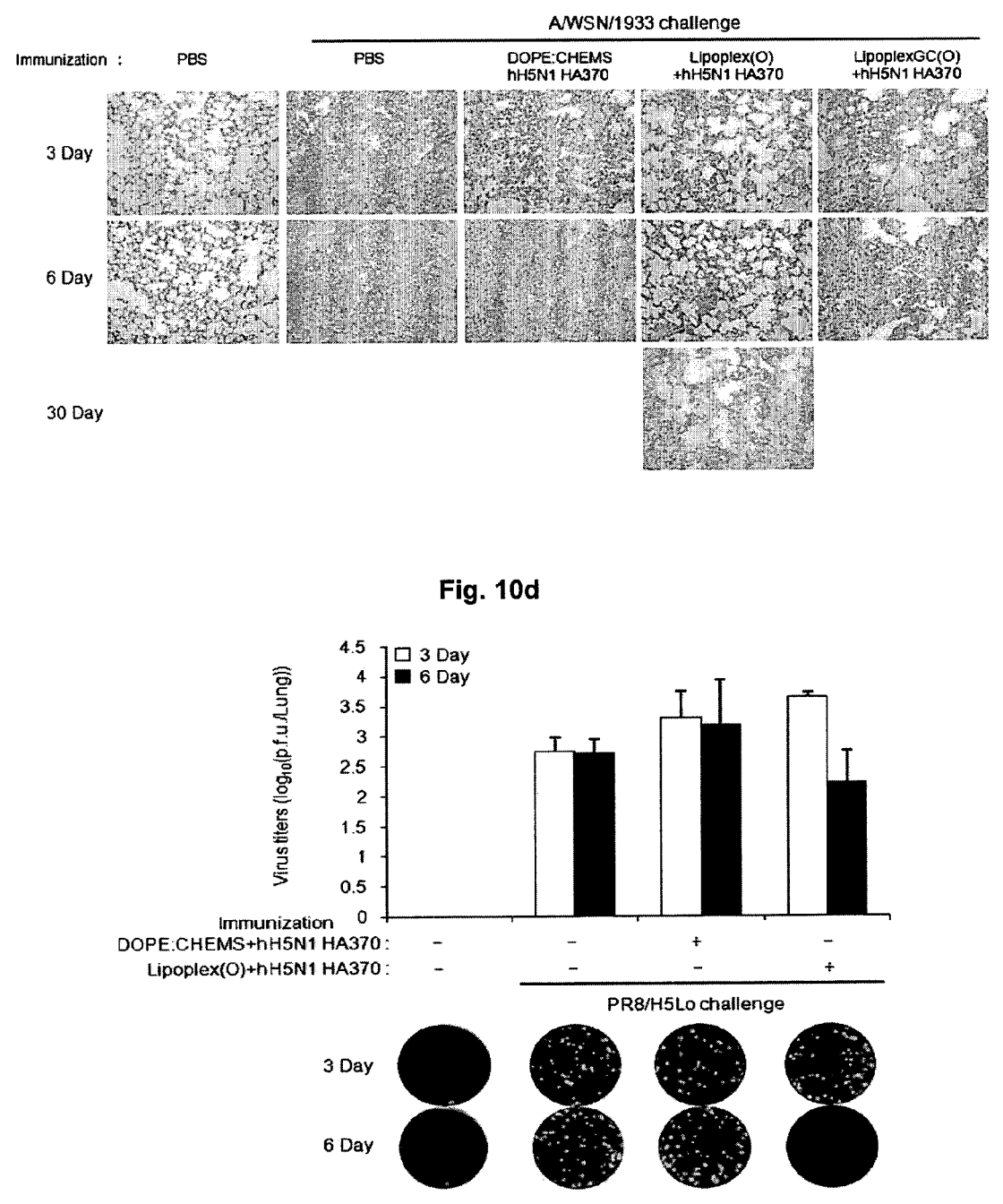
Figure 11C:
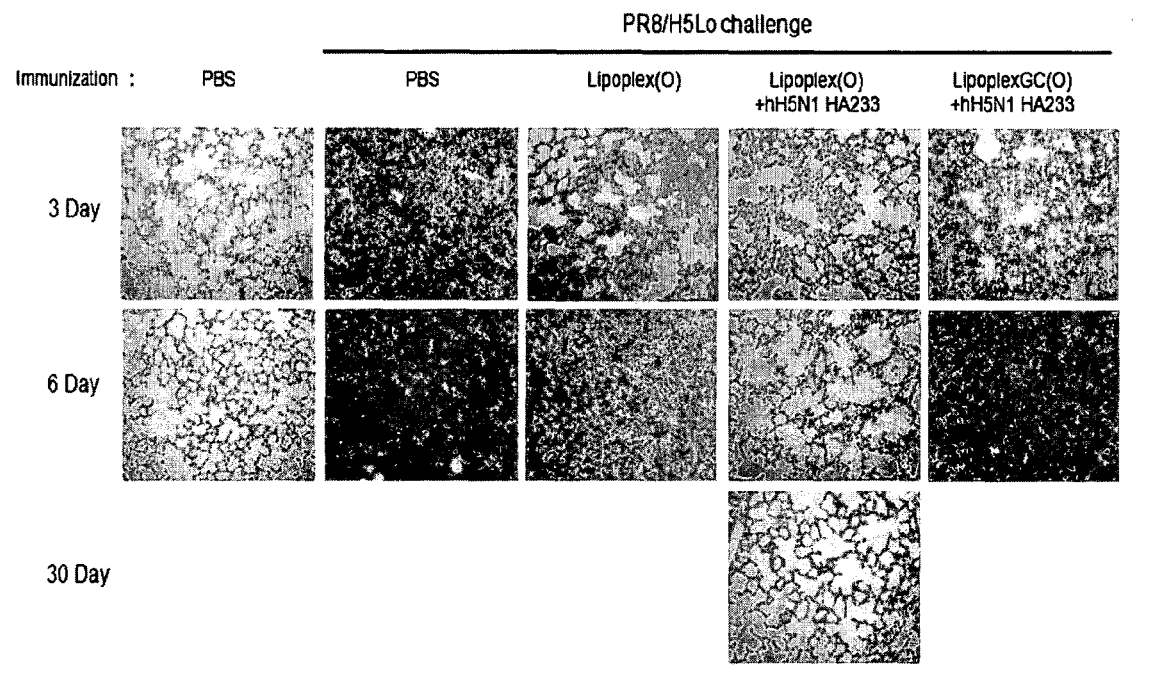

Mice were sacrificed by inhaled diethyl ether anesthesia at the indicated time points and entire lung tissue was removed. For histopathologic examination, lungs were fixed in a 4% buffered formalin solution, and embedded in paraffin by the conventional method, and cut into 4 μm thick sections. The specimens were stained with hematoxylin and eosin. In the mice inoculated with PO-DNA-peptide (hH5N1 HA233 or hH5N1 HA370)-liposome (DOPE:CHEMS) twice and then infected intranasally with the 10LD50 rH5N1 virus or the 10LD50 maA/WSN/1933 virus, the lung tissue was recovered to normal condition (FIG. 9c, 10c, 11c).

Figures 14A, 14B:
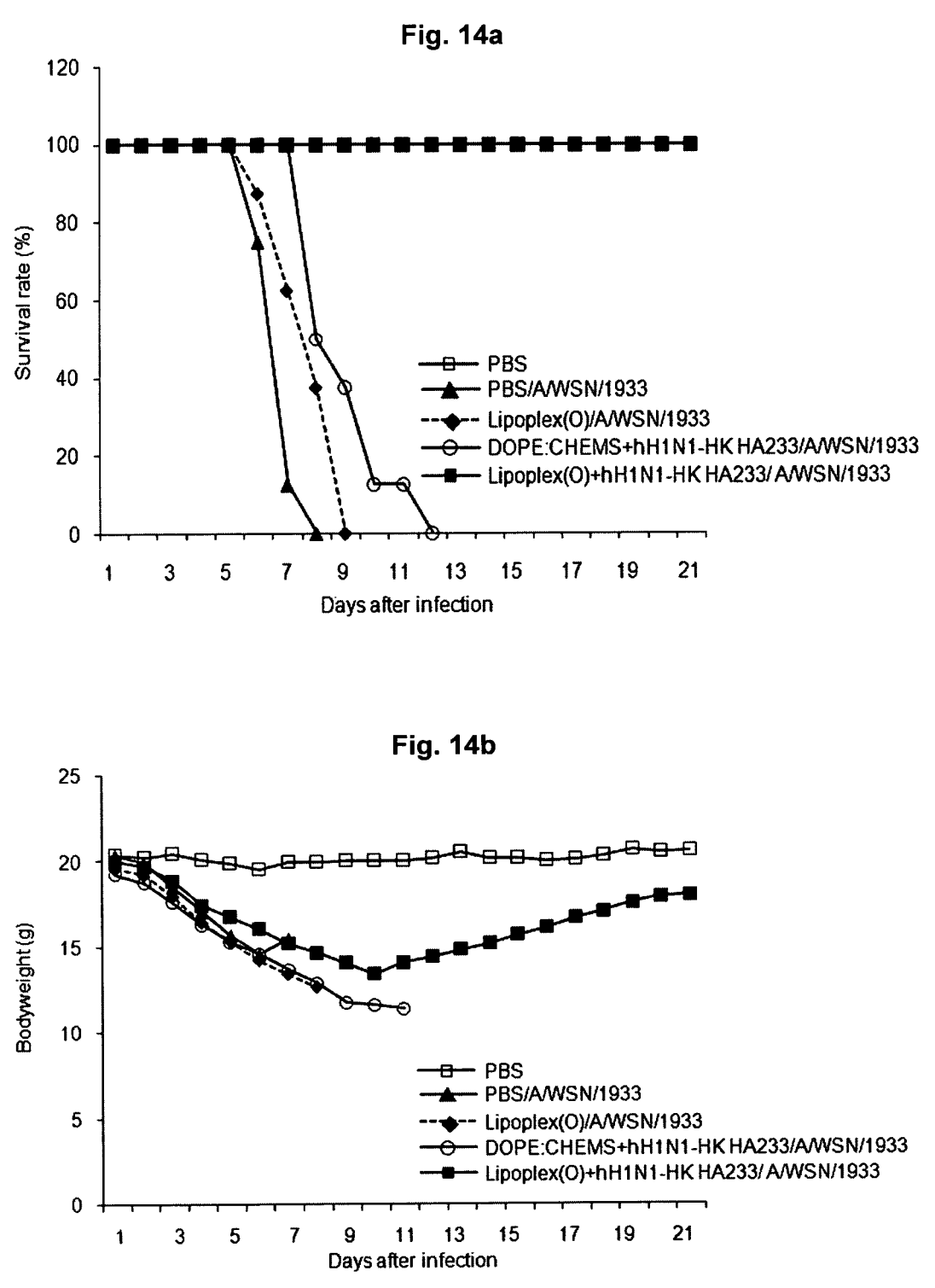
Figure 14C:
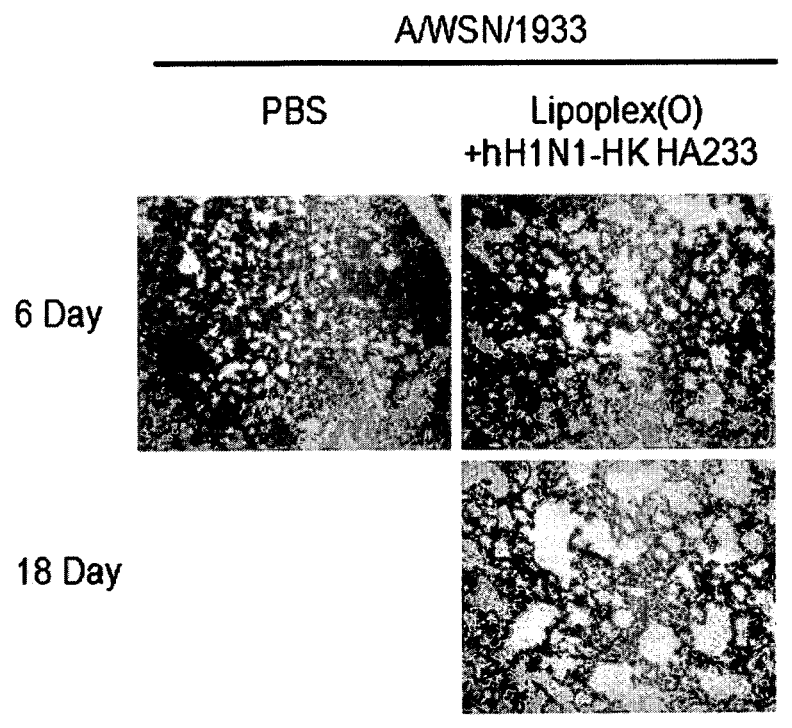

Furthermore, in the mice inoculated with PO-DNA-peptide (hH5N1-WSN HA233 or hH5N1-HK HA233)-liposome complex twice at 10 day intervals and then infected intranasally with the 10LD50 rH5N1 virus or the 10LD50 maA/WSN/1933 virus, the lung tissue was recovered to normal condition (FIGS. 13c and 14c).

<8-4> Measurement of the Titer of Virus in Mice Tissues 3 day and 6 day after intranasal infection of the 10LD50 rH5N1 virus or the 10LD50 maA/WSN/1933, lungs were isolated and homogenized in 1 ml PBS to analyze the titer of the virus. Tenfold serially diluted suspension of virus stocks or lung tissue homogenates were added onto a confluent monolayer of MDCK cells in six-well plates and incubated at room temperature for 1 h for adsorption with shaking every 10 min. The suspension was removed and the cells were covered with MEM containing 2% oxoid agar, 5% $NaHCO_3$, 1% DEAE Dextran, and (L-tosylamido-2-phenyl)ethyl chloromethyl ketone (TPCK, 1 μg/ml)-treated trypsin. After incubation at 37° C. for 3 days, the dishes were stained with 1 ml of crystal violet for 15 min so that we could visualize the plaques. The numbers of plaques were counted to determine the titers. The virus titer of lung tissue was reduced in the mice inoculated with the PO-DNA-peptide (hH5N1 HA370)-liposome (DOPE:CHEMS) twice and then infected intranasally with the 10LD50 rH5N1 virus or the 10LD50 maA/WSN/1933 virus (FIGS. 9d and 10d).

<8-5> Hemagglutination Inhibition Assay

Figure 15A:
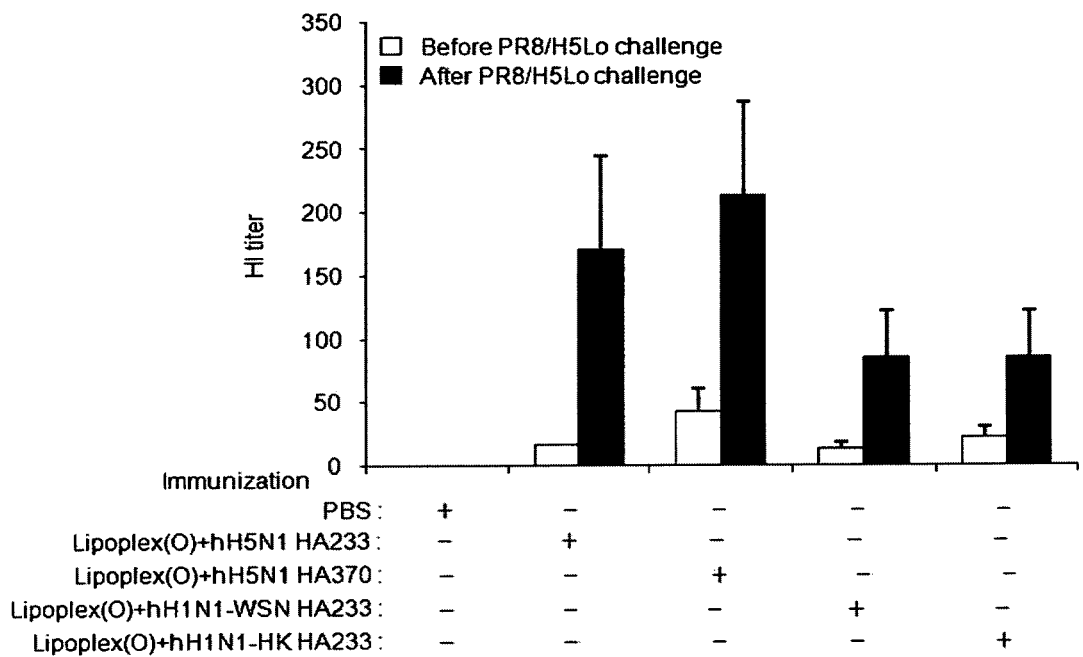
FIG. 15a-15b represent the hemagglutination-inhibition in PO-DNA (MB-ODN 4531(O))-peptide (hH5N1 HA233, hH5N1 HA370, hH1N1-WSN HA233, hH1N1-HK HA233)-DOPE:CHEMS complex-administered mice by the antisera which is generated after nasal administration of the 10LD50 rH5N1 virus (PR8/H5Lo) (FIG. 15a) and the 10LD50 maA/WSN/1993 virus (FIG. 15b).

In the mice inoculated with PO-DNA-peptide (hH5N1 HA233, hH5N1 HA370, hH1N1-WSN HA233 or hH1N1-HK HA233)-liposome (DOPE:CHEMS) twice and then infected intranasally with the 10LD50 rH5N1 virus, the inhibition of hemagglutination induced by produced antibodies was remarkably increased (FIG. 15a).

Figure 15B:
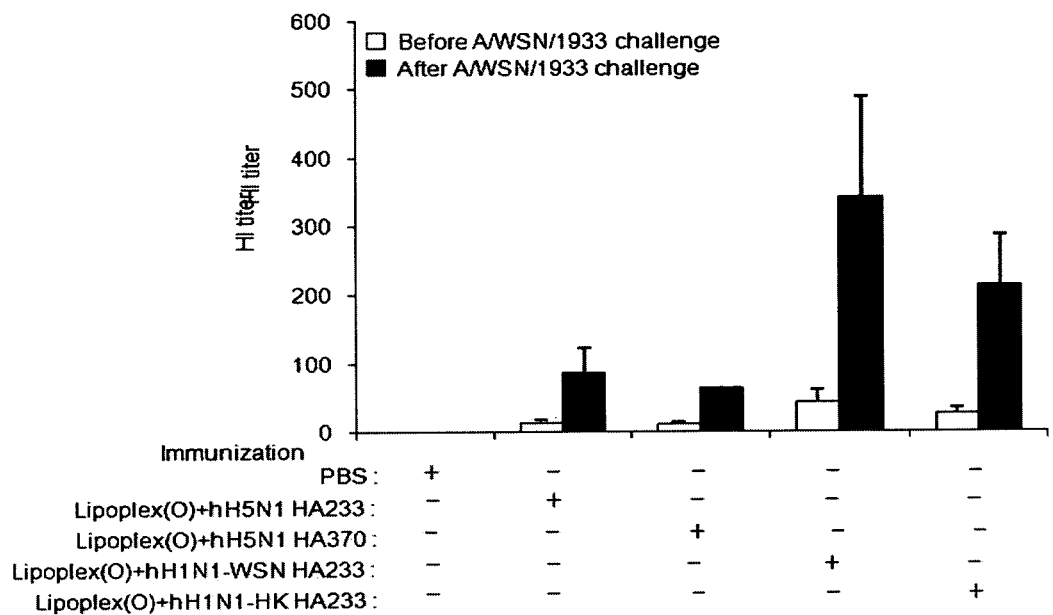

In the mice inoculated with PO-DNA-peptide (hH5N1 HA233, hH5N1 HA370, hH1N1-WSN HA233 or hH1N1-HK HA233)-liposome (DOPE:CHEMS) twice and then infected intranasally with the maA/WSN/1933 virus, the inhibition of hemagglutination induced by produced antibodies was remarkably increased (FIG. 15b).

<8-6> Measurement of Antibody

Figure 16B:
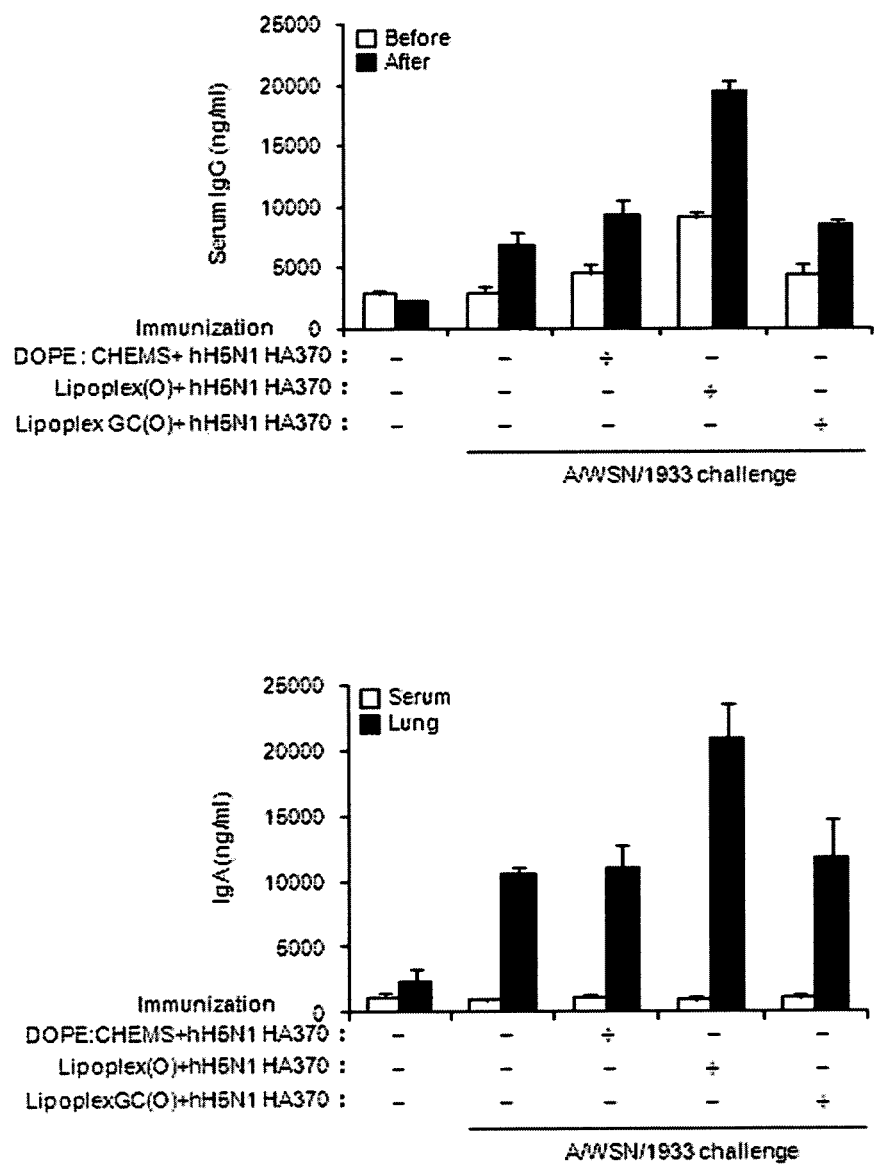
Figure 16C:
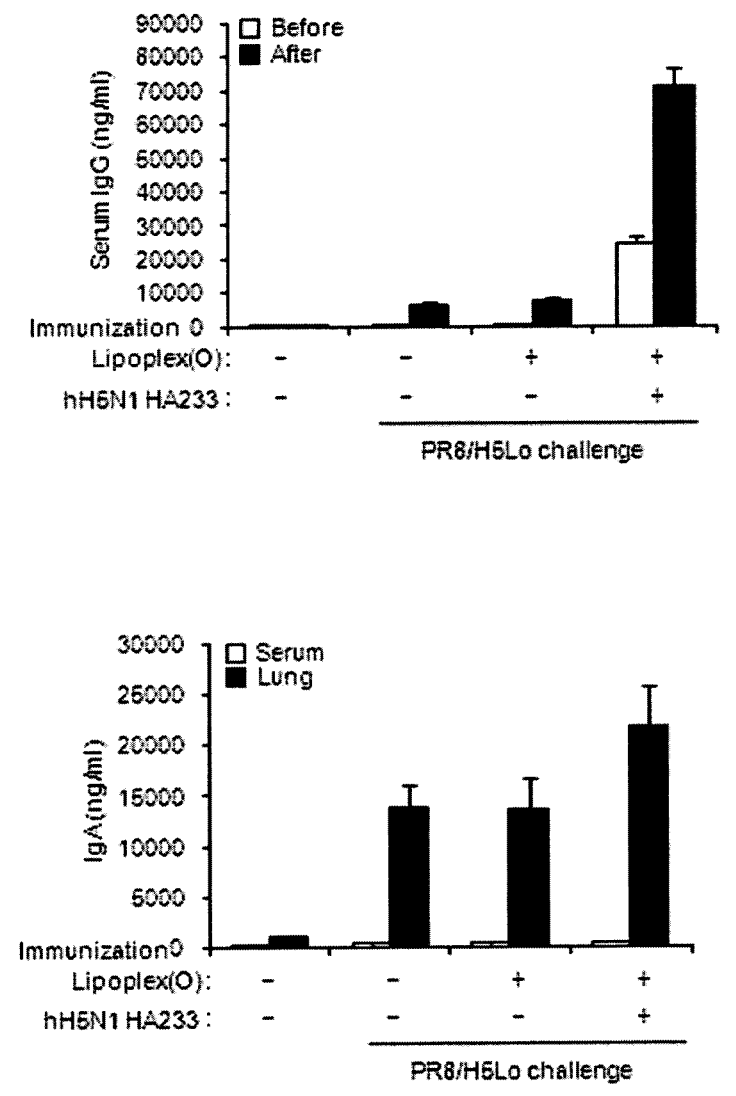
Figure 16D:
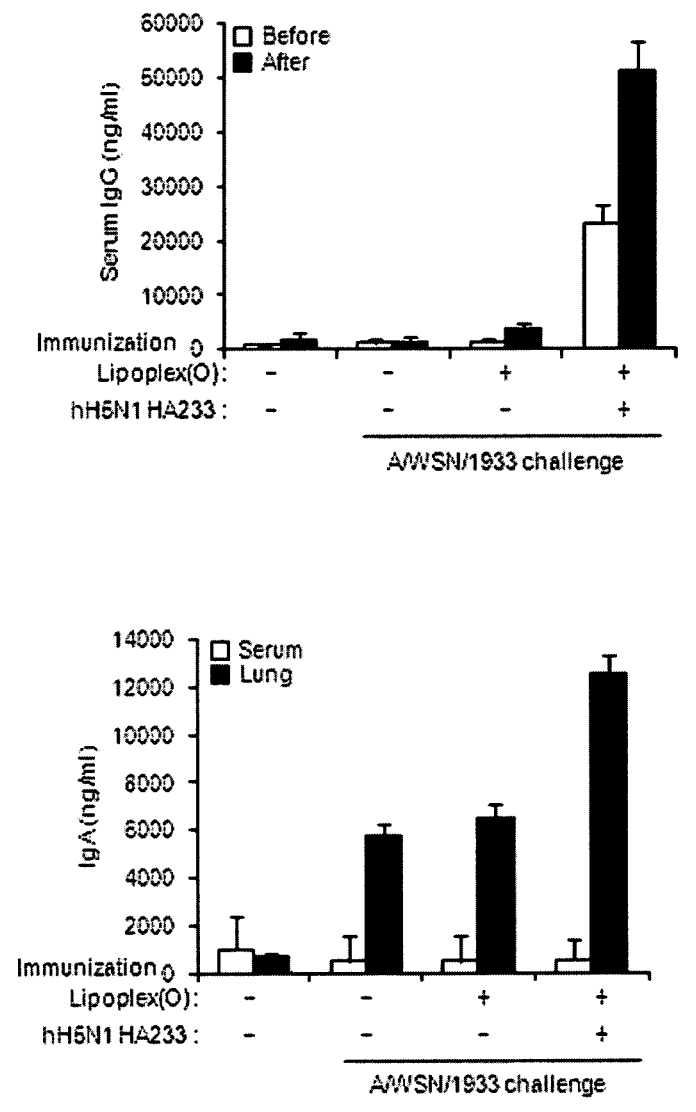
Figure 16F:
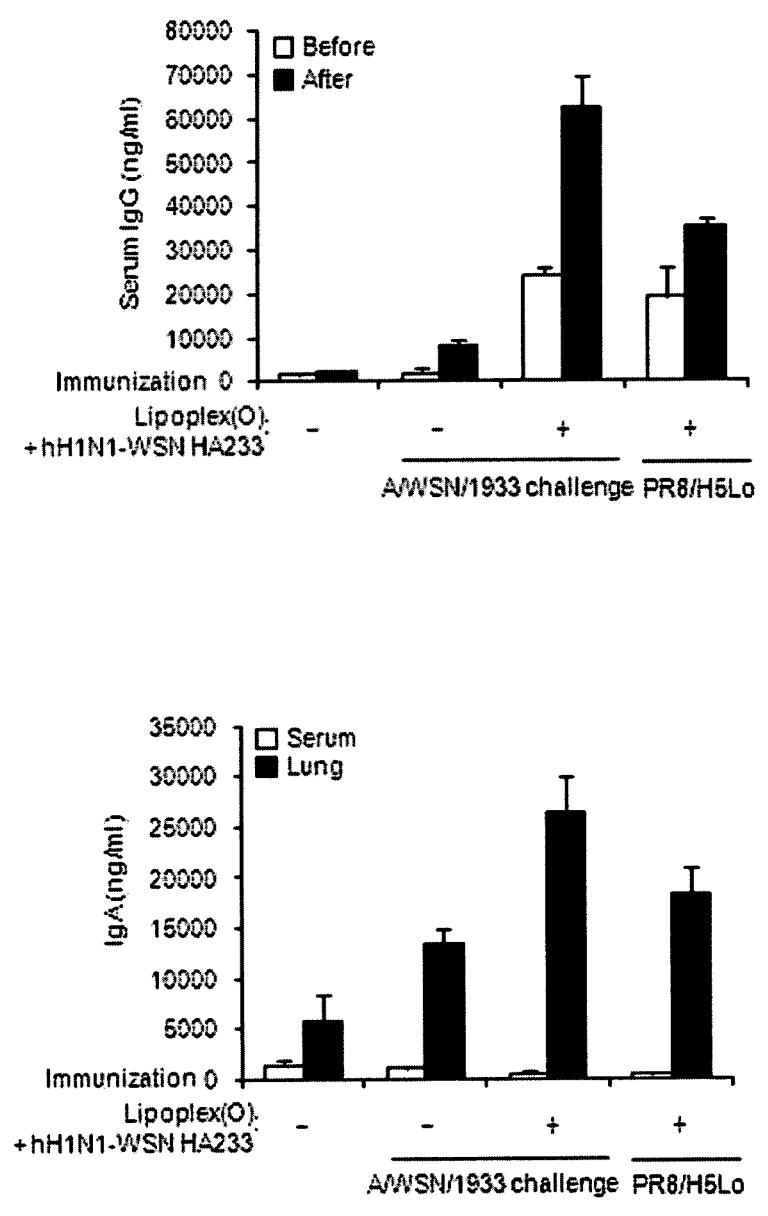

Mice were inoculated with PO-DNA-peptide (hH5N1 HA233, hH5N1 HA370, hH1N1-WSN HA233 or hH1N1-HK HA233)-liposome (DOPE:CHEMS) twice and then infected intranasally with the 10LD50 rH5N1 virus or the 10LD50 maA/WSN/1933 virus. 6 days after infection, the sera were isolated. BALF (bronchoalveolar lavage fluid) was also isolated to measure the amount of hH5N1 HA229 or hH5N1 HA371 peptide specific antibody (total IgG and IgA). When infected with 10LD50 rH5N1 virus, total IgG in sera and IgA in BALF were increased significantly (FIGS. 16a, 16c, and 16f). When infected with 10LD50 maA/WSN/1933 virus, total IgG in sera and IgA in BALF were increased significantly (FIGS. 16b, 16d, 16e and 16f).

Example 9

Memory Efficacy of Vaccination of CpG-DNA-Peptide-Liposome Complex

<9-1> Vaccination and Virus Challenge Experiments

Four-week-old BALB/c mice were injected i.p. with 50 μg of peptides supplemented with 50 μg of MB-ODN 4531(O) encapsulated in DOPE:CHEMS liposomes twice at 10 day intervals. Two months after the second immunization, the mice were inoculated intranasally challenged with the 10LD50 rH5N1 virus.

<9-2> Measurement of Weight and Survival Rate after Virus Challenge

After infection, the mice were observed daily for clinical signs and weighed. 3 days after intranasal infection of the 10LD50 rH5N1 virus, the mice began to lose their weight and died in 14 days. But the mice inoculated with PO-DNA-peptide (hH5N1 HA370)-liposome (DOPE:CHEMS) twice and then infected intranasally with the 10LD50 rH5N1 virus in two months lost their weight until 11 days but gradually recovered and survived (FIGS. 17a and 17b).

<9-3> Staining of Lung Tissue

Mice were sacrificed by inhaled diethyl ether anesthesia at the indicated time points and entire lung tissue was removed. For histopathologic examination, lungs were fixed in a 4% buffered formalin solution, and embedded in paraffin by the conventional method, and cut into 4 μm thick sections. The specimens were stained with hematoxylin and eosin. In the mice inoculated with PO-DNA-peptide (hH5N1 HA370)-liposome (DOPE:CHEMS) twice at 10 day intervals and then infected intranasally with the 10LD50 rH5N1 virus, the lung tissue was recovered to normal condition (FIG. 17c).

<9-4> Measurement of the Titer of Virus in Mice Tissues 3 of 6 days after intranasal infection of the 10LD50 rH5N1 virus, lung tissue was isolated and homogenized in 1 ml PBS to analyze the titer of the virus. The virus titer was measured by plaque assay as described in Example <8-4>. The virus titer of lung tissue was remarkably reduced in the mice inoculated with the PO-ODN-peptide (hH5N1 HA370)-liposome (DOPE:CHEMS) twice and then infected intranasally with the 10LD50 rH5N1 virus in 6 days after infection (FIG. 17d).

Example 10

Efficacy of Epitope Screening Using CpG-DNA-Peptide-Liposome Complex

<10-1> Inactivation of Recombinant Avian Influenza a Virus rH5N1 virus (PR8/H5Lo) were exposure ultraviolet (UV) wavelength (254 nm), exposure time (5 min) and distance between virion and UV light (5 cm) in order to inactivate the virus. Inactivation of viral infectivity was confirmed by plaque assay.

<10-2> Immunization 4 week-old BALB/c mice were injected i.p. with inactivated rH5N1 virus or inactivated rH5N1 virus and liposome complex or inactivated rH5N1 virus-MB-ODN4531 (50 μg/mouse)-liposome complex. The same amount of inactivated rH5N1 virus and MB-ODN4531 mixture was injected three times at 10 day intervals. After 10 days, blood was obtained by heart punching method and the sera were collected through blood cell precipitation by centrifugation. From the collected sera, the amount and the titer of anti-recombinant H5N1 virus antibodies (total IgG, IgG1, IgG2a) was analyzed by ELISA as described in Example <4-4>.

<10-3> ELISA

The mice were sacrificed 10 day after the injection. Obtained sera were diluted to 1:10 with PBS/0.2% sodium azide and then stored at −20° C. Each selected peptide (hH5N1 HA233, hH5N1 HA370) or inactivated rH5N1 virus (10 μg/ml, sodium bicarbonate buffer, pH 9.6) were added to the 96-well immunoplates (Nalgen Nunc International, Rochester, N.Y., USA) and left for 16 h at 4° C. And then the production of total IgG, IgG1 and IgG2a (FIG. 18), which specifically bind to H5N1 virus or each peptide, were analyzed as described in Example <4-4>.

It was confirmed that the amount and the titer of total IgG (FIGS. 18a and 18b) and the production of IgG2a related to Th1 immune response were increased in the sera inoculated with the inactivated rH5N1 virus.

Among the avian influenza A/H5N1/Vietnam/2004 strain HA proteins, hH5N1 HA233 and hH5N1 HA370 peptide increased the titer of each peptide-specific total IgG, while the sera immunized with inactivated rH5N1 virus did not show any titer of hH5N1 HA233 or hH5N1 HA370 peptide-specific antibody (FIGS. 18c and 18d), which indicated that hH5N1 HA233 or hH5N1 HA370 peptide-specific antibody was produced in the sera immunized with MB-ODN 4531 (O)-each peptide-liposome (DOPE:CHEMS) complex.

Example 11

Screening of HCV Epitope Using CpG-DNA-Peptide-Liposome Complex

<11-1> Immunization of CpG-DNA-HCV Peptide-Liposome Complex

Among HCV E1 and E2 proteins, three epitopes (Table 10) were selected considering hydrophilicity, hydrophobicity, secondary structure, antigenicity and amphiphilicity for preparing CpG-DNA-HCV peptide-liposome complex as described in Example 3. Prepared CpG-DNA-HCV peptide-liposome complex (50 μg/mouse) was injected i.p. to BALB/c mice on three occasions at 10 day intervals as described in Example <4-3>. After 10 days, blood was obtained by heart punching method and the sera were collected through blood cell precipitation by centrifugation. From the collected sera, the titer of anti-peptide antibodies (total IgG, IgG1, IgG2a) was analyzed by ELISA.

<11-2> ELISA

The mice were sacrificed 10 day after the injection. Obtained sera were diluted to 1:10 with PBS/0.2% sodium azide and then stored at −20° C. Each selected peptide (10 μg/ml, sodium bicarbonate buffer, pH 9.6) were added to the 96-well immunoplates (Nalgen Nunc International, Rochester, N.Y., USA) and left for 16 h at 4° C. And then the production of total IgG (FIG. 19a), IgG1 and IgG2a (FIGS. 19b and 19c), which specifically bind to each peptide, were analyzed as described in Example <4-4>.

It was confirmed that the titer of total IgG (FIG. 19c) and the production of IgG2a related to Th1 immune response were increased in the sera immunized with the HCV-E2 202 peptide selected from the HCV E2 protein.

<11-3> Effect of Types of Liposomes on CpG-DNA-Peptide-Liposome-Induced Humoral Immune Response MB-ODN 4531-peptide (HCV-E1 202) were complexed with various types of liposomes (DOPE:CHEMS (1:1), DSPC:Chol (1:1), DSPC:CHEMS:PEG-PE (1:1:1), Chol: DOPE:PEG-PE (1:1:1), Dc-Chol:DOPE:PEG-PE (1:1:1)) as described in Example 3 and i.p. injected to BALB/c mice three times as described in Example <4-4>. As results of measuring the titer of HCV-E2 202 peptide specific total IgG, the titer was highest at the molar ratio of DOPE:CHEMS (1:1) (FIG. 19d)

Example 12

Screening of hRSV Epitope Using CpG-DNA-Peptide-Liposome Complex

<12-1> Immunization of CpG-DNA-hRSV Peptide-Liposome Complex

Among hRSV G and F proteins, twenty epitopes (Table 10, 11 and 12) were selected considering hydrophilicity, hydrophobicity, secondary structure, antigenicity and amphiphilicity for preparing CpG-DNA-each hRSV peptide-liposome (DOPE:CHEMS) complex as described in Example 3. Prepared CpG-DNA-each hRSV peptide-liposome complex (50 μg/mouse) was injected i.p. to BALB/c mice on three or four occasions at 10 day intervals as described in Example <4-3>. After 10 days, blood was obtained by heart punching method and the sera were collected through blood cell precipitation by centrifugation. From the collected sera, the titer of anti-peptide antibodies (total IgG, IgG1, IgG2a) was analyzed by ELISA.

<12-2> ELISA

The mice were sacrificed 10 day after the injection. Obtained sera were diluted to 1:10 with PBS/0.2% sodium azide and then stored at −20° C. Each selected peptides (10 μg/ml, sodium bicarbonate buffer, pH 9.6) were added to the 96-well immunoplates (Nalgen Nunc International, Rochester, N.Y., USA) and left for 16 h at 4° C. And then the production of total IgG (FIGS. 20a and 21), IgG1 and IgG2a (FIGS. 21b and 21c), which specifically bind to each peptide, were analyzed as described in Example <4-4>.

It was confirmed that the amount of total IgG (FIGS. 20a, 21a and 21d) and the production of IgG2a (FIGS. 20b, 20c, 21b, 21c and 21d) related to Th1 immune response were increased in the sera immunized with the HRSV-G1, HRSV-Fa3, HRSV-Fa3-2, HRSV-F7 and HRSV-F9 peptide selected from the hRSV G and F proteins.

Example 13

Screening of Human Integrin β4 Epitope Using CpG-DNA-Peptide-Liposome Complex

<13-1> Immunization of CpG-DNA-hIB4 Peptide-Liposome Complex

Among human integrin β4 protein (hIB4) that is expressed in most carcinoma cells, six epitopes (Table 13) were selected considering hydrophilicity, hydrophobicity, secondary structure, antigenicity and amphiphilicity for preparing CpG-DNA-each hIB4 peptide-liposome (DOPE:CHEMS) complex as described in Example 3. Prepared CpG-DNA-each hIB4 peptide-liposome complex (50 μg/mouse) was injected i.p. to BALB/c mice on three or four occasions at 10 day intervals as described in Example <4-3>. After 10 days, blood was obtained by heart punching method and the sera were collected through blood cell precipitation by centrifugation. From the collected sera, the titer of anti-peptide antibodies (total IgG) was analyzed by ELISA.

<13-2> ELISA

The mice were sacrificed 10 day after the injection. Obtained sera were diluted to 1:10 with PBS/0.2% sodium azide and then stored at −20° C. Each selected peptides (10 μg/ml, sodium bicarbonate buffer, pH 9.6) were added to the 96-well immunoplates (Nalgen Nunc International, Rochester, N.Y., USA) and left for 16 h at 4° C. And then the amount of total IgG (FIG. 22a) and titer of total IgG (FIG. 22b) were analyzed as described in Example <4-4>.

It was confirmed that the amount of total IgG (FIG. 22a) and titer of total IgG (FIG. 22b) were increased in the sera immunized with the hIB4-VWA-1-2, hIB4-VWA-1-3, hIB4-VWA-2, hIB4-VWA-3 and hIB4-EGF-1 peptide selected from the hIB4 protein.

Example 14

Screening of Hepatocarcinoma-Specific TM4SF5 protein Epitope Using CpG-DNA-Peptide-Liposome Complex <14-1> Immunization of CpG-DNA-TM4SF5 Peptide-Liposome Complex Among TM4SF5 proteins, sixe epitopes (Table 10) were selected considering hydrophilicity, hydrophobicity, secondary structure, antigenicity and amphiphilicity for preparing CpG-DNA-TM4SF5 peptide-liposome (DOPE:CHEMS) complex as described in Example 3. Prepared CpG-DNA-each TM4SF5 peptide-liposome complex (50 μg/mouse) was injected i.p. to BALB/c mice on three occasions at 10 day intervals as described in Example <4-3>. After 10 days, blood was obtained by heart punching method and the sera were collected through blood cell precipitation by centrifugation. From the collected sera, the titer of anti-each peptide antibodies (total IgG, IgG1, IgG2a) was analyzed by ELISA.

<14-2> ELISA

The mice were sacrificed 10 day after the injection. Obtained sera were diluted to 1:10 with PBS/0.2% sodium azide and then stored at −20° C. Each selected peptides (10 μg/ml, sodium bicarbonate buffer, pH 9.6) were added to the 96-well immunoplates (Nalgen Nunc International, Rochester, N.Y., USA) and left for 16 h at 4° C. And then the production of total IgG (FIG. 23a), IgG1 and IgG2a (FIG.

23b), which specifically bind to each peptide, were analyzed as described in Example <4-4>.

It was confirmed that the titer of total IgG (FIG. 23a) and the production of IgG2a (FIG. 23b) related to Th1 immune response were increased in the sera inoculated with the TM4SF5 R2-3 or TM4SF5 R2-5 peptide selected from the TM4SF5 protein.

<14-3> Effect of Types of Liposomes on CpG-DNA-Peptide-Liposome-Induced Humoral Immune Response MB-ODN 4531-peptide (TM4SF5 R2-3) were complexed with various types of liposomes (DOPE:CHEMS (1:1), DSPC:Chol (1:1), DSPC:CHEMS:PEG-PE (1:1:1), Chol:DOPE:PEG-PE (1:1:1), Dc-Chol:DOPE:PEG-PE (1:1)) as described in Example 3 and i.p. injected to BALB/c mice three times as described in Example <4-4>. As results of measuring the titer of TM4SF5 R2-3 peptide specific total IgG, the titer was highest at the molar ratio of DOPE:CHEMS (1:1) (FIG. 23c).

<14-4> Effect of Types of CpG-DNA on CpG-DNA-Peptide-Liposome-Induced Humoral Immune Response TM4SF5 R2-3 peptide-liposome DOPE:CHEMS (1:1) were complexed with various types of PO-DNA (MB-ODN4531(O), MB-ODN 4531(GCO) or PS-DNA (MB-ODN 4531(S)) represented in Table 1 as described in Example 3 and i.p. injected to BALB/c mice three times as described in Example <4-4>. As results of measuring the titer of TM4SF5 R2-3 peptide-specific total IgG, the titer was highest when PO-DNA (MB-ODN 4531(O)) or PS-DNA (MB-ODN 4531(S) was used (FIG. 23d).

<14-5> Effect of TLR9 on CpG-DNA-Peptide-Liposome-Induced Humoral Immune Response To investigate the role of TLR9 in antibody production from hTM4SF5R2-3 peptide and MB-ODN 4531(O) coencapsulated in DOPE:CHEMS complex-injected mice, we assessed IgG production with BALB/c TLR9 knockout mice and wild type mice. As expected, IgG-producing ability of hTM4SF5R2-3 peptide and MB-ODN 4531(O) coencapsulated in DOPE:CHEMS complex was absolutely dependent on TLR9 because TLR9 knockout mice did not produce IgG when injected with hTM4SF5R2-3 peptide and MB-ODN 4531(O) coencapsulated in DOPE:CHEMS complex (FIG. 23e). In contrast, injection of mice with HEL in combination with IFA was found to increase IgG production from wild type mice and TLR9 knockout mice (FIG. 23f).

Figure 24C:
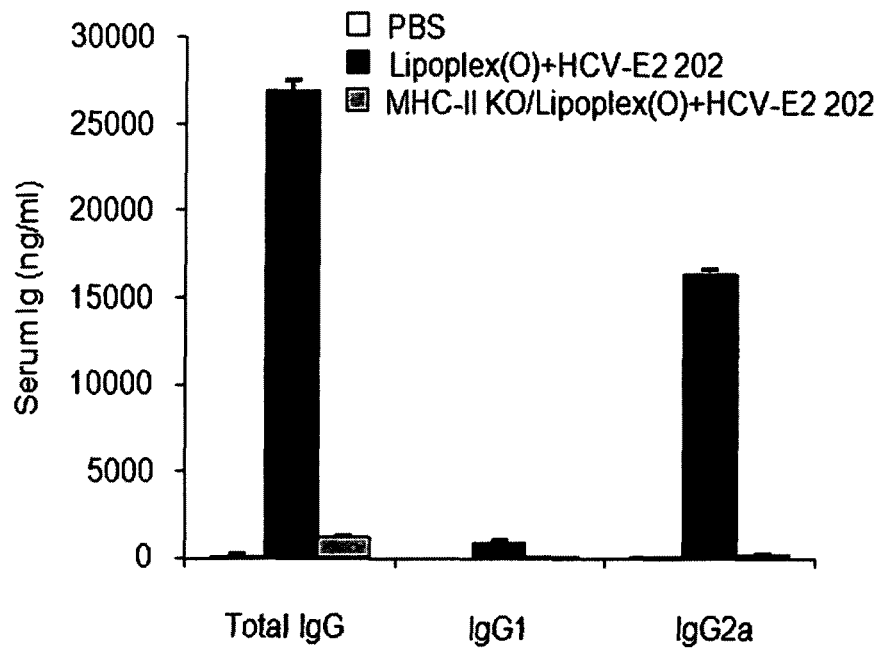
Figure 24D:
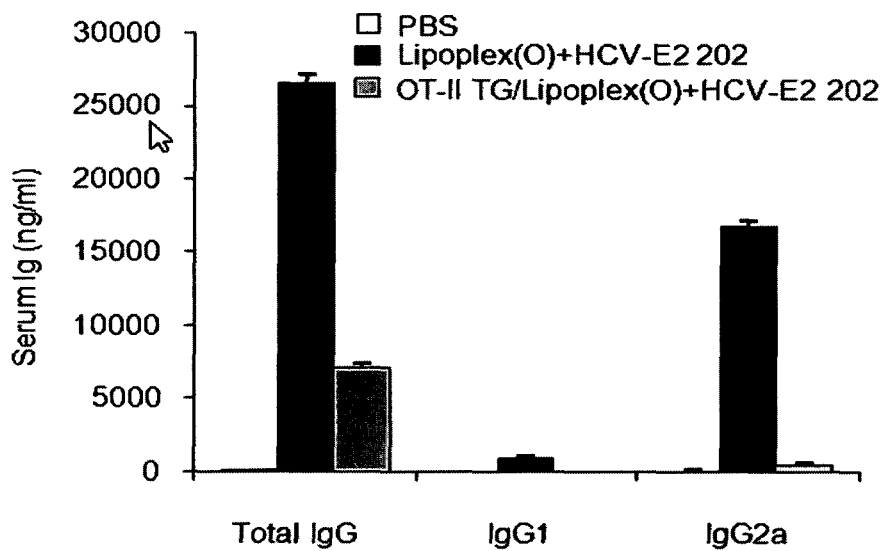
Figure 24E:
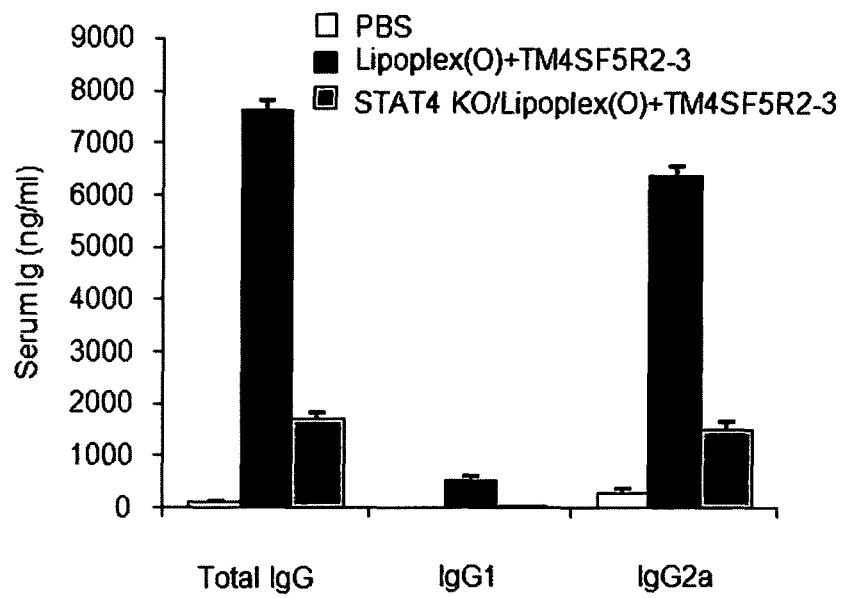
Figure 24F:
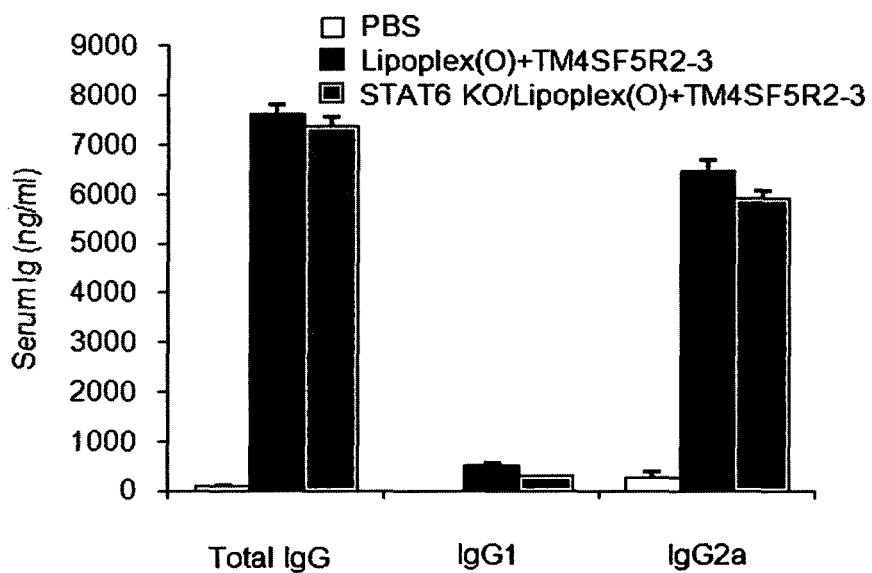

<14-5> Effect of MHC class II-Mediated Presentation and Th1 Differentiation on CpG-DNA-Peptide-Liposome-Induced Humoral Immune Response To evaluate the kinetics of IgG production in response to epitope and MB-ODN 4531(O) coencapsulated DOPE:CHEMS complex immunization, we injected BALB/c mice i.p. with hTM4SF5R2-3 peptide and MB-ODN 4531(O) coencapsulated in DOPE:CHEMS complex three times with a 10 day interval. The BALB/c mice produced larger amounts of the peptide-specific IgG (IgG2a) in the secondary and tertiary responses (FIG. 24a). Next, we investigated the requirement of MHC class II-mediated presentation for IgG production in response to hTM4SF5R2-3 peptide and MB-ODN 4531(O) coencapsulated in DOPE:HEMS complex. As shown in FIG. 24b, depletion of CD4$^+$ cells by injection BALB/c mice i.p. with anti-CD4 antibody dramatically reduced the peptide-specific IgG production. Further, we also observed the reduction of IgG and IgG2a production in MHC class II knockout mice and OT-II transgenic mice in response to hTM4SF5R2-3 peptide and MB-ODN 4531(O) coencapsulated in DOPE:CHEMS complex immunization (FIG. 24c, 24d). We also examined the involvement of Th1 differentiation for IgG production in response to hTM4SF5R2-3 peptide and MB-ODN 4531(O) coencapsulated in DOPE:CHEMS complex immunization. The reduction of IgG and IgG2a production was detected in the STAT4 knockout mice, STAT4 promotes the differentiation of the T cells into Th1 cells, in response to hTM4SF5R2-3 peptide and MB-ODN 4531(O) coencapsulated in DOPE:CHEMS complex immunization (FIG. 24e). However, the effect of STAT6 knockout on hTM4SF5R2-3 peptide and MB-ODN 4531(O) coencapsulated in DOPE:CHEMS complex-induced IgG production was not observed as shown in FIG. 24f). These results suggest that production of IgG (IgG2a) requires in CD4$^+$ cells, MHC class II-mediated presentation and Th1 differentiation from B cell epitope and MB-ODN 4531(O) coencapsulated in DOPE:CHEMS complex immunization.

Example 15

Production of Mouse Anti-hTM4SF5 Monoclonal Antibody

After BALB/c mice injected i.p. with hTM4SF5R2-3 peptide (50 µg) and MB-ODN 4531(O) (50 µg) coencapsulated in DOPE:CHEMS complex on three occasions at 10 day intervals, the hybridoma cells producing anti-hTM4SF5R2-3 peptide-specific mAbs were screened according to the standard hybridoma technique. (39). The anti-hTM4SF5R2-3 peptide mAb (IgG2a) was purified from ascites fluid by a Protein A column chromatography (Amersham Pharmacia Biotech, Piscataway, N.J., USA).

Example 16

Recognition of TM4SF5 Protein by Monoclonal Antibody produced by CpG-DNA-TM4SF5 peptide-liposome complex <16-1> Analysis of TM4SF5 Expression in Human Hepatoma Cells Human hepatocarcinoma cell lines (Huh-7) were purchased from American Type Culture Collection (ATCC, Manassas, Va., USA). Human hepatic cell lines (SNU-398, SNU-423, SNU-739 and SNU-761) were purchased from Korean Cell Line Bank (Seoul, Korea). The Huh-7, SNU-398, SNU-423, SNU-739 and SNU-761 cells were cultured in RPMI 1640 media containing 10% FBS (fetal bovine serum; Hyclone, Logan, Utah, USA). Human normal hepatic cells (Promo Cell, Heidelberg, Germany) were cultured according to the manufacturer's specifications. All cells were incubated at 37° C. under 5% $CO_2$ and 95% air condition. To investigate hTM4SF5 mRNA expression, RT-PCR was performed. Total RNA was isolated using RNeasy Mini Kit (Qiagen, Germantown, Md., USA) and preparation of cDNA was carried out by the process previously described (40). Standard 25 PCR cycles were performed using the following primer sets: human β-actin, 5'-GGGTCAGAAGGATTCCTATG-3' and 5'-CCTTAATGTCACGCACGATTT-3' (500 bp); hTM4SF5. Huh-7 and SNU-761 cells showed high level of TM4SF5 mRNA expression (FIG. 25a).

<16-2> Recognition of TM4SF5 Protein by Monoclonal Antibody Recognizing TM4SF5 R2-3 Peptides (FACS Analysis)

To investigate the binding of antibody, hepatocarcinoma cells were washed in PBS containing 0.1% BSA and incubated for 20 min at 4° C. with 10 µg/ml of human IgG (sigma) for blocking of Fc receptor-binding. After blocking, cells were cultured with purified anti-TM4SF5 R2-3 peptide antibody (Example 15) for 1 h. And then, the cells were washed in PBS containing 0.1% BSA and cultured with FITC-conjugated goat anti-mouse IgG antibody (BD Biosciences) for 30 min at 4° C. It was confirmed that purified anti-TM4SF5 R2-3 peptide antibody bound to Huh-7 and SNU-761 cells which were proved to express TM4SF5 mRNA (FIG. 25c).

Example 17

Inhibition of Hepatocarcinoma Cell Growth by Antibody Produced by CpG-DNA-TM4SF5 Peptide-Liposome Complex <17-1> Cell Growth Inhibition by Anti-TM4SF5 R2-3 Peptide Monoclonal Antibody Growth of human hepatocarcinoma cells (Huh-7 and SNU-739) were analyzed by MTT assay after 72 h treatment of anti-TM4SF5 R2-3 peptide antibody (10 µg/ml).

The hepatocarcinoma cells were incubated in 48-well plate for 72 h, 3-(4,5-dimethylthiazole-2-yl)-2,5-diphenyl tetrazolium bromide (MTT, Sigma-Aldrich) solution was added to each plate and incubated for more 4 h at 37° C. After the media was removed, formazan crystals were solubilized in DMSO. The color development was monitored at 570 nm with a reference wavelength of 650 nm using a spectrophotometer (SpectraMax250, Molecular Devices, Downingtown, Pa., USA). It was verified by MTT assay that the growth of Huh-7 cells expressing TM4SF5 was inhibited when they were treated with the anti-TM4SF5 R2-3 peptide antibody (FIG. 25d). In contrast, the cells not expressing TM4SF5 (SNU-739) were not affected (FIG. 25d).

<17-2> Regulation of Cell Cycles by Anti-TM4SF5 R2-3 Peptide Antibody

Hepatocarcinoma cells (Huh-7 and SNU-739) were treated with the anti-TM4SF5 R2-3 peptide antibody (10 µg/ml) for 72 h and the cell cycles were observed. DNA contents were measured through incubating in PI (propidium iodide) (20 µg/ml) dissolved in RNase (200 µg/ml)-containing PBS. The cells were stained at room temperature for 30 min and analyzed by FACScan flow cytometer (BD biosciences). Data were analyzed by ModFit LT 3.0 software for cell cycle distribution.

The distribution of cell cycle stages in each population was compared. It was observed that the S phage of Huh-7 cell expressing TM4SF5 was arrested when they were treated with the anti-TM4SF5 R2-3 peptide antibody. In contrast, the cell cycle of SNU-739 which did not express TM4SF5 was not affected (FIG. 25d).

<17-3> Inhibition of Hepatocarcinoma Cells by Anti-TM4SF5 R2-3 Peptide Antibody

It had been discovered that TM4SF5 expressing hepatocarcinoma cells lost cell-cell contact inhibition capacity to develop to be hepatocarcinoma cells (41). While TM4SF5 expressing hepatocarcinoma cells show abnormal actin bundling, in cells not expressing TM4SF5 the distinct outline of stress fiber supporting an overspread polygonal shape is detected by actin staining (41). Therefore, we treated the anti-TM4SF5 R2-3 peptide antibody (10 µg/ml) to the hepatocarcinoma cells (Huh-7 and SNU-739) for 72 h and observed the actin.

The cells were cultured on glass coverslips in 12-well plates 1 day before the anti-hTM4SF5 antibody (10 µg/ml) treatment. After cells were treated the antibody for 72 h, the cells were fixed with 4% paraformaldehyde, permeabilized with 0.1% Triton X-100, and stained with phalloidin-conjugated with rhodamine (Molecular Probes, Eugene, Oreg., USA). Nuclei were stained with Hoechst No. 33258. The mounted samples were scanned with an LSM 510 META NLO (Carl Zeiss, Jena, Germany).

When the hepatoma cells expressing TM4SF5 (Huh-7) were treated with the hTM4SF5 R2-3 peptide-specific antibody, the actin had a distinct outline of stress fiber supporting an overspread polygonal shape as in the cell which does not express TM4SF5, which indicates that the antibody is targeted to the hTM4SF5 expressing cells (FIG. 25f). These results suggest that the antibody generated by MB-ODN4531 (O) and hTM4SF5 R2-3 coencapsulated liposome (DOPE: CHEMS) may be effectively used to detect hTM4SF5 proteins, and that antibody-mediated hTM4SF5 targeting is related to functional change of hepatoma cells, which enables the cell growth to be reduced to change the diversity of cell functions.

Example 18

Inhibition of Hepatocarcinoma Cell Growth In Vivo by hTM4SF5R2-3 Peptide-Specific Antibody <18-1> Xenograft Experiment in Nude Mice $5 \times 10^6$ Hepatocarcinoma cells (Huh-7) were subcutaneously injected in the right flank of nude mice. After the cancer grew to 5 mm in diameter, the samples were divided to three groups of PBS, normal IgG and anti-TM4SF5 R2-3 peptide antibody group (n=5/group). Each group was injected with PBS and each antibody (100 mg/Kg mouse) on five occasions at 3 day intervals. Total volume of the cancer was measured using a calipers during five week observation. Analysis of xenograft experiments revealed that anti-TM4SF5R2-3 peptide antibody targeting of hepatocarcinoma cells is sufficient to decrease tumor growth in vivo (FIGS. 26a and 26b).

Example 19

Inhibition of Hepatocarcinoma Cell Growth In Vivo by Vaccination with MB-ODN 4531(O)-hTM4SF5R2-3 Peptide-Liposome Complex <19-1> Mouse Tumor Allograft Experiment Four-week-old BALB/c mice were injected i.p. with MB-ODN 4531(O)-TM4SF5R2-3 peptide-liposome (DOPE: CHEMS) complex three times at 10 day intervals. 10 days after the third immunization, 5×106 BNL-HCC cells containing 50% Matrigel were subcutaneously injected in the right flank of the BALB/c mice. Total volume of the tumor was measured using a calipers during seven week observation. Mice immunized with MB-ODN 4531(O)-TM4SF5R2-3 peptide-liposome (DOPE:CHEMS) complex had a significant reduction in tumor volume as compared with untreated mice (FIGS. 27a and 27b).

Having described a preferred embodiment of the present invention, it is to be understood that variants and modifications thereof falling within the spirit of the invention may become apparent to those skilled in this art, and the scope of this invention is to be determined by appended claims and their equivalents.

References
1. Ben-Yedidia, T., et al., *Curr. Opin. Siotechnol.* 8: 442-448 (1997).
2. Bijker, M. S., et al., *Expert Rev. Vaccines* 6: 591-603 (2007).
3. Ben-Yedidia, T., et al., *Expert Rev. Vaccines* 6: 939-948 (2007).
4. Castilow, E. M., et al., *Immunol. Res.* 39: 225-239 (2007).
5. Rosenberg, S. A., et al., *Nat. Med.* 10: 909-915 (2004).

6. Zhao, L., et al., *Expert Rev. Vaccines* 7: 1547-1555 (2008).
7. Kashala, O., et al., *Vaccine* 20: 2263-2277 (2002).
8. Engler, O., et al., *Mol. Immunol.* 38: 457-465 (2001).
9. Pinto, L. A, et al., *AIDS* 13: 2003-2012 (1999).
10. Chikh, G., et al., *Bioscience Reports* 22: 339-353 (2002).
11. Ben-Yedidia, T., et al., *Int. Immunol.* 11: 1043-1051 (1999).
12. Speiser, D. E., et al., *J. Clin. Invest.* 115: 739-746 (2005).
13. Felnerova, D., et al., *Curr. Opin. Biotechnol.* 15: 518-529 (2004).
14. Simoes, S., et al., *Adv. Drug Deliv. Rev.* 56: 947-965 (2004).
15. Collins, D. S., et al., *J. Immunol.* 148: 3336-3341 (1992).
16. Chang, J., et al., *Vaccine* 19: 3608-3614 (2001).
17. Krieg, A. M. *Annu. Rev. Immunol.* 20: 709-760 (2002).
18. Klinman, D. M., et al., *Immunological Reviews* 199: 201-216 (2004).
19. Chu, R. S., et al., *J. Exp. Med.* 186: 1623-1631 (1997).
20. Carson, D. A., et al., *J. Exp. Med.* 186: 1621-1622 (1997).
21. Davis, H. L., et al., *J. Immunol.* 160: 870-876 (1998).
22. Suzuki, Y., et al., *Cancer Res.* 64: 8754-9760 (2004).
23. Gursel, I et al., *J. Immunol.* 167: 3324-3328 (2001).
24. Li, W. M., et al., *Vaccine* 21: 3319-3329 (2003).
25. Krieg, A. M. *Nat. Rev. Drug. Discov.* 5: 471-484 (2006).
26. Sparwasser, T., et al., *J. Immunol.* 162: 2368-2374 (1999).
27. Deng, G. M., et al., *Nat. Med.* 5: 702-705 (1999).
28. Ronaghy, A., et al., *J. Immunol.* 168: 51-56 (2002).
29. Yasuda, K., et al., *J. Immunol.* 174: 6129-6136 (2005).
30. Magnusson, M., et al., *J. Immunol.* 179: 31-35 (2007).
31. Lee, K. W., et al., *Mol. Immunol.* 43: 2107-2118 (2006).
32. Kim, D., et al., *Biochem. Biophys. Res. Commun.* 379: 362-367 (2009).
33. McConnell, H. M., et al., *Science* 257:1906-1912 (1992).
34. Sjolander, S., et al., *Anal. Chem.* 63:2338-2345 (1991).
35. Szabo, A., et al., *Curr. Opin. Struct. Biol.* 5:699-705 (1995).
36. Hoffmann, E., et al., *Vaccine* 20: 3165-3170 (2002).
37. Palmer, D. F., et al., *Immunol. Ser.* 6: 51-52 (1975).
38. Kida, H., et al., *Virology* 122: 38-47 (1982).
39. Yokoyama, W. M. Production of monoclonal antibody, p. 2.5.1-2.5.17. In J. E. Ciligan, A. M. Kruisbeek, D. H. Margulies, E. M. Shevach, & W. Strober (eds.), Current protocols in Immunology, John Wiley & Sons. Inc., Newcastle, United Kingdom. (2001).
40. Kim, D., et al., *Immunol. Invest.* 38: 132-152 (2009).
41. Lee, S. A., et al., *J. Clin. Invest.* 118: 1354-1365 (2008))

What is claimed is:

1. A composition for enhancing an immune response comprising as active ingredients (a) an immunostimulatory oligonucleotide and (b) a synthetic peptide epitope having a sequence consisting of SEQ ID NO:10 and being encapsulated in a liposome containing an anionic surfactant and a neutral phospholipid.

2. The composition according to claim 1, wherein the anionic surfactant is selected from the group consisting of phosphatidylglycerol, cardiolipin, phosphatidylserine, diacylphosphatidylserine, dicetylphosphate, phosphatidic acid, diacylphosphatidic acid, oleic acid, N-dodecanoyl phosphatidylethanoloamine, NSPE (N-succinyl phosphatidylethanolamine), NGPE (N-glutaryl phosphatidylethanolamine), LPG (lysylphosphatidylglycerol) and CHEMS (cholesterylhemisuccinate).

3. The composition according to claim 2, wherein the anionic surfactant is CHEMS (cholesterylhemisuccinate).

4. The composition according to claim 1, wherein the neutral phospholipid is selected from the group consisting of phosphatidylcholine, DPPC (dipalmitoyl phosphatidyl choline), DSPC (1,2-distearoyl-sn-glycero-3-phosphocholine), DMPC(dimyristoylphosphatidylcholine), cholesterol, PEG-PE (polyethylene glycolphosphatidyl ethanolamine), DOPC (dioleoyl phosphatidyl choline) and DOPE (dioleyl phosphatidyl ethanolamine).

5. The composition according to claim 4, wherein the neutral phospholipid is DOPE (dioleyl phosphatidyl ethanolamine).

6. The composition according to claim 1, wherein the liposome is a mixture of CHEMS and DOPE.

7. The composition according to claim 1, wherein the immunostimulatory oligonucleotide contains CpG motifs, CpT motifs, multiple G domains or palindrome sequences forming hairpin secondary structures.

8. A method for treating a hepatocarcinoma comprising administering to a subject a peptide vaccine composition comprising a synthetic peptide consisting of SEQ ID NO:10.

9. A synthetic peptide consisting of the amino acid sequence of SEQ ID NO:10.

10. A pharmaceutical composition against a hepatocarcinoma comprising a synthetic peptide consisting of the amino acid sequence of SEQ ID NO:10.

* * * * *